United States Patent
Barr et al.

(10) Patent No.: US 9,663,522 B2
(45) Date of Patent: May 30, 2017

(54) 3-AMINOCYCLOALKYL COMPOUNDS AS RORGAMMAT INHIBITORS AND USES THEREOF

(71) Applicant: Merck Sharp & Dohme Corp., Rahway, NJ (US)

(72) Inventors: Kenneth J. Barr, Boston, MA (US); John K. Maclean, Brookline, MA (US); Hongjun Zhang, Newton, MA (US); Richard T. Beresis, Shanghai (CN); Neville J. Anthony, Northborough, MA (US); Matthew Daniels, Somerville, MA (US); Blair T. Lapointe, Brookline, MA (US); Nunzio Sciammetta, Sudbury, MA (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 14/421,062

(22) PCT Filed: Aug. 14, 2013

(86) PCT No.: PCT/US2013/054911
§ 371 (c)(1),
(2) Date: Feb. 11, 2015

(87) PCT Pub. No.: WO2014/028600
PCT Pub. Date: Feb. 20, 2014

(65) Prior Publication Data
US 2015/0218169 A1    Aug. 6, 2015

(30) Foreign Application Priority Data

Aug. 15, 2012    (WO) ................ PCT/CN2012/080139

(51) Int. Cl.
| | | |
|---|---|---|
| C07D 487/04 | (2006.01) |
| C07D 401/12 | (2006.01) |
| C07D 403/06 | (2006.01) |
| C07D 471/04 | (2006.01) |
| C07D 519/00 | (2006.01) |
| C07D 213/56 | (2006.01) |
| C07D 401/04 | (2006.01) |
| C07D 403/04 | (2006.01) |
| A61K 31/415 | (2006.01) |
| A61K 31/4155 | (2006.01) |
| A61K 31/437 | (2006.01) |
| A61K 31/4439 | (2006.01) |
| A61K 31/444 | (2006.01) |
| A61K 31/454 | (2006.01) |
| A61K 31/4545 | (2006.01) |

(Continued)

(52) U.S. Cl.
CPC .......... *C07D 487/04* (2013.01); *A61K 31/415* (2013.01); *A61K 31/4155* (2013.01); *A61K 31/437* (2013.01); *A61K 31/444* (2013.01); *A61K 31/4439* (2013.01); *A61K 31/454* (2013.01); *A61K 31/4545* (2013.01); *A61K 31/46* (2013.01); *C07D 213/56* (2013.01); *C07D 231/56* (2013.01); *C07D 401/04* (2013.01); *C07D 401/12* (2013.01); *C07D 401/14* (2013.01); *C07D 403/04* (2013.01); *C07D 403/06* (2013.01); *C07D 451/02* (2013.01); *C07D 471/04* (2013.01); *C07D 519/00* (2013.01)

(58) Field of Classification Search
CPC .. C07D 213/56; C07D 231/56; C07D 401/04; C07D 401/13; C07D 403/04; C07D 451/02; C07D 487/04
USPC ..... 514/210.18, 210.21, 303, 3–4, 318, 322, 514/333, 405; 546/120, 126, 194, 199, 546/256, 275.7; 548/362.1
See application file for complete search history.

(56) References Cited

U.S. PATENT DOCUMENTS 4,670,447 A * 6/1987 Strupczewski ...... C07D 403/04
                                                    514/322
5,639,780 A    6/1997 Lau et al.
(Continued)

FOREIGN PATENT DOCUMENTS

| EP | 0429257 A2 | 5/1991 |
| EP | 2181710 A1 | 5/2010 |

(Continued)

OTHER PUBLICATIONS

Bundgaard "Design of prodrugs" p. 27-32 (1986).*
(Continued)

*Primary Examiner* — Heidi Reese
(74) *Attorney, Agent, or Firm* — Goodwin Procter LLP

(57) ABSTRACT

The present invention relates to compounds according to Formula I and pharmaceutically acceptable salts or solvates thereof. Such compounds can be used in the treatment of RORgammaT-mediated diseases or conditions.

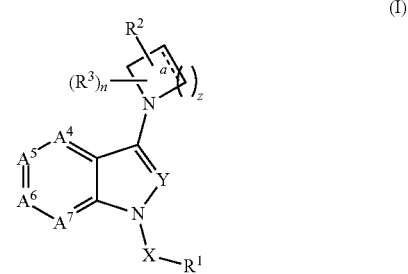

(I)

22 Claims, No Drawings

(51) Int. Cl.
A61K 31/46 (2006.01)
C07D 231/56 (2006.01)
C07D 401/14 (2006.01)
C07D 451/02 (2006.01)

(56) References Cited

U.S. PATENT DOCUMENTS

| | | | | |
|---|---|---|---|---|
| 6,133,290 | A * | 10/2000 | Krushinski, Jr. | C07D 401/04 514/228.2 |
| 7,355,042 | B2 * | 4/2008 | Edgar | A61K 47/48246 540/542 |
| 7,514,465 | B2 | 4/2009 | Kuo et al. | |
| 7,696,229 | B2 * | 4/2010 | Dunn | C07D 401/04 514/254.09 |
| 7,772,252 | B2 * | 8/2010 | Hendrix | A61K 31/496 514/316 |
| 9,095,583 | B2 | 8/2015 | Karstens et al. | |
| 9,273,070 | B2 | 3/2016 | Knochel et al. | |
| 2006/0030612 | A1 | 2/2006 | Steffan et al. | |
| 2006/0100218 | A1 | 5/2006 | Ibrahim et al. | |
| 2009/0124616 | A1 | 5/2009 | Song et al. | |
| 2009/0233955 | A1 | 9/2009 | Frazee et al. | |
| 2010/0317863 | A1 | 12/2010 | Kuzmich et al. | |
| 2011/0150864 | A1 | 6/2011 | Bignan et al. | |
| 2011/0263046 | A1 | 10/2011 | Deuschle et al. | |
| 2015/0191434 | A1 | 7/2015 | Barr et al. | |
| 2015/0210687 | A1 | 7/2015 | Barr et al. | |
| 2015/0218096 | A1 | 8/2015 | Barr et al. | |
| 2015/0297566 | A1 | 10/2015 | Karstens et al. | |

FOREIGN PATENT DOCUMENTS

| | | |
|---|---|---|
| EP | 2487159 A1 | 8/2012 |
| JP | 2007238463 A | 9/2007 |
| WO | WO-96/37467 A1 | 11/1996 |
| WO | WO-2006/052190 A1 | 5/2006 |
| WO | WO-2006/063167 A1 | 6/2006 |
| WO | WO-2007/103308 A2 | 9/2007 |
| WO | WO-2007/144327 A2 | 12/2007 |
| WO | WO-2008/132434 A2 | 11/2008 |
| WO | WO-2008/138889 A2 | 11/2008 |
| WO | WO-2009/015067 A2 | 1/2009 |
| WO | WO-2010/050837 A1 | 5/2010 |
| WO | WO-2010/068483 A2 | 6/2010 |
| WO | WO-2010/150837 A1 | 12/2010 |
| WO | WO-2011/014775 A1 | 2/2011 |
| WO | WO-2011/103189 A1 | 8/2011 |
| WO | WO-2011/146313 A1 | 11/2011 |
| WO | WO-2012/064744 A2 | 5/2012 |
| WO | WO-2012/077932 A2 | 6/2012 |
| WO | WO-2012/106995 A1 | 8/2012 |
| WO | WO-2012/176763 A1 | 12/2012 |

OTHER PUBLICATIONS

Cooper et al. "Polycyclic indaozle . . . ." CA150:56136 (2008).*
Hirose et al. "Benaohytereocyclic der . . . ." CA76:46035 (1972).*
Julia et al. "Research in the indole . . . ." CA61:92261 (1964).*
Improper Markush "Fedral Reg." vol. 76 (27) p. 7162-7175 slides 1, 64-67 (2011).*
Annunziato et al., "Type 17 T helper cells—origins, features and possible roles in rheumatic disease," 5 Nat. Rev. Rheumatol. 325-31 (2009).
Boaventura et al., "Human mucosal leishmaniasis: Neutrophils infiltrate areas of tissue damage that express high levels of Th17-related cytokines," 40 Eur. J. Immunol. 2830-36 (2010).
Bundgaard (ed.), Design of Prodrugs, Elsevier (1985).
Buonocore et al.,"Innate lymphoid cells drive interleukin-23-dependent innate intestinal pathology," 464 Nature 1371-75 (2010).
Burris et al., "Targeting Orphan Nuclear Receptors for Treatment of Metabolic Diseases and Autoimmunity," 19(1) Chem. Biol. 51-59 (2012).

Eberl et al., "An essential function for the nuclear receptor RORγt in the generation of fetal lymphoid tissue inducer cells," 5(1) Nat. Immunol. 64-73 (2004).
Figueroa-Vega et al., "Increased Circulating Pro-Inflammatory Cytokines and Th17 Lymphocytes in Hashimoto's Thyroiditis," 95(2) J. Clin. Endocrinol. Metab. 953-62 (2010).
Gennaro (ed.), Remington: The Science and Practice of Pharmacy, 20th edition (2000).
Guo et al., "Stereospecific microbial reduction of ethyl 1-benzyl-3-oxo-piperidine-4-carboxylate," 17(13) Tetrahedron: Asymmetry 2015-2020 (2006).
He et al., "RORγt, a Novel Isoform of an Orphan Receptor, Negatively Regulates Fas Ligand Expression and IL-2 Production in T Cells," 9 Immunity 797-806 (1998).
Higuchi et al. (eds.), Pro-drugs as Novel Delivery Systems, 14 A.C.S. Symposium Series (1975).
Hirose et al., "RORγ: the third member of ROR/RZR orphan receptor subfamily that is highly expressed in skeletal muscle," 205 Biochem. Biophys. Res. Comm. 1976-83 (1994).
Hueber et al., "Cutting Edge: Mast Cells Express IL-17A in Rheumatoid Arthritis Synovium," 184 J. Immunol. 3336-40 (2010).
Ivanov et al., "The Orphan Nuclear Receptor RORγt Directs the Differentiation Program of Proinflammatory IL-17+ T Helper Cells," 126 Cell 1121-33 (2006).
Jia et al., "The T helper type 17/regulatory T cell imbalance in patients with acute Kawasaki disease," 162 Clin. Exp. Immunol. 131-37 (2010).
Jin et al., "Structural Basis for Hydroxycholesterols as Natural Ligands of Orphan Nuclear Receptor RORγ," 24(5) Mol. Endocrinol. 923-29 (2010).
Kastelein et al., "Discovery and Biology of IL-23 and IL-27: Related but Functionally Distinct Regulators of Inflammation," 25 Annu. Rev. Immunol. 221-42 (2007).
Kurebayashi et al., "Selective LXXLL peptides antagonize transcriptional activation by the retinoid-related orphan receptor RORγ," 315 Biochem. Biophys. Res. Comm. 919-27 (2004).
Louten et aL, "Development and function of TH17 cells in health and disease," 123(5) J. Allergy Clin. Immunol. 1004-11 (2009).
Miossec et al., "Interleukin-17 and Type 17 Helper T Cells," 361(9) New Eng. J. Med. 888-98 (2009.
Roche (ed.), Bioreversible Carriers in Drug Design, Pergamon Press (1987).
Sun et al., "Requirement for RORγ in Thymocyte Survival and Lymphoid Organ Development," 288 Science 2369-72 (2000).
Sutton et al., "Interleukin-1 and IL-23 Induce Innate IL-17 Production from γδ T Cells, Amplifying Th17 Responses and Autoimmunity," 31 Immunity 331-41 (2009).
Wang et al., "Identification of SR1078, a Synthetic Agonist for the Orphan Nuclear Receptors RORα and RORγ," 5(11) ACS Chem. Biol. 1029-34 (2010).
Wang et al., "Modulation of Retinoic Acid Receptor-related Orphan Receptor α and γ Activity by 7-Oxygenated Sterol Ligands," 285(7) J. Bio. Chem. 5013-25 (2010).
Whelligan et al., "Aminopyrazine Inhibitors Binding to an Unusual Inactive Conformation of the Mitotic Kinase Nek2: SAR and Structural Characterization," 53 J. Med. Chem. 7682-98 (2010).
Xie et al., "RORγt Recruits Steroid Receptor Coactivators to Ensure Thymocyte Survival," 175(6) J. Immunol. 3800-09 (2005).
Yang et al., "T Helper 17 Lineage Differentiation is Programmed by Orphan Nuclear Receptors RORα and RORγ," 28 Immunity 29-39 (2008).
Zhou et al., "Use of Homogeneous Time-Resolved Fluorescence Energy Transfer in the Measurement of Nuclear Receptor Activation," 25 Methods 54-61 (2001).
PCT International Search Report (PCT Article 18 and Rules 43 and 44) for PCT/US2013/054911, Mar. 4, 2014.
PCT Written Opinion of the International Searching Authority (PCT Rule 43bis.1) for PCT/US2013/054911, Mar. 4, 2014.
Chen, Hua-Sin et al., "Synthesis and antiplatelet activity of ethyl 4-(1-benzyl-1H-indazol-3-yl)benzoate (YD-3) derivatives," Bioorganic & Medicinal Chemistry, vol. 16, pp. 1262-1278, (2008).

(56) References Cited

OTHER PUBLICATIONS

Varnavas et al., "Anthranilic acid based CCK1 receptor antagonists: preliminary investigation on their second 'touch point,'" 40(6) Euro. J. Med. Chem. 563-81 (2005).
International Search Report and Written Opinion for PCT/US2013/054893, mailed Feb. 14, 2014 (5 pages).
Lee et al., "Synthesis of 1-Benzyl-3-(5'-hydroxymethyl-2'-furyl)indazole Analogues as Novel Antiplatelet Agents," 44 J. Med. Chem. 3746-49 (2001).
André et al., "Disruption of retinoid-related orphan receptor β changes circadian behaviour, causes retinal degeneration and leads to vacillans phenotype in mice," 17(14) The EMBO J. 3867-77 (1998).
Becker-André et al., "Identification of nuclear receptor mRNAs by RT-PCR amplification of conserved zinc-finger motif sequences," 194(3) Biochem. Biophys. Res. Comm. 1371-79 (1993).
Bernhardt et al., "Preparation of Solid Salt-Stabilized Functionalized Organozinc Compounds and their Application to Cross-Coupling and Carbonyl Addition Reactions," 50(39) Angew. Chem. Int. Ed. 9205-9209 (2011).
Boltze et al., "Chemische Struktur and antiphlogistische Wirkung in der Reihe der substituierten Indol-3-essigsauren," 30(8A) Arzneimittel-Forschung 1314-25 (1980).
Cai, et al., "Pivotal Role of Dermal IL-17-Producing γδ T Cells in Skin Inflammation", Immunity (2011) vol. 35, pp. 596-610.
Carlberg et al., "RZRs, a new family of retinoid-related orphan receptors that function as both monomers and homodimers," 8 Mol. Endocrinol. 757-70 (1994).
D. van der Heijde, et al., "Secukinumab Provides Significant and Sustained Inhibition of Joint Structural Damage in a Phase III Study of Active Psoriatic Arthritis" Arthritis & Rheumatology Brief Report, Accepted Article DOI: 10/1002/art, American College of Rheumatology, (2016) pp. 1-27.
Dr. Baeton, et al., "Secukinumab, an Interleukin-17A Inhibitor, in Ankylosing Spondylitis", The New England Journal of Medicine, (2015) vol. 373, pp. 2534-2548.
Dussault et al., "Orphan nuclear receptor RORα-deficient mice display the cerebellar defects of staggerer," 70 Mech. Develop. 147-53 (1998).
El-Sawy et al., "Synthesis, antimicrobial and anti-cancer activities of some new N-ethyl, N-benzyl and N-benzoyl-3-indolyl heterocycles," 62 Acta Pharm. 157-179 (2012).
Extended European Search Report, EP Application No. 12744370.3, Sep. 9, 2014.
Giguère et al., "Isoform-specific amino-terminal domains dictate DNA-binding properties of RORα, a novel family of orphan hormone nuclear receptors," 8 Genes & Develop. 538-53 (1994).
Huh et al., "Small molecule inhibitors of RORγt: Targeting Th17 cells and other applications," 42 Eur. J. Immunol. 2232-2237 (2012).
Inamoto et al., "Palladium-Catalyzed C—H Activation/Intramolecular Amination Reaction: A New Route to 3-Aryl/Alkylindazoles," 9(15) Org. Letts. 2931-34 (2007).
Krueger, "A welcome surprise in psoriasis", Nature Medicine, (2012) vol. 18, No. 12, pp. 1750-1751.
Larhed et al., "Rapid Microwave-Assisted Suzuki Coupling on Solid-Phase," 37(45) Tetrahedron Letters 8219-22 (1996).
Leonardi, et al., "Anti-Interleukin-17 Monoclonal Antibody Ixekizumab in Chronic Plaque Psoriasis", The New England Journal of Medicine, (2012) vol. 366, Iss. 13, pp. 1-10.

Martinez, "Th17-biased RORγt transgenic mice become susceptible to a viral model for multiple sclerosis", Brain, Behavior, and Immunity, (2014) vol. 43, pp. 86-97.
Medvedev et al., "Cloning of a cDNA encoding the murine orphan receptor RZR/RORγ and characterization of its response element," 181 Gene 199-206 (1996).
Nakajima, et al., "IL-17A as an Inducer for Th2 Immune Responses in Murine Atopic Dermatitis Models", Journal of Investigative Dermatology, (2014) vol. 134, pp. 2122-2130.
Ortiz et al., "TOR: a new orphan receptor expressed in the thymus that can modulate retinoid and thyroid hormone signals," 9 Mol. Endocrinol. 1679-91 (1995).
Papp, et al. "Brodalumab, an Anti-Interleukin-17-Receptor Antibody for Psoriasis", The New England Journal of Medicine, (2012) vol. 366, Iss. 13, 9 pgs.
Reckenbeil et al., "Supramolekulare Phosphorylierung kationischer Alkohole mit 3-Arylindol-4-carboxamidin-Struktur," Liebigs Ann. Chem. 1219-29 (1994).
Skepner, et al., "Pharmacologic Inhibition of RORγt RegulatesTh17 Signature Gene Expression and Suppresses Cutaneous Inflammation in Vivo", The Journal of Immunology, (2014) pp. 1-12.
Smith, "The Bench-to-Bedside Story of IL-17 and the Therapeutic Efficacy of its Targeting in Spondyloarthritis", Curr Rheumatol Rep. (2016) vol. 18, pp. 1-10.
Solt et al., "Action of RORs and their ligands in (patho)physiology," 23(12) Trends in Endocrinology and Metabolism. 619-627 (2012).
Tlustochowicz, et al. "Efficacy and Safety of Subcutaneous and Intravenous Loading Dose Regimens of Secukinumab in Patients with Active Rheumatoid Arthritis: Results from a Randomized Phase II Study" The Journal of Rheumatology, (2016) vol. 43, No. 3, pp. 495-503.
Villey et al., "RORγT, a thymus-specific isoform of the orphan nuclear receptor RORγ/TOR, is up-regulated by signaling through the pre-T cell receptor and binds to the TEA promoter," 29 Eur. J. Immunol. 4072-80 (1999).
Wiesenberg et al., "Transcriptional activation of the nuclear receptor RZRα by the pineal gland hormone melatonin and identification of CGP 52608 as a synthetic ligand," 23(3) Nucl. Acids Res. 327-33 (1995).
Xiao, et al., "Small-Molecule RORγt Antagonists Inhibit T Helper 17 Cell Transcriptional Network by Divergent Mechanisms", Immunity (2014) vol. 40, pp. 477-489.
International Search Report and Written Opinion for PCT/US2013/054887, mailed Mar. 18, 2014 (5 pages).
International Search Report and Written Opinion for PCT/US2013/054902, mailed Feb. 28, 2014 (5 pages).
International Search Report from PCT/CN2012/071017, mailed May 24, 2012.
Cheng et al., "Design and synthesis of heterocyclic malonyl-CoA decarboxylase inhibitors," 16 Bioorg. Med. Chem. Lett. 695-700 (2006).
Ciattini et al., "An Efficient Synthesis of 3-Substituted Indoles by Palladium-Catalyzed Coupling Reaction of 3-Tributylstannylindoles with Organic Triflates and Halides," 35(15) Tetrahedron Letters 2405-08 (1994).
Database Caplus [Online] Chemical Abstracts Service, Columbus, Ohio, US; Kusakabe, Kanekazu et al: "Preparation of condensed pyrazole compounds as TTK protein kinase inhibitors", retrieved from STN Database accession No. 2011:1578140 ; & Kusakabe, Kanekazu et al: "Preparation of condensed pyrazole compounds as TTK protein kinase inhibitors", Jpn. Kokai Tokkyo Koho, 134PP. Coden: JKXXAF.

\* cited by examiner

3-AMINOCYCLOALKYL COMPOUNDS AS RORGAMMAT INHIBITORS AND USES THEREOF

CROSS REFERENCE TO RELATED APPLICATIONS

This application is a national stage of International (PCT) Patent Application Serial No. PCT/US2013/054911, filed Aug. 14, 2013, which claims the benefit of and priority to Patent Application Serial No. PCT/CN2012/080139, filed Aug. 15, 2012.

BACKGROUND OF THE INVENTION

Upon activation by antigen-presenting cells naïve T helper cells undergo clonal expansion and will ultimately differentiate in cytokine secreting effector T cells, such as Th1 and Th2 subtypes. A third and distinct effector subset has been identified, which plays a key role in providing immunity to bacteria and fungi at mucosal surfaces (Kastelein et al., *Annu. Rev. Immunol.* 25: 221-242, 2007). This effector T helper cell subset can be distinguished based on its ability to produce large quantities of IL-17/F, IL-21 and IL-22, and is named Th17 (Miossec et al., *New Eng. J. Med.* 2361: 888-898, 2009).

Different T helper subsets are characterized by the expression of lineage specific master transcription factors. Th1 and Th2 effector cells express Tbet and GATA3, respectively. A Thymocyte/T cell specific variant of Retinoic Acid Receptor-related Orphan Receptor (ROR), RORgammaT, is highly expressed in Th17 cells (He et al., *Immunity* 9: 797-806, 1998). RORgammaT belongs to the nuclear hormone receptor superfamily (Hirose et al., *Biochem. Biophys. Res. Comm.* 205: 1976-1983, 1994). RORgammaT is a truncated form of RORgamma, lacking the first N-terminal 21 amino acids and is, in contrast to RORgamma which is expressed in multiple tissues (heart, brain, kidney, lung, liver and muscle), exclusively expressed in cells of the lymphoid lineage and embryonic lymphoid tissue inducers (Sun et al., *Science* 288: 2369-2372, 2000; Eberl et al., *Nat Immunol.* 5: 64-73, 2004).

Studies using heterozygous knock-in mice replacing the RORgammaT open reading frame with GFP (green fluorescent protein), revealed a constitutive expression of GFP in approximately 10% of the CD4+ T cells in the small intestinal lamina propria (LP), co-expressing the Th17 cytokines IL-17/F and IL-22 (Ivanov et al., *Cell* 126: 1121-1133, 2006). In mice deficient for RORgammaT, the number of Th17 cells was markedly decreased in the LP; and in vitro stimulation of CD4+ T cells under Th17 polarizing conditions resulted in a drastic decrease of IL-17 expression. These results were further substantiated via forced expression of RORgammaT in naïve CD4+ T cells, which resulted in an induction of IL-17/F and IL-22 (Ivanov et al., *Cell* 126: 1121-1133, 2006). The foregoing studies demonstrate the importance of RORgammaT in differentiation and stabilization of the Th17 lineage. In addition, a ROR family member, RORalpha, has been demonstrated to be involved in Th17 differentiation and stabilization (Yang et al., *Immunity* 28: 29-39, 2008).

Recently, RORgammaT was shown to play a crucial role in non-Th17 lymphoid cells. In these studies, RORgammaT was critically important in innate lymphoid cells expressing Thy1, SCA-1, and IL-23R proteins. Genetic disruption of RORgamma in a mouse colitis model dependent on these innate lymphoid cells prevented colitis development (Buonocore et al., *Nature* 464: 1371-1375, 2010). In addition, RORgammaT was shown to play a crucial role in other non-Th17 cells, such as mast cells (Hueber et al., *J. Immunol.* 184: 3336-3340, 2010). Finally, RORgammaT expression and secretion of Th17-type of cytokines was reported for Lymphoid Tissue Inducer cells, NK T-cells, NK cells (Eberl et al., *Nat. Immunol.* 5: 64-73, 2004) and gamma-delta T-cells (Sutton et al., *Nat. Immunol.* 31: 331-341, 2009; Louten et al., *J. Allergy Clin. Immunol.* 123: 1004-1011, 2009), suggesting an important function for RORgammaT in these subtypes of cells.

Based on the role of IL-17 producing cells (either Th17 or non-Th17 cells) RORgammaT has been identified as a key mediator in the pathogenesis of several diseases (Louten et al., *J. Allergy Clin. Immunol.* 123: 1004-1011, 2009; Annuziato et al., *Nat. Rev. Rheumatol.* 5: 325-331, 2009). This was confirmed using several disease models representative of autoimmune diseases. Genetic ablation of the RORgamma gene in mice prevented the development of experimental autoimmune diseases, such as experimental autoimmune encephalomyelitis (EAE) and colitis (Ivanov et al., *Cell* 126:1121-33, 2006; Buonocore et al., *Nature* 464: 1371-1375, 2010).

With RORgammaT being a critical mediator in Th17-cells and non-Th17 cells, antagonism of the transcriptional activity of RORgammaT is expected to have a beneficial effect on autoimmune diseases, such as but not limited to rheumatoid arthritis, psoriasis, multiple sclerosis, inflammatory bowel disease, Crohn's disease, and asthma (Annunziato et al., *Nat. Rev. Immunol.* 5: 325-331, 2009; Louten et al., *J. Allergy Clin. Immunol.* 123: 1004-1011, 2009). Antagonism of RORgammaT may also be beneficial in other diseases that are characterized by increased levels of Th17 cells and/or elevated levels of Th17 hallmark cytokines such as IL-17, IL-22 and IL-23. Examples of such diseases are Kawasaki Disease (Jia et al., *Clin. Exp. Immunol.* 162: 131-137, 2010) and Hashimoto's thyroiditis (Figueroa-Vega et al., *J. Clin. Endocrinol. Metab.* 95: 953-62, 2010). Another example includes infectious diseases, such as but not limited to mucosal leishmaniasis (Boaventura et al., *Eur. J. Immunol.* 40: 2830-2836, 2010). In each of the above examples the inhibition may be enhanced by simultaneous inhibition of RORalpha.

Compounds modulating RORgammaT have been reported. Examples of agonists include T0901317 and SR1078 (Wang et al., *ACS Chem. Biol.* 5:1029-1034, 2010). In addition, antagonists have been reported such as 7-oxygenated sterols (Wang et al., *J. Biol. Chem.* 285: 5013-5025, 2009) and compounds described in EP2181710 A1.

Numerous immune and inflammatory disorders continue to afflict millions of patients worldwide. Although significant advances have been made in treating these disorders, current therapies do not provide satisfactory results for all patients due to, for example, detrimental side effects or insufficient efficacy. One exemplary immune disorder in need of better therapy is psoriasis. Various therapeutics have been developed in an attempt to treat psoriasis. However, the traditional therapies for psoriasis often have toxic adverse effects. An exemplary inflammatory disorder in need of better treatment is rheumatoid arthritis. Numerous therapeutics have been developed in an attempt to treat this disorder. However, some patients develop resistance to current therapies.

Accordingly, a need exists for improved treatments for immune disorders and inflammatory disorders. The present invention addresses this need and provides other related advantages.

SUMMARY OF THE INVENTION

The present invention provides compounds that alter the interaction of coregulator proteins with RORgammaT and thereby antagonize RORgammaT-mediated transcriptional activity, their use for the treatment of RORgammaT-mediated diseases or conditions, in particular autoimmune diseases and inflammatory diseases, as well as pharmaceutical compositions comprising such compounds and pharmaceutical carriers.

DETAILED DESCRIPTION OF THE INVENTION

The present invention provides a compound according to Formula I

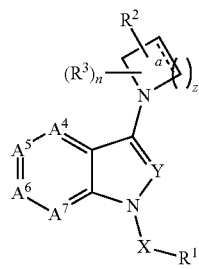

I or a pharmaceutically acceptable salt or solvate thereof, wherein:
a is a bond or no bond;
z is 1, 2 or 3;
X is $CH_2$, C(O), $CHR^b$
Y is CH or N or $CR^a$;
n=0, 1, 2, 3 or 4;
$A^4$ is $CR^4$ or N,
$A^5$ is $CR^5$ or N,
$A^6$ is $CR^6$ or N,
$A^7$ is $CR^7$ or N,
with the proviso that no more than one or two of $A^4$-$A^7$ can be N;
$R^a$ is $(C_{1-4})$alkyl;
$R^b$ is $(C_{1-4})$alkyl;
$R^1$ is
  (i) $(C_{3-12})$carbocyclyl; or
  (ii) a 4- to 12-membered heterocyclyl,
  both (i) and (ii) optionally substituted with one, two, three, four or five $R^8$;
$R^2$ is hydroxycarbonyl, hydroxyl, halo$(C_{1-4})$alkyl, hydroxycarbonyl$(C_{1-10})$alkyl, $(C_{1-10})$alkylsulfoxyaminocarbonyl, or carbamoyl;
$R^3$ is hydrogen, halogen, cyano, nitro, hydroxy, (C1-3)alkylC(O)O—, phenyl, $(C_{1-4})$alkyl, oxo, or $(C_{1-4})$alkoxy, wherein $(C_{1-4})$alkyl and $(C_{1-4})$alkoxy are optionally substituted with one or more halogen;
optionally when z is 3, a represents no bond and two $R^3$ groups are attached to the two carbons flanking the N atom of the piperidinyl ring formed when z is 3, such that the two $R^3$ groups join to form a 2- or 3-carbon bridge with the piperidinyl ring to form an azabicyclo[3.2.1]octanyl or azabicyclo[3.3.1]nonanyl ring;
$R^4$, $R^5$, $R^6$ and $R^7$ independently are H, halogen, amino, cyano, hydroxy, $(C_{1-3})$alkoxy, $(C_{1-4})$alkyl, $(C_{0-10})$alkyl) aminocarbonyl, $(di)(C_{1-6})$alkylaminocarbonyl or amino $(C_{1-4})$alkyl, wherein $(C_{1-3})$alkoxy, $(C_{1-4})$alkyl, $(C_{0-10}$alkyl)aminocarbonyl, $(di)(C_{1-6})$alkylaminocarbonyl and amino$(C_{1-4})$alkyl are optionally substituted with one or more halogen, hydroxyl or $(C_{1-3})$alkoxy; or a group having the formula

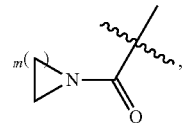

optionally substituted with one or more of the following: $(C_{1-10})$alkyl, halogen, amino, cyano, hydroxy, $(C_{1-3})$alkoxy, and wherein m is 1, 2, 3, or 4;
$R^8$ is halogen, cyano, amino, nitro, hydroxy, oxo, $H_2NC(O)$—, $(C_{1-3})$alkoxycarbonyl, $(di)(C_{1-6})$alkylaminocarbonyl, $(C_{1-4})$alkyl, $(C_{3-7})$cycloalkyl, $(C_{3-5})$heterocycloalkyl, or $(C_{1-3})$alkoxy, wherein $(C_{1-3})$alkoxycarbonyl, $(di)(C_{1-6})$alkylaminocarbonyl, $(C_{1-4})$alkyl and $(C_{1-3})$alkoxy are optionally substituted with one, two or three halogens.

In a first embodiment of the compound having Formula I is a compound having Formula Ia

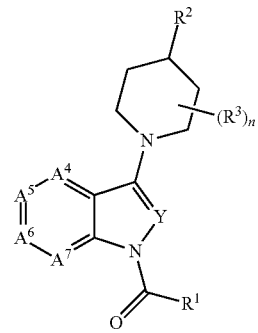

Ia and a pharmaceutically acceptable salt or solvate thereof.

In a second embodiment of the compound having Formula I is a compound having Formula Ib

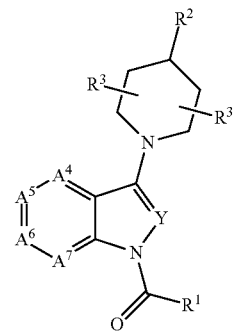

Ib and a pharmaceutically acceptable salt or solvate thereof.

In a first subset of the second embodiment is a compound wherein Y is N.

In a second subset of the second embodiment is a compound having Formula Ic

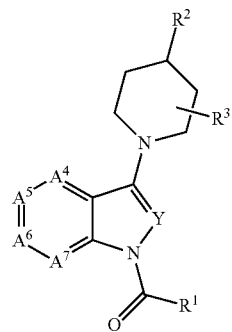

Ic and a pharmaceutically acceptable salt or solvate thereof.

In a first subset of the first embodiment is a compound having Formula Id

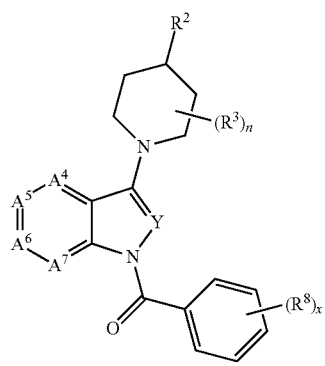

Id wherein x is 1, 2, 3, 4 or 5, and a pharmaceutically acceptable salt or solvate thereof.

In a subset of the compound having Formula Id is a compound having Formula Ie

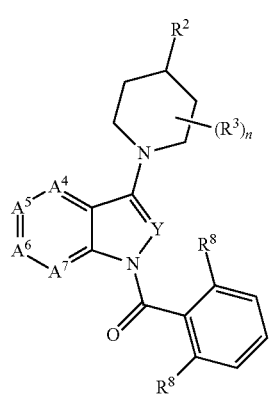

Ie and a pharmaceutically acceptable salt or solvate thereof.

In a subset of the compound having Formula Ie is a compound having Formula If

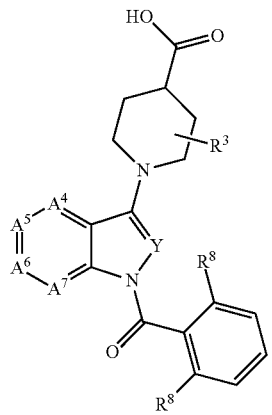

If and a pharmaceutically acceptable salt or solvate thereof.

In a subset of the compound having Formula If is a compound having Formula Ig

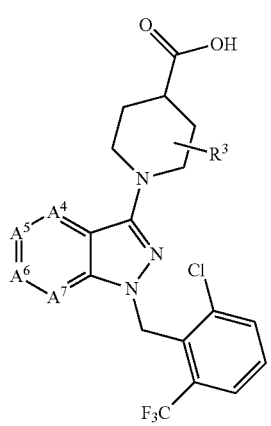

Ig and a pharmaceutically acceptable salt or solvate thereof.

In a second subset of the first embodiment is a compound wherein $A^4, A^5, A^6, A^7$ are selected from the group consisting of: (i) $CR^4, CR^5, CR^6, CR^7$; (ii) N, $CR^5, CR^6, CR^7$; (iii) $CR^4$, N, $CR^6, CR^7$; (iv) $CR^4, CR^5$, N, $CR^7$; (v) $CR^4, CR^5, CR^6$, N; (vi) N, N, $CR^6, CR^7$; (vii) $CR^4$, N, N, $CR^7$; (viii) $CR^4, CR^5$, N, N; (ix) N, $CR^5$, N, $CR^7$; (x) $CR^4$, N, $CR^6$, N; and (xi) N, $CR^5, CR^6$, N.

In a third subset of the first embodiment is a compound wherein $A^4, A^5, A^6, A^7$ is (i) $CR^4, CR^5, CR^6, CR^7$; or (ii) N, $CR^5, CR^6, CR^7$; and Y is N.

In a fourth subset of the first embodiment is compound wherein $R^1$ is (i) $(C_{3-7})$cycloalkyl or $(C_{3-5})$heterocycloalkyl, both optionally substituted with one or more $R^8$, wherein $R^8$ is selected from halogen, amino, cyano, nitro, hydroxy, $H_2NC(O)$—, $(C_{1-3})$alkoxycarbonyl, (di)$(C_{1-6})$alkylaminocarbonyl, $(C_{1-4})$alkyl or $(C_{1-3})$alkoxy, wherein $(C_{1-3})$alkoxycarbonyl, (di)$(C_{1-6})$alkylaminocarbonyl, $(C_{1-4})$alkyl and $(C_{1-3})$alkoxy are optionally substituted with one or more halogens; (ii) $(C_{2-9})$heteroaryl, optionally substituted with one or more $R^8$, wherein $R^8$ is selected from halogen, amino, cyano, nitro, hydroxy, $H_2NC(O)$—, $(C_{1-3})$alkoxycarbonyl, (di)($C_{1-6}$)alkylaminocarbonyl, ($C_{1-4}$)alkyl or ($C_{1-3}$)alkoxy, wherein ($C_{1-3}$)alkoxycarbonyl, (di)($C_{1-6}$)alkylaminocarbonyl, ($C_{1-4}$)alkyl and ($C_{1-3}$)alkoxy are optionally substituted with one or more halogens; or (iii) ($C_{6-14}$)aryl, optionally substituted with one or more $R^8$, wherein $R^8$ is selected from halogen, amino, cyano, nitro, hydroxy, $H_2NC(O)$—, ($C_{1-3}$)alkoxycarbonyl, (di)($C_{1-6}$)alkylaminocarbonyl, ($C_{1-4}$)alkyl or ($C_{1-3}$)alkoxy, wherein ($C_{1-3}$)alkoxycarbonyl, (di)($C_{1-6}$)alkylaminocarbonyl, ($C_{1-4}$)alkyl or ($C_{1-3}$)alkoxy are optionally substituted with one or more halogens.

In a fifth subset of the first embodiment is compound wherein $R^1$ is ($C_{2-9}$)heteroaryl, or (ii) ($C_{6-14}$)aryl, optionally substituted with one, two, three, four or five $R^8$. In a further subset $R^8$ is selected from halogen, amino, cyano, nitro, hydroxy, ($C_{1-3}$)alkoxycarbonyl, ($C_{1-4}$)alkyl, ($C_{1-3}$)alkoxy, wherein ($C_{1-3}$)alkoxycarbonyl, ($C_{1-4}$)alkyl and ($C_{1-3}$)alkoxy are optionally substituted with one or more halogens.

In a sixth subset of the first embodiment, $R^1$ is ($C_{6-14}$)aryl, optionally substituted with one, two, three, four or five $R^8$. In a further subset $R^8$ is selected from halogen, cyano, ($C_{1-3}$)alkoxycarbonyl, ($C_{1-4}$)alkyl or ($C_{1-3}$)alkoxy, wherein ($C_{1-3}$)alkoxycarbonyl, ($C_{1-4}$)alkyl and ($C_{1-3}$)alkoxy are optionally substituted with one, two or three halogens.

In a seventh subset of the first embodiment, $R^1$ is phenyl, naphthyl, pyridinyl, quinolinyl, benzooxadiazolyl, thiophenyl, isoxazolyl, or benzothiophenyl, each optionally substituted with one or more $R^8$. In a further subset $R^8$ is selected from halogen, amino, cyano, nitro, hydroxy, ($C_{1-3}$)alkoxycarbonyl, ($C_{1-4}$)alkyl or ($C_{1-3}$)alkoxy, wherein ($C_{1-3}$)alkoxycarbonyl, ($C_{1-4}$)alkyl and ($C_{1-3}$)alkoxy are optionally substituted with one or more halogens.

In an eighth subset of the first embodiment, $R^1$ is phenyl, optionally substituted with one, two or three $R^8$. In a further subset $R^8$ is selected from halogen, amino, cyano, nitro, hydroxy, ($C_{1-3}$)alkoxycarbonyl, ($C_{1-4}$)alkyl or ($C_{1-3}$)alkoxy, wherein ($C_{1-3}$)alkoxycarbonyl, ($C_{1-4}$)alkyl and ($C_{1-3}$)alkoxy are optionally substituted with one or more halogens.

In a ninth subset of the first embodiment, $R^2$ is C(O)OH.

A still further embodiment of the compounds of Formula I, Ia, Ib, Ic, Id, Ie, If, and Ig are compounds wherein one of $R^4$, $R^5$, $R^6$, and $R^7$ is other than hydrogen.

The invention also relates to those compounds wherein all specific definitions for $A^1$ through $A^4$, $R^1$ through $R^8$, Y, m, n, x and z, and all substituent groups in the various aspects of the inventions defined hereinabove occur in any combination within the definition of the compound of Formula I.

Non-limiting examples of the compound of the present invention include:

(3R,4R and 3S,4S)-1-(1-{[2-chloro-6-(trifluoromethyl)phenyl]carbonyl}-1H-pyrazolo[4,3-b]pyridin-3-yl)-3-methylpiperidine-4-carboxylic acid;

8-(1-{[2-chloro-6-(trifluoromethyl)phenyl]carbonyl}-1H-pyrazolo[4,3-b]pyridin-3-yl)-8-azabicyclo[3.2.1]octane-3-carboxylic acid;

1-(1-{[2-chloro-6-(trifluoromethyl)phenyl]carbonyl}-4-fluoro-1H-indazol-3-yl)pyrrolidine-3-carboxylic acid;

(3R,4R and 3S,4S)-1-(1-{[2-chloro-6-(trifluoromethyl)phenyl]carbonyl}-4-fluoro-1H-indazol-3-yl)-3-methylpiperidine-4-carboxylic acid;

1-(1-{[2-chloro-6-(trifluoromethyl)phenyl]carbonyl}-4-fluoro-1H-indazol-3-yl)-4-methylpiperidine-4-carboxylic acid;

1-(1-{[2-chloro-6-(trifluoromethyl)phenyl]carbonyl}-4-fluoro-1H-indazol-3-yl)-4-(trifluoromethyl)piperidin-4-ol;

1-(1-{[2-chloro-6-(trifluoromethyl)phenyl]carbonyl}-4-fluoro-1H-indazol-3-yl)-4-phenylpiperidine-4-carboxylic acid;

cis-4-[(1-{[2-chloro-6-(trifluoromethyl)phenyl]carbonyl}-4-fluoro-1H-indazol-3-yl)amino]cyclohexanecarboxylic acid;

1-(1-{[2-chloro-6-(trifluoromethyl)phenyl]carbonyl}-4-fluoro-1H-indazol-3-yl)piperidine-4-carboxylic acid;

[1-(1-{[2-chloro-6-(trifluoromethyl)phenyl]carbonyl}-4-fluoro-1H-indazol-3-yl)piperidin-4-yl]acetic acid;

1-(1-{[2-chloro-6-(trifluoromethyl)phenyl]carbonyl}-1H-pyrazolo[4,3-b]pyridin-3-yl)-3-hydroxypiperidine-4-carboxylic acid;

1-(1-{[2-chloro-6-(trifluoromethyl)phenyl]carbonyl}-1H-pyrazolo[4,3-b]pyridin-3-yl)-1,2,3,6-tetrahydropyridine-4-carboxylic acid;

1-(1-{[2-chloro-6-(trifluoromethyl)phenyl]carbonyl}-1H-pyrazolo[4,3-b]pyridin-3-yl)piperidine-4-carboxylic acid;

1-(1-{[2-chloro-6-(trifluoromethyl)phenyl]carbonyl}-1H-pyrazolo[4,3-b]pyridin-3-yl)-4-fluoropiperidine-4-carboxylic acid;

1-(1-{[2-chloro-6-(trifluoromethyl)phenyl]carbonyl}-1H-pyrazolo[4,3-b]pyridin-3-yl)-3-fluoropiperidine-4-carboxylic acid;

1-(1-{[2-chloro-6-(trifluoromethyl)phenyl]carbonyl}-1H-pyrazolo[4,3-b]pyridin-3-yl)-4-(trifluoromethyl)piperidin-4-ol;

[1-(1-{[2-chloro-6-(trifluoromethyl)phenyl]carbonyl}-1H-pyrazolo[4,3-b]pyridin-3-yl)azetidin-3-yl]acetic acid;

1-[1-{[2-chloro-6-(trifluoromethyl)phenyl]carbonyl}-6-(dimethylcarbamoyl)-1H-indazol-3-yl]piperidine-4-carboxylic acid; 1-[1-{[2-chloro-6-(trifluoromethyl)phenyl]carbonyl}-6-(hydroxymethyl)-1H-indazol-3-yl]piperidine-4-carboxylic acid;

1-(1-(2-chloro-6-(trifluoromethyl)benzoyl)-4-fluoro-1H-indazol-3-yl)pyrrolidine-3-carboxylic acid;

1-(1-(2-chloro-6-(trifluoromethyl)benzoyl)-4-methyl-1H-indazol-3-yl)piperidine-4-carboxylic acid;

1-(1-(2-chloro-6-cyclopropylbenzoyl)-4-fluoro-1H-indazol-3-yl)piperidine-4-carboxylic acid;

1-(1-(2-chloro-6-cyclobutylbenzoyl)-4-fluoro-1H-indazol-3-yl)piperidine-4-carboxylic acid;

(3R,4S and 3S,4R)-1-(1-(2-chloro-6-(trifluoromethyl)benzoyl)-4-fluoro-1H-indazol-3-yl)-3-methylpiperidine-4-carboxylic acid;

(3R,4R and 3S,4S)-1-(1-(2-chloro-6-(trifluoromethyl)benzoyl)-4-fluoro-1H-indazol-3-yl)-3-methylpiperidine-4-carboxylic acid;

8-(1-(2-chloro-6-(trifluoromethyl)benzoyl)-4-fluoro-1H-indazol-3-yl)-8-azabicyclo[3.2.1]octane-3-carboxylic acid;

1R,5S)-9-(1-(2-chloro-6-(trifluoromethyl)benzoyl)-4-fluoro-1H-indazol-3-yl)-9-azabicyclo[3.3.1]nonane-3-carboxylic acid;

1-(1-(2-chloro-6-(trifluoromethyl)benzoyl)-4-fluoro-1H-indazol-3-yl)-2-ethylpiperidine-4-carboxylic acid;

1-(1-(2-chloro-6-(trifluoromethyl)benzoyl)-4-fluoro-1H-indazol-3-yl)-4-hydroxypiperidine-4-carboxylic acid;

(3S,4R or 3R,4S)-1-(1-(2-chloro-6-cyclopropylbenzoyl)-4-fluoro-1H-indazol-3-yl)-3-hydroxypiperidine-4-carboxylic acid;

(3R,4S or 3S,4R)-1-(1-(2-chloro-6-cyclopropylbenzoyl)-4-fluoro-1H-indazol-3-yl)-3-hydroxypiperidine-4-carboxylic acid;

(3S,4R or 3R,4S)-1-(1-(2-chloro-6-(trifluoromethyl)benzoyl)-4-fluoro-1H-indazol-3-yl)-3-hydroxypiperidine-4-carboxylic acid;

(3R,4S or 3S,4R)-1-(1-(2-chloro-6-(trifluoromethyl)benzoyl)-4-fluoro-1H-indazol-3-yl)-3-hydroxypiperidine-4-carboxylic acid;

(3R,4R and 3S,4S)-1-(1-(2-chloro-6-(trifluoromethyl)benzoyl)-4-fluoro-1H-indazol-3-yl)-3-hydroxypiperidine-4-carboxylic acid;

(3R,4R)-1-(1-(2-chloro-6-cyclopropylbenzoyl)-4-fluoro-1H-indazol-3-yl)-3-hydroxy-4-methylpiperidine-4-carboxylic acid;

(3S,4R or 3R,4S)-1-(1-(2-chloro-6-cyclopropyl benzoyl)-4-fluoro-1H-indazol-3-yl)-3-hydroxy-4-methylpiperidine-4-carboxylic acid;

(3R,4S or 3S,4R)-1-(1-(2-chloro-6-cyclopropylbenzoyl)-4-fluoro-1H-indazol-3-yl)-3-hydroxy-4-methylpiperidine-4-carboxylic acid;

1-(1-(2-chloro-6-(trifluoromethyl)benzoyl)-4-fluoro-1H-indazol-3-yl)-2-oxopiperidine-4-carboxylic acid;

1-(1-(2-chloro-6-(trifluoromethyl)benzoyl)-4-fluoro-1H-indazol-3-yl)-2-methylpiperidine-4-carboxylic acid;

1-(1-(2-chloro-6-(trifluoromethyl)benzoyl)-6-(3-methoxy azetidine-1-carbonyl)-1H-indazol-3-yl)piperidine-4-carboxylic acid;

(S)-1-(1-(2-chloro-6-(trifluoromethyl)benzoyl)-6-(2-methylpyrrolidine-1-carbonyl)-1H-indazol-3-yl)piperidine-4-carboxylic acid;

(S)-1-(1-(2-chloro-6-(trifluoromethyl)benzoyl)-6-(3-methoxypyrrolidine-1-carbonyl)-1H-indazol-3-yl)piperidine-4-carboxylic acid; and (R)-1-(1-(2-chloro-6-(trifluoromethyl)benzoyl)-6-(3-methoxypyrrolidine-1-carbonyl)-1H-indazol-3-yl)piperidine-4-carboxylic acid.

The terms used herein have their ordinary meaning and the meaning of such terms is independent at each occurrence thereof. That notwithstanding, and except where stated otherwise, the following definitions apply throughout the specification and claims. Chemical names, common names, and chemical structures may be used interchangeably to describe the same structure. If a chemical compound is referred to using both a chemical structure and a chemical name, and an ambiguity exists between the structure and the name, the structure predominates. These definitions apply regardless of whether a term is used by itself or in combination with other terms, unless otherwise indicated. Hence, the definition of "alkyl" applies to "alkyl" as well as the "alkyl" portions of "hydroxyalkyl," "fluoroalkyl," "alkoxy", etc.

As used herein, and throughout this disclosure, the following terms, unless otherwise indicated, shall be understood to have the following meanings:

The term "alkyl," as used herein, refers to an aliphatic hydrocarbon group having one of its hydrogen atoms replaced with a bond having the specified number of carbon atoms. In different embodiments, an alkyl group contains, for example, from 1 to 6 carbon atoms ($C_1$-$C_6$ alkyl) or from 1 to 3 carbon atoms ($C_1$-$C_3$ alkyl). Non-limiting examples of alkyl groups include methyl, ethyl, n-propyl, isopropyl, n-butyl, sec-butyl, isobutyl, tert-butyl, n-pentyl, neopentyl, isopentyl, n-hexyl, isohexyl and neohexyl. In one embodiment, an alkyl group is linear. In another embodiment, an alkyl group is branched.

Unless specified otherwise, "alkyl" includes both branched- and straight-chain saturated aliphatic hydrocarbon groups, including all isomers, having the specified number of carbon atoms; for example, "$C_{1-6}$ alkyl" (or "$C_1$-$C_6$ alkyl") includes all of the hexyl alkyl and pentyl alkyl isomers as well as n-, iso-, sec- and t-butyl, n- and isopropyl, ethyl and methyl. "Alkylene" refers to both branched- and straight-chain saturated aliphatic hydrocarbon groups, including all isomers, having the specified number of carbons, and having two terminal end chain attachments; for example, the term "A-$C_4$alkylene-B" represents, for example, A-$CH_2$—$CH_2$—$CH_2$—$CH_2$—B, A-$CH_2$—$CH_2$—$CH(CH_3)$—$CH_2$—B, A-$CH_2$—CH($CH_2CH_3$)—B, A-$CH_2$—C($CH_3$)($CH_3$)—B, and the like. "Alkoxy" represents a linear or branched alkyl group of indicated number of carbon atoms attached through an oxygen bridge; for example "$C_1$-$C_6$ alkoxy" includes —$OCH_3$, —$OCH_2CH_3$, —$OCH(CH_3)_2$, —$O(CH_2)_5CH_3$, and the like.

Unless otherwise specifically noted as only "unsubstituted" or only "substituted", alkyl groups are unsubstituted or substituted with 1 to 3 substituents on each carbon atom, with halo, $C_1$-$C_{20}$ alkyl, $CF_3$, $NH_2$, $N(C_1$-$C_6$ alkyl$)_2$, $NO_2$, oxo, CN, $N_3$, —OH, —O($C_1$-$C_6$ alkyl), $C_3$-$C_{10}$ cycloalkyl, $C_2$-$C_6$ alkenyl, $C_2$-$C_6$ alkynyl, ($C_0$-$C_6$ alkyl) S(O)$_{0-2}$—, ($C_0$-$C_6$ alkyl)S(O)$_{0-2}$($C_0$-$C_6$ alkyl)-, ($C_0$-$C_6$ alkyl)C(O)NH—, $H_2$N—C(NH)—, $H_2$N—C(O)(NH)—, —O($C_1$-$C_6$ alkyl)$CF_3$, ($C_0$-$C_6$ alkyl)C(O)—, ($C_0$-$C_6$ alkyl)OC(O)—, ($C_0$-$C_6$ alkyl)O($C_1$-$C_6$ alkyl)-, ($C_0$-$C_6$ alkyl)C(O)$_{1-2}$($C_0$-$C_6$ alkyl)-, ($C_0$-$C_6$ alkyl)OC(O)NH—, —NH($C_1$-$C_6$ alkyl)NHC(O)NH ($C_1$-$C_6$ alkyl), NHC(O)O$C_1$-$C_6$ alkyl, —NH($C_1$-$C_6$ alkyl) $NHSO_2$($C_1$-$C_6$ alkyl), —($C_0$-$C_6$ alkyl)$NHSO_2$($C_1$-$C_6$ alkyl), aryl, aralkyl, heterocycle, heterocyclylalkyl, halo-aryl, halo-aralkyl, halo-heterocycle, halo-heterocyclylalkyl, cyano-aryl, cyano-aralkyl, cyano-heterocycle and cyano-heterocyclylalkyl.

The term "alkenyl" means a straight or branched carbon chain having the specified number of carbon atoms with at least one carbon-carbon double bond. Examples of alkenyl include, but are not limited to, vinyl, allyl, isopropenyl, pentenyl, hexenyl, heptenyl, 1-propenyl, 2-butenyl, 2-methyl-2-butenyl, 2,4-hexadienyl, and the like.

The term "alkynyl" means a straight or branched carbon chain having the specified number of carbon atoms with at least one carbon-carbon triple bond. Examples of alkynyl include, but are not limited to ethynyl, propargyl, 1-propynyl, 2-butynyl, and the like.

The term "carbocycle" (and variations thereof such as "carbocyclic" or "carbocyclyl") as used herein, unless otherwise indicated, refers to (i) a $C_3$ to $C_8$ monocyclic, saturated or unsaturated ring or (ii) a $C_7$ to $C_{12}$ bicyclic saturated or unsaturated ring system. Each ring in (ii) is either attached via a bond to, or fused (including spirofused) to, the other ring, and each ring is saturated or unsaturated. The carbocycle may be attached to the rest of the molecule at any carbon atom that results in a stable compound.

Saturated carbocyclics form a subset of carbocycles in which the entire ring system (mono- or polycyclic) is saturated. Saturated monocyclic carbocyclic rings are also referred to as cycloalkyl rings, e.g., cyclopropyl, cyclobutyl, etc. The fused bicyclic carbocycles are a further subset of the carbocycles in which a $C_7$ to $C_{10}$ bicyclic ring system in which each ring is saturated or unsaturated and two adjacent carbon atoms (or in the case of spirofused, one carbon atom) are shared by each of the rings in the ring system. A saturated bicyclic carbocycle is one in which both rings are saturated. An unsaturated bicyclic carbocycle is one in which one ring is unsaturated and the other is unsaturated or saturated. Unless otherwise noted, carbocycle is unsubstituted or substituted with $C_{1-6}$ alkyl, $C_{1-6}$ alkenyl, $C_{1-6}$ alkynyl, aryl, halogen, $NH_2$ or OH. A subset of the fused bicyclic unsaturated carbocycles are those bicyclic carbocycles in which one ring is a benzene ring and the other ring is saturated or unsaturated, with attachment via any carbon atom that results in a stable compound. Representative examples of this subset include the following:

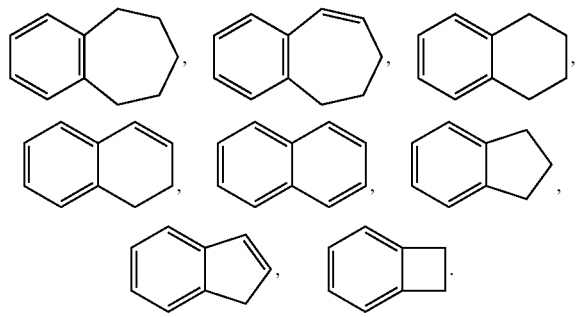

Aromatic carbocycles form another subset of the carbocycles. The term "aryl" refers to aromatic mono- and polycarbocyclic ring systems in which the individual carbocyclic rings in the polyring systems are fused or attached to each other via a single bond. Suitable aryl groups include phenyl, naphthyl, and biphenyl.

The term "cycloalkyl" means a cyclic ring of an alkane having the specified total ring carbon atoms; for example cyclopropyl, cyclobutyl, cyclopentyl, cyclohexyl.

The term "heterocycle" (and variations thereof such as "heterocyclic" or "heterocyclyl") broadly refers to (i) a stable 4- to 8-membered, saturated or unsaturated monocyclic ring, or (ii) a stable 7- to 12-membered bicyclic ring system, wherein each ring in (ii) is either attached via a bond to, or fused (including spirofused) to, the other ring, and each ring is saturated or unsaturated, and the monocyclic ring or bicyclic ring system contains one or more heteroatoms (e.g., from 1 to 6 heteroatoms, or from 1 to 4 heteroatoms) selected from N, O and S and a balance of carbon atoms (the monocyclic ring typically contains at least one carbon atom and the ring systems typically contain at least two carbon atoms); and wherein any one or more of the nitrogen and sulfur heteroatoms is optionally oxidized, and any one or more of the nitrogen heteroatoms is optionally quaternized. Unless otherwise specified, the heterocyclic ring may be attached at any heteroatom or carbon atom, provided that attachment results in the creation of a stable structure. Unless otherwise specified, when the heterocyclic ring has substituents, it is understood that the substituents may be attached to any atom in the ring, whether a heteroatom or a carbon atom, provided that a stable chemical structure results.

Saturated heterocyclics form a subset of the heterocycles; i.e., the term "saturated heterocyclic" generally refers to a heterocycle as defined above in which the entire ring system (whether mono- or poly-cyclic) is saturated. The term "saturated heterocyclic ring" refers to a 4- to 8-membered saturated monocyclic ring or a stable 7- to 12-membered bicyclic ring system that consists of carbon atoms and one or more heteroatoms selected from N, O and S. Representative examples include piperidinyl, piperazinyl, azepanyl, pyrrolidinyl, pyrazolidinyl, imidazolidinyl, oxazolidinyl, isoxazolidinyl, morpholinyl, thiomorpholinyl, thiazolidinyl, isothiazolidinyl, 1,4-dioxanyl, 1,4-thioxanyl, tetrahydropyranyl, tetrahydrofuryl (or tetrahydrofuranyl), tetrahydrothienyl, and tetrahydrothiopyranyl.

Heteroaromatics form another subset of the heterocycles; i.e., the term "heteroaromatic" (alternatively "heteroaryl") generally refers to a heterocycle as defined above in which the entire ring system (whether mono- or poly-cyclic) is an aromatic ring system. The term "heteroaromatic ring" refers a 5- or 6-membered monocyclic aromatic ring or a 7- to 12-membered bicyclic aromatic ring, and that consists of carbon atoms and one or more heteroatoms selected from N, O and S. In the case of substituted heteroaryl rings containing at least one nitrogen atom (e.g., pyridine), such substitutions can be those resulting in N-oxide formation. Representative examples of monocyclic heteroaromatic rings include pyridyl, pyrrolyl, pyrazinyl, pyrimidinyl, pyridazinyl, thienyl (or thiophenyl), thiazolyl, furanyl, imidazolyl, pyrazolyl, triazolyl, tetrazolyl, oxazolyl, isoxazolyl, oxadiazolyl, thiazolyl, isothiazolyl, and thiadiazolyl. Examples of bicyclic heteroaromatic rings include benzotriazolyl, indolyl, benzoxazolyl, benzofuranyl, benzothienyl, benzothiazolyl, benzimidazolyl, isoindolyl, indazolyl, quinoxalinyl, quinazolinyl, cinnolinyl, quinolinyl, isoquinolinyl, naphthyridinyl, pyrazolo[3,4-b]pyridine, imidazo[2,1-b](1,3)thiazole, (i.e., 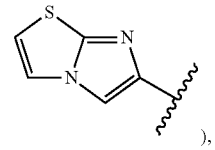), 6-(1-pyrrolyl)-3-pyridyl, 4-(1-pyrrolyl)phenyl, 4-(pyrid-3-yl)phenyl, 4-(pyrid-4-yl)phenyl, and benzothiophenyl (i.e. 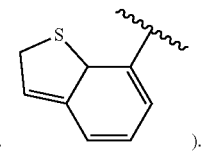).

Another subset of heterocycles is unsaturated heterocycles in which one or both rings are unsaturated (provided the entire ring system is not aromatic). Representative examples of unsaturated heterocycles include dihydrofuranyl, dihydrothienyl, dihydropyranyl, dihydroimidazolyl, indolinyl, isoindolinyl, chromanyl, isochromanyl, tetrahydroquinolinyl, tetrahydroisoquinolinyl, tetrahydronaphthyridinyl, 2,3-dihydrobenzofuranyl, 1,4-benzoxazinyl, 1,3-benzoxazolinyl, 2,3-dihydrobenzo-1,4-dioxinyl (i.e., 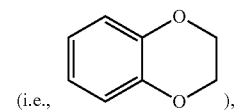), and benzo-1,3-dioxolyl (i.e., 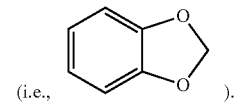).

In certain contexts herein,

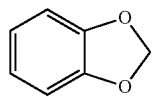

is alternatively referred to as phenyl having as a substituent methylenedioxy attached to two adjacent carbon atoms. Also included are groups such as chromone and coumarin.

Unless otherwise specifically noted as only unsubstituted or only substituted, cycloalkyl, cycloalkenyl, heterocycloalkyl, aryl (including phenyl) and heteroaryl groups are unsubstituted or substituted (also referred to as "optionally substituted"). Unless the substituents are specifically provided, substituents for substituted or optionally substituted cycloalkyl, heterocycloalkyl, cycloalkenyl, aryl (including phenyl, and as an isolated substituent or as part of a substituent such as in aryloxy and aralkyl), heteroaryl (as an isolated substituent or as part of a substituent such as in heteroaryloxy and heteroaralkyl) are one to three groups independently selected from halogen (or halo), $C_1$-$C_6$ alkyl optionally substituted with one to five fluorine, $NH_2$, $N(C_1$-$C_6$ alkyl$)_2$, $NO_2$, oxo, CN, $N_3$, —OH, —O($C_1$-$C_6$ alkyl) optionally substituted with one to five fluorine, $C_3$-$C_{10}$ cycloalkyl, $(C_{3-7})$cycloalkyl, $(C_{3-5})$heterocycloalkyl, $C_2$-$C_6$ alkenyl, $C_2$-$C_6$ alkynyl, $(C_0$-$C_6$ alkyl$)S(O)_{0-2}$—, aryl-$S(O)_{0-2}$—, $(C_0$-$C_6$ alkyl$)S(O)_{0-2}(C_0$-$C_6$ alkylene)-, $(C_0$-$C_6$ alkyl$)C(O)NH$—, $H_2N$—$C(NH)$—, $(C_0$-$C_6$ alkyl$)C(O)$—, $(C_0$-$C_6$ alkyl$)OC(O)$—, $(C_0$-$C_6$alkyl$)O(C_1$-$C_6$ alkylene)-, $(C_0$-$C_6$ alkyl$)C(O)_{1-2}(C_0$-$C_6$ alkylene)-, $(C_0$-$C_6$ alkyl$)_2NC(O)$—, $(C_0$-$C_6$ alkyl$)OC(O)NH$—, aryl, aralkyl, heteroaryl, heteroaralkyl, halo-aryl, halo-aralkyl, halo-heteroaryl, halo-heteroaralkyl, cyano-aryl, cyano-aralkyl, cyano-heteroaryl and cyano-heteroaralkyl.

The term "halogen" (or "halo") refers to fluorine, chlorine, bromine and iodine (alternatively referred to as fluoro (F), chloro (Cl), bromo (Br), and iodo (I)).

The term "haloalkyl" means alkyl having the specified number of carbon atoms in which from one to all of the hydrogen atoms have been replaced by a halogen atom. For example, $CF_3$.

The terms "aralkyl" and "heteroaralkyl" refer to an aryl/heteroaryl linked to the rest of the molecule via a $C_1$ to $C_4$ alkylene.

The term "$C_0$" as employed in expressions such as "$C_{0-6}$ alkylene" means a direct covalent bond; or when employed in expressions such as "$C_{0-6}$ alkyl" means hydrogen. Similarly, when an integer defining the presence of a certain number of atoms in a group is equal to zero, it means that the atoms adjacent thereto are connected directly by a bond; for example, in the structure

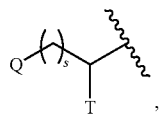

wherein s is an integer equal to zero, 1 or 2, the structure is

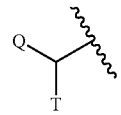

when s is zero; or it means that the indicated atom is absent; for example —$S(O)_0$— means —S—.

Unless expressly stated to the contrary, an "unsaturated" ring is a partially or fully unsaturated ring. For example, an "unsaturated monocyclic $C_6$ carbocycle" refers to cyclohexene, cyclohexadiene, and benzene.

Unless expressly stated to the contrary, all ranges cited herein are inclusive. For example, a heterocycle described as containing from "1 to 4 heteroatoms" means the heterocycle can contain 1, 2, 3 or 4 heteroatoms.

When any variable occurs more than one time in any constituent or in any formula depicting and describing compounds of the invention, its definition on each occurrence is independent of its definition at every other occurrence. Also, combinations of substituents and/or variables are permissible only if such combinations result in stable compounds. For variable definitions containing terms having repeated terms, e.g., $(CRiRj)_r$, where r is the integer 2, Ri is a defined variable, and Rj is a defined variable, the value of Ri may differ in each instance in which it occurs, and the value of Rj may differ in each instance in which it occurs. For example, if Ri and Rj are independently selected from the group consisting of methyl, ethyl, propyl and butyl, then $(CRiRj)_2$ can be

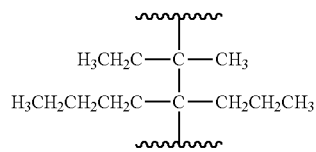

The term $(C_{1-6})$alkyl as used hereinabove means a branched or unbranched alkyl group having 1-6 carbon atoms, for example methyl, ethyl, propyl, isopropyl, butyl, tert-butyl, n-pentyl and n-hexyl. Preferred is $(C_{1-4})$alkyl.

The term $(C_{1-5})$alkyl means a branched or unbranched alkyl group having 1-5 carbon atoms, for example methyl, ethyl, propyl, isopropyl, butyl, tert-butyl and n-pentyl.

The term $(C_{1-4})$alkyl as used herein means a branched or unbranched alkyl group having 1-4 carbon atoms, being methyl, ethyl, n-propyl, isopropyl, n-butyl, isobutyl, sec-butyl and tert-butyl.

The term $(C_{1-3})$alkoxy means an alkoxy group having 1-3 carbon atoms, the alkyl moiety being branched or unbranched.

The term $(C_{1-3})$alkoxycarbonyl means an alkoxycarbonyl group having 1-3 carbon atoms in the alkoxy moiety, the alkoxy moiety having the same meaning as previously defined.

The term (di)$(C_{1-6})$alkylaminocarbonyl means an alkylaminocarbonyl group, the amino group of which is monosubstituted or disubstituted independently with an alkyl group which contains 1-6 carbon atoms and which has the same meaning as previously defined. Preferred alkyl group is $(C_{1-4})$alkyl.

The term $(C_{3-7})$cycloalkyl means a cycloalkyl group having 3-7 carbon atoms, such as cyclopropyl, cyclobutyl, cyclopentyl, cyclohexyl and cycloheptyl. 5-6 Carbon atoms are preferred.

The term (C$_{3-5}$)heterocycloalkyl means a heterocycloalkyl group having 3-5 carbon atoms, including 1-3 heteroatoms selected from N, O and/or S, which may be attached via a nitrogen if feasible, or a carbon atom. Preferred number of heteroatoms is one or two. Most preferred number is one. Preferred heteroatoms are N or O. Most preferred are piperazinyl, tetrahydropyranyl, morpholinyl and pyrrolidinyl.

A group having the formula

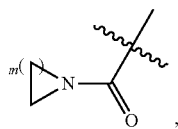

means a heterocyclocarbonyl group such as

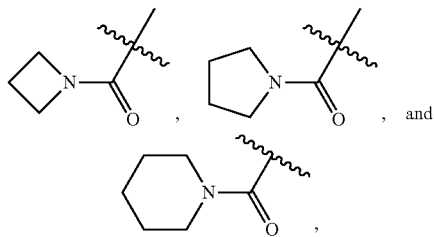

each optionally substituted with one or more (C$_{1-10}$)alkyl, halogen, amino, cyano, hydroxy, and (C$_{1-3}$)alkoxy.

The term (C$_{2-9}$)heteroaryl means an aromatic group having 2-9 carbon atoms and 1-3 heteroatoms selected from N, O and S, like imidazolyl, thiadiazolyl, pyridinyl, pyrimidinyl, thiophenyl or furyl, pyrazolyl, isoxazolyl or quinolyl. Preferred number of heteroatoms is one or two. Preferred heteroaryl groups are pyrazolyl, thiophenyl, isoxazolyl, pyridyl and quinolyl. The (C$_{2-5}$)heteroaryl group may be attached via a carbon atom or a nitrogen, if feasible.

The term (C$_{6-14}$)aryl means an aromatic hydrocarbon group having 6-14 carbon atoms, such as phenyl, naphthyl, tetrahydronaphthyl, indenyl, anthracyl, More preferred are (C$_{6-10}$)aryl groups. The most preferred aromatic hydrocarbon group is phenyl.

As used herein, the term "X$_a$—X$_b$", shall have the same meaning as the term "X$_{a-b}$", wherein X is any atom and a and b are any integers. For example, "C$_1$-C$_4$" shall have the same meaning as "C$_{1-4}$". Additionally, when referring to a functional group generically, "A$^x$" shall have the same meaning, and be interchangeable with, "AX", wherein "A" is any atom and "x" or "X" are any integer. For example, "R$^1$" shall have the same meaning, and be interchangeable with, "R1".

In the above definitions with multifunctional groups, the attachment point is at the last group. For example, the term (C$_{1-3}$)alkoxycarbonyl refers to, e.g.

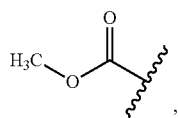

and the term (C1-4)alkylcarbonyloxy refers to, e.g.

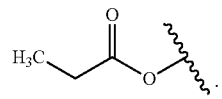

The term "substituted" means that one or more hydrogens on the designated atom/atoms is/are replaced with a selection from the indicated group, provided that the designated atom's normal valency under the existing circumstances is not exceeded, and that the substitution results in a stable compound. Combinations of substituents and/or variables are permissible only if such combinations result in stable compounds. "Stable compound" or "stable structure" is defined as a compound or structure that is sufficiently robust to survive isolation to a useful degree of purity from a reaction mixture, and formulation into an efficacious therapeutic agent. Accordingly, the term "one or more" when referring to a substituent and/or variable means that one or more hydrogens on the designated atom/atoms is/are replaced with a selection from the indicated group, provided that the designated atom's normal valency under the existing circumstances is not exceeded, and that the substitution results in a stable compound.

The term "optionally substituted" means that a substitution with the specified groups, radicals, or moieties may or may not be made on the specified group.

When, in the definition of a substituent, it is indicated that "all of the alkyl groups" of said substituent are optionally substituted, this also includes the alkyl moiety of an alkoxy group.

The use of the terms "salt", "solvate", "ester", "prodrug", and the like is intended to equally apply to the salt, solvate, ester, and prodrug of enantiomers, stereoisomers, rotamers, tautomers, positional isomers, racemates, or prodrugs of the inventive compounds.

The term "effective amount" as used herein refers to an amount of the compound of Formula (I) and/or an additional therapeutic agent, or a composition thereof, that is effective in producing the desired therapeutic, ameliorative, inhibitory or preventative effect when administered to a subject suffering from an RORgammaT-mediated disease or disorder. In the combination therapies of the present invention, as effective amount can refer to each individual agent or to the combination as a whole, wherein the amounts of all agents administered are together effective, but wherein the component agent of the combination may not be present individually in an effective amount.

A "subject" is a human or non-human mammal. In one embodiment, a subject is a human. In another embodiment, a subject is a chimpanzee.

It should be noted that any carbon as well as heteroatom with unsatisfied valences in the text, schemes, examples and tables herein is assumed to have the sufficient number of hydrogen atom(s) to satisfy the valences.

The compounds of this invention include the prodrugs, hydrates or solvates of the compounds.

Optical Isomers—Diastereomers—Geometric Isomers—Tautomers

The compounds of Formula I may contain asymmetric or chiral centers, and, therefore, exist in different stereoisomeric forms. It is intended that all stereoisomeric forms of the compounds of Formula (I) as well as mixtures thereof, including racemic mixtures, form part of the present invention. In addition, the present invention embraces all geometric and positional isomers. For example, if a compound of Formula (I) incorporates a double bond or a fused ring, both the cis- and trans-forms, as well as mixtures, are embraced within the scope of the invention.

Compounds described herein may contain an asymmetric center and may thus exist as enantiomers. Where the compounds according to the invention possess two or more asymmetric centers, they may additionally exist as diastereomers. The present invention includes all such possible stereoisomers as substantially pure resolved enantiomers, racemic mixtures thereof, as well as mixtures of diastereomers. The above Formula I is shown without a definitive stereochemistry at certain positions. The present invention includes all stereoisomers of Formula I and pharmaceutically acceptable salts thereof. Diastereoisomeric pairs of enantiomers may be separated by, for example, fractional crystallization from a suitable solvent, and the pair of enantiomers thus obtained may be separated into individual stereoisomers by conventional means, for example by the use of an optically active acid or base as a resolving agent or on a chiral HPLC column. Further, any enantiomer or diastereomer of a compound of the general Formula I may be obtained by stereospecific synthesis using optically pure starting materials or reagents of known configuration.

When compounds described herein contain olefinic double bonds, unless specified otherwise, such double bonds are meant to include both E and Z geometric isomers.

Some of the compounds described herein may exist with different points of attachment of hydrogen. Such compounds are referred to as tautomers. For example, compounds including carbonyl —$CH_2C(O)$— groups (keto forms) may undergo tautomerism to form hydroxyl —CH=C(OH)— groups (enol forms). Both keto and enol forms, individually as well as mixtures thereof, are included within the scope of the present invention.

Diastereomeric mixtures can be separated into their individual diastereomers on the basis of their physical chemical differences by methods well known to those skilled in the art, such as, for example, by chromatography and/or fractional crystallization. Enantiomers can be separated by converting the enantiomeric mixture into a diastereomeric mixture by reaction with an appropriate optically active compound (e.g. chiral auxiliary such as a chiral alcohol or Mosher's acid chloride), separating the diastereomers and converting (e.g. hydrolyzing) the individual diastereomers to the corresponding pure enantiomers. Also, some of the compounds of Formula (I) may be atropisomers (e.g. substituted biaryls) and are considered as part of this invention. Enantiomers can also be separated by use of chiral HPLC column.

It is also possible that the compounds of Formula I may exist in different tautomeric forms, and all such forms are embraced within the scope of the invention. Also, for example, all keto-enol and imine-enamine forms of the compounds are included in the invention.

All stereoisomers (for example, geometric isomers, optical isomers and the like) of the present compounds (including those of the salts, solvates, esters, and prodrugs of the compounds as well as the salts, solvates, and esters of the prodrugs), such as those that may exist due to asymmetric carbons on various substituents, including enantiomeric forms (which may exist even in the absence of asymmetric carbons), rotameric forms, atropisomers, and diastereomeric forms, are contemplated within the scope of this invention, as are positional isomers. Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the IUPAC 1974 Recommendations.

Salts

The term "pharmaceutically acceptable salts" refers to salts prepared from pharmaceutically acceptable non-toxic bases or acids. When the compound of the present invention is acidic, its corresponding salt can be conveniently prepared from pharmaceutically acceptable non-toxic bases, including inorganic bases and organic bases. Salts derived from such inorganic bases include aluminum, ammonium, calcium, copper (ic and ous), ferric, ferrous, lithium, magnesium, manganese (ic and ous), potassium, sodium, zinc and the like salts. Preferred are the ammonium, calcium, magnesium, potassium and sodium salts. Salts prepared from pharmaceutically acceptable organic non-toxic bases include salts of primary, secondary, and tertiary amines derived from both naturally occurring and synthetic sources. Pharmaceutically acceptable organic non-toxic bases from which salts can be formed include, for example, arginine, betaine, caffeine, choline, N,N'-dibenzyl-ethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, dicyclohexylamine, lysine, methylglucamine, morpholine, piperazine, piperidine, polyamine resins, procaine, purines, theobromine, triethylamine, trimethylamine, tripropylamine, tromethamine and the like.

When the compound of the present invention is basic, its corresponding salt can be conveniently prepared from pharmaceutically acceptable non-toxic inorganic and organic acids. Such acids include, for example, acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid and the like. Preferred are citric, hydrobromic, hydrochloric, maleic, phosphoric, sulfuric, and tartaric acids.

The compounds of Formula I can form salts which are also within the scope of this invention. Reference to a compound of Formula I herein is understood to include reference to salts thereof, unless otherwise indicated.

The term pharmaceutically acceptable salt represents those salts that are, within the scope of medical judgment, suitable for use in contact for the tissues of humans and lower animals without undue toxicity, irritation, allergic response and the like, and are commensurate with a reasonable benefit/risk ratio. Pharmaceutically acceptable salts are well known in the art. They may be obtained during the final isolation and purification of the compounds of the invention, or separately by reacting the free base function with a suitable mineral acid such as hydrochloric acid, phosphoric acid, or sulfuric acid, or with an organic acid such as for example ascorbic acid, citric acid, tartaric acid, lactic acid, maleic acid, malonic acid, fumaric acid, glycolic acid, succinic acid, propionic acid, acetic acid, methanesulfonic acid, and the like. The acid function can be reacted with an organic or a mineral base, like sodium hydroxide, potassium hydroxide, calcium hydroxide, calcium carbonate, ammonium (e.g. diethylamine) or lithium hydroxide.

Solvates

The present invention includes within its scope solvates of compounds of Formula I. As used herein, the term "solvate" refers to a complex of variable stoichiometry formed by a solute (i.e., a compound of Formula I) or a pharmaceutically acceptable salt thereof and a solvent that does not interfere with the biological activity of the solute. Examples of solvents include but are not limited to water, ethanol, and acetic acid. When the solvent is water, the solvate is known as hydrate; hydrate includes, but is not limited to, hemi-, mono, sesqui-, di- and trihydrates.

The compounds of the invention may form hydrates or solvates. It is known to those of skill in the art that charged compounds form hydrated species when lyophilized with water, or form solvated species when concentrated in a solution with an appropriate organic solvent. One or more compounds of the invention may exist in unsolvated as well as solvated forms with pharmaceutically acceptable solvents such as water, ethanol, and the like, and it is intended that the invention embrace both solvated and unsolvated forms. "Solvate" may also mean a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of suitable solvates include ethanolates, methanolates, and the like. "Hydrate" is a solvate wherein the solvent molecule is H$_2$O.

Prodrugs

The present invention includes within its scope the use prodrugs of the compounds of this invention. In general, such prodrugs will be functional derivatives of the compounds of this invention which are readily convertible in vivo into the required compound. Thus, in the methods of treatment of the present invention, the term "administering" shall encompass the treatment of the various conditions described with a compound of formula I or with a compound that may not be a compound of formula I, but that converts to a compound of formula I in vivo after administration to the patient. Conventional procedures for the selection and preparation of suitable prodrug derivatives are described, for example, in "Design of Prodrugs," ed. H. Bundgaard, Elsevier, 1985.

The term "prodrug" means a compound (e.g., a drug precursor) that is transformed in vivo to yield a compound of Formula I or a pharmaceutically acceptable salt, hydrate or solvate of the compound. The transformation may occur by various mechanisms (e.g., by metabolic or chemical processes), such as, for example, through hydrolysis in blood. A discussion of prodrugs and the use of prodrugs is provided by T. Higuchi and W. Stella, "Prodrugs as Novel Delivery Systems," Vol. 14 of the A.C.S. Symposium Series, 1987; and in Bioreversible Carriers in Drug Design, ed. Edward B. Roche, American Pharmaceutical Association and Pergamon Press, 1987.

Isotopes

In the compounds of generic Formula I, the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of generic Formula I. For example, different isotopic forms of hydrogen (H) include protium ($^1$H) and deuterium ($^2$H). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. In light of the present disclosure, isotopically-enriched compounds within generic Formula I can be prepared without undue experimentation by conventional techniques well known to those skilled in the art or by processes analogous to those described in the Schemes and Examples herein using appropriate isotopically-enriched reagents and/or intermediates.

Utilities

Compounds of the present invention alter the interaction of coregulator proteins with Retinoic Acid Receptor-related Orphan Receptor gamma t (RORgammaT) and thereby antagonize RORgammaT-mediated transcriptional activity, and as such are useful in the treatment of diseases and conditions in which inhibition of RORgammaT is desirable, such as autoimmune and inflammatory diseases and disorders.

Accordingly, another embodiment of the present invention provides a method for treating a disease or condition mediated by RORgammaT in a subject comprising administering to the subject an amount of a compound having Formula I, Ia, Ib, Ic, Id, Ie, If or Ig or a pharmaceutically acceptable salt or solvate thereof, that is effective for treating the disease or condition mediated by RORgammaT in the subject.

The compounds according to the invention can be used in therapy.

A further aspect of the invention resides in the use of compounds according to the invention or a pharmaceutically acceptable salt thereof for the treatment of RORgammaT-mediated diseases or RORgammaT mediated conditions.

Another aspect of the invention resides in the use of compounds or a pharmaceutically acceptable salt thereof having the general formula I for the treatment of autoimmune diseases, in particular those diseases in which Th17 cells and non-Th17 cells, which express Th17 hallmark cytokines, play a prominent role. These include, but are not limited to, the treatment of rheumatoid arthritis, psoriasis, inflammatory bowel disease, Crohn's disease, ankylosing spondylitis and multiple sclerosis.

In another aspect, compounds or a pharmaceutically acceptable salt thereof having the general formula I can be used for treatment of inflammatory diseases in which Th17 cells and/or non-Th17 cells, which express Th17 hallmark cytokines, play a prominent role, such as but not limited to respiratory diseases, osteoarthritis and asthma. Also, compounds or a pharmaceutically acceptable salt thereof having the general formula I can be used for treatment of infectious diseases in which Th17 cells and/or non-Th17 cells, which express Th17 hallmark cytokines, play a prominent role, such as but not limited to mucosal leishmaniasis.

Compounds or a pharmaceutically acceptable salt thereof having the general formula I can also be used for treatment of other diseases in which Th17 cells and/or non-Th17 cells, which express Th17 hallmark cytokines, play a prominent role, such as but not limited to Kawasaki disease and Hashimoto's thyroiditis.

In one aspect the disease or condition is an autoimmune disease or inflammatory disease. The disease or condition includes, but is not limited to, multiple sclerosis, inflammatory bowel disease, Crohn's disease, psoriasis, rheumatoid arthritis, asthma, osteoarthritis, Kawasaki disease, Hashimoto's thyroiditis or mucosal leishmaniasis.

In another aspect, the compounds according to the invention can be used in therapies to treat or prevent multiple sclerosis, inflammatory bowel disease, Crohn's disease, psoriasis, rheumatoid arthritis, asthma, osteoarthritis, Kawasaki disease, Hashimoto's thyroiditis and mucosal leishmaniasis.

In another aspect the compounds according to the invention can be used to treat or prevent psoriasis.

In yet another aspect the compounds according to the invention can be used to treat inflammatory bowel disease.

This aspect of the present invention further includes the use of a compound of Formula I, Ia, Ib, Ic, Id, Ie, If or Ig or a pharmaceutically acceptable salt or solvate thereof, in the manufacture of a medicament for the treatment of a disease or condition mediated by RORgammaT.

Route of Administration/Dosage

The compounds of this invention can be administered for the treatment or prevention of afflictions, diseases and illnesses according to the invention by any means that effects contact of the active ingredient compound with the site of action in the body of a warm-blooded animal. For example, administration can be oral, topical, including transdermal, ocular, buccal, intranasal, inhalation, intravaginal, rectal, intracisternal and parenteral. The term "parenteral" as used herein refers to modes of administration that include subcutaneous, intravenous, intramuscular, intraarticular injection or infusion, intrasternal and intraperitoneal. For the purpose of this disclosure, a warm-blooded animal is a member of the animal kingdom possessed of a homeostatic mechanism and includes mammals and birds.

The compounds can be administered by any conventional means available for use in conjunction with pharmaceuticals, either as individual therapeutic agents or in a combination of therapeutic agents. They can be administered alone, but are generally administered with a pharmaceutical carrier selected on the basis of the chosen route of administration and standard pharmaceutical practice.

The dosage administered will be dependent on the age, health and weight of the recipient, the extent of disease, kind of concurrent treatment, if any, frequency of treatment and the nature of the effect desired. Usually, a daily dosage of active ingredient compound will be from about 1.0-2000 milligrams per day. Ordinarily, from 10 to 500 milligrams per day in one or more applications is effective to obtain desired results. These dosages are the effective amounts for the treatment and prevention of afflictions, diseases and illnesses described above, e.g., autoimmune and inflammatory diseases and disorders.

Compositions include e.g. those suitable for oral, sublingual, subcutaneous, intravenous, intramuscular, nasal, local, or rectal administration, and the like, all in unit dosage forms for administration.

For oral administration, the active ingredient may be presented as discrete units, such as tablets, capsules, powders, granulates, solutions, suspensions, and the like.

For parenteral administration, the pharmaceutical composition of the invention may be presented in unit-dose or multi-dose containers, e.g. injection liquids in predetermined amounts, for example in sealed vials and ampoules, and may also be stored in a freeze dried (lyophilized) condition requiring only the addition of sterile liquid carrier, e.g. water, prior to use.

Mixed with such pharmaceutically acceptable auxiliaries, e.g. as described in the standard reference, Gennaro, A. R. et al., Remington: *The Science and Practice of Pharmacy* (20th Edition., Lippincott Williams & Wilkins, 2000, see especially Part 5: Pharmaceutical Manufacturing), the active agent may be compressed into solid dosage units, such as pills, tablets, or be processed into capsules or suppositories.

By means of pharmaceutically acceptable liquids the active agent can be applied as a fluid composition, e.g. as an injection preparation, in the form of a solution, suspension, emulsion, or as a spray, e.g. a nasal spray.

For making solid dosage units, the use of conventional additives such as fillers, colorants, polymeric binders and the like is contemplated. In general any pharmaceutically acceptable additive that does not interfere with the function of the active compounds can be used. Suitable carriers with which the active agent of the invention can be administered as solid compositions include lactose, starch, cellulose derivatives and the like, or mixtures thereof, used in suitable amounts. For parenteral administration, aqueous suspensions, isotonic saline solutions and sterile injectable solutions may be used, containing pharmaceutically acceptable dispersing agents and/or wetting agents, such as propylene glycol or butylene glycol.

Pharmaceutical Compositions

Another aspect of the present invention provides pharmaceutical compositions comprising a compound of Formula I or a pharmaceutically acceptable salt or solvate thereof and one or more pharmaceutically acceptable excipients. The term "excipient" and "carrier" may be used interchangeably. The term "composition", as in pharmaceutical composition, is intended to encompass a product comprising the active ingredient(s), and the inert ingredient(s) (pharmaceutically acceptable excipients) that make up the carrier, as well as any product that results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of Formula I, additional active ingredient(s), and pharmaceutically acceptable excipients.

The pharmaceutical compositions of the present invention comprise a compound represented by Formula I (or pharmaceutically acceptable salts thereof) as an active ingredient, a pharmaceutically acceptable carrier and optionally other therapeutic ingredients or adjuvants. The compositions include compositions suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions may be conveniently presented in unit dosage form and prepared by any of the methods well known in the art of pharmacy.

The active ingredient can be administered orally in solid dosage forms, such as capsules, tablets, troches, dragées, granules and powders, or in liquid dosage forms, such as elixirs, syrups, emulsions, dispersions, and suspensions. The active ingredient can also be administered parenterally, in sterile liquid dosage forms, such as dispersions, suspensions or solutions. Other dosages forms that can also be used to administer the active ingredient as an ointment, cream, drops, transdermal patch or powder for topical administration, as an ophthalmic solution or suspension formation, i.e., eye drops, for ocular administration, as an aerosol spray or powder composition for inhalation or intranasal administration, or as a cream, ointment, spray or suppository for rectal or vaginal administration.

Gelatin capsules contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propylparaben, and chlorobutanol.

Suitable pharmaceutical carriers are described in *Remington's Pharmaceutical Sciences*, A. Osol, a standard reference text in this field.

For administration by inhalation, the compounds of the present invention may be conveniently delivered in the form of an aerosol spray presentation from pressurized packs or nebulizers. The compounds may also be delivered as powders which may be formulated and the powder composition may be inhaled with the aid of an insufflation powder inhaler device. The preferred delivery system for inhalation is a metered dose inhalation (MDI) aerosol, which may be formulated as a suspension or solution of a compound of Formula I in suitable propellants, such as fluorocarbons or hydrocarbons.

For ocular administration, an ophthalmic preparation may be formulated with an appropriate weight percent solution or suspension of the compounds of Formula I in an appropriate ophthalmic vehicle, such that the compound is maintained in contact with the ocular surface for a sufficient time period to allow the compound to penetrate the corneal and internal regions of the eye.

Useful pharmaceutical dosage-forms for administration of the compounds of this invention include, but are not limited to, hard and soft gelatin capsules, tablets, parenteral injectables, and oral suspensions.

A large number of unit capsules are prepared by filling standard two-piece hard gelatin capsules each with 100 milligrams of powdered active ingredient, 150 milligrams of lactose, 50 milligrams of cellulose, and 6 milligrams magnesium stearate.

A mixture of active ingredient in a digestible oil such as soybean oil, cottonseed oil or olive oil is prepared and injected by means of a positive displacement pump into gelatin to form soft gelatin capsules containing 100 milligrams of the active ingredient. The capsules are washed and dried.

A large number of tablets are prepared by conventional procedures so that the dosage unit is 100 milligrams of active ingredient, 0.2 milligrams of colloidal silicon dioxide, 5 milligrams of magnesium stearate, 275 milligrams of microcrystalline cellulose, 11 milligrams of starch and 98.8 milligrams of lactose. Appropriate coatings may be applied to increase palatability or delay absorption.

A parenteral composition suitable for administration by injection is prepared by stirring 1.5% by weight of active ingredient in 10% by volume propylene glycol. The solution is made to volume with water for injection and sterilized.

An aqueous suspension is prepared for oral administration so that each 5 milliliters contain 100 milligrams of finely divided active ingredient, 100 milligrams of sodium carboxymethyl cellulose, 5 milligrams of sodium benzoate, 1.0 grams of sorbitol solution, U.S.P., and 0.025 milliliters of vanillin.

The same dosage forms can generally be used when the compounds of this invention are administered stepwise or in conjunction with another therapeutic agent. When drugs are administered in physical combination, the dosage form and administration route should be selected depending on the compatibility of the combined drugs. Thus the term coadministration is understood to include the administration of the two agents concomitantly or sequentially, or alternatively as a fixed dose combination of the two active components.

The present invention also relates to a pharmaceutical composition comprising compounds or pharmaceutically acceptable salts thereof having the general formula I in admixture with pharmaceutically acceptable auxiliaries and optionally other therapeutic agents. The auxiliaries must be "acceptable" in the sense of being compatible with the other ingredients of the composition and not deleterious to the recipients thereof.

The invention further includes a pharmaceutical composition, as hereinbefore described, in combination with packaging material suitable for said composition, said packaging material including instructions for the use of the composition for the use as hereinbefore described.

The exact dose and regimen of administration of the active ingredient, or a pharmaceutical composition thereof, may vary with the particular compound, the route of administration, and the age and condition of the individual subject to whom the medicament is to be administered.

In general parenteral administration requires lower dosages than other methods of administration which are more dependent upon absorption. However, a dosage for humans preferably contains 0.0001-100 mg per kg body weight. The desired dose may be presented as one dose or as multiple subdoses administered at appropriate intervals throughout the day. The dosage as well as the regimen of administration may differ between a female and a male recipient.

Combination Therapy

Compounds of the present invention, and their salts and solvates, and physiologically functional derivatives thereof, may be employed alone or in combination with other therapeutic agents for the treatment of diseases and conditions associated with inappropriate IL-17 pathway activity. Combination therapies according to the present invention thus comprise the administration of at least one compound of formula (I) or a pharmaceutically acceptable salt or solvate thereof, or a physiologically functional derivative thereof, and the use of at least one other pharmaceutically active agent. The compound(s) of formula (I) and the other pharmaceutically active agent(s) may be administered together or separately and, when administered separately this may occur simultaneously or sequentially in any order. The amounts of the compound(s) of formula (I) and the other pharmaceutically active agent(s) and the relative timings of administration will be selected in order to achieve the desired combined therapeutic effect. For the treatment of the inflammatory and autoimmune diseases, rheumatoid arthritis, psoriasis, inflammatory bowel disease, ankylosing spondylitis, SLE, uveitis, atopic dermatitis, COPD, asthma and allergic rhinitis a compound of formula (I) may be combined with one or more other active agents such as: (1) TNF-a inhibitors; (2) non-selective COX-I/COX-2 inhibitors; (3) COX-2 inhibitors; (4) other agents for treatment of inflammatory and autoimmune diseases including glucocorticoids, methotrexate, leflunomide, sulfasalazine, azathioprine, cyclosporin, tacrolimus, penicillamine, bucillamine, actarit, mizoribine, lobenzarit, ciclesonide, hydroxychloroquine, d-penicillamine, aurothiomalate, auranofin or parenteral or oral gold, cyclophosphamide, Lymphostat-B, BAFF/APRIL inhibitors and CTLA-4-Ig or mimetics thereof; (5) leukotriene biosynthesis inhibitor, 5-lipoxygenase (5-LO) inhibitor or 5-lipoxygenase activating protein (FLAP) antagonist; (6) LTD4 receptor antagonist; (7) PDE4 inhibitor; (8) antihistamine HI receptor antagonists; (9) a1- and a2-adrenoceptor agonist; (10) anticholinergic agents; (11) β-adrenoceptor agonists; (12) insulin-like growth factor type I (IGF-1) mimetic; (13) glucocorticosteroids; (14) kinase inhibitors such as inhibitors of the Janus Kinases (JAK 1 and/or JAK2 and/or JAK 3 and/or TYK2), p38 MAPK and IKK2; (15) B-cell targeting biologies such as rituximab; (16) selective costimulation modulators such as abatacept; (17) interleukin inhibitors, such as IL-1 inhibitor anakinra, IL-6 inhibitor tocilizumab, and IL12/IL-23 inhibitor ustekinumab. It could also be combined with anti-IL17 antibodies to obtain additive/synergistic responses for the treatment of inflammatory and autoimmune diseases.

It will be clear to a person skilled in the art that, where appropriate, the other therapeutic ingredient(s) may be used in the form of salts, for example as alkali metal or amine salts or as acid addition salts, or prodrugs, or as esters, for example lower alkyl esters, or as solvates, for example hydrates, to optimize the activity and/or stability and/or physical characteristics, such as solubility, of the therapeutic ingredient. It will be clear also that, where appropriate, the therapeutic ingredients may be used in optically pure form.

The combinations referred to above may conveniently be presented for use in the form of a pharmaceutical composition and thus pharmaceutical compositions comprising a combination as defined above together with a pharmaceutically acceptable diluent or carrier represent a further aspect of the invention. These combinations are of particular interest in respiratory diseases and are conveniently adapted for inhaled or intranasal delivery.

The individual compounds of such combinations may be administered either sequentially or simultaneously in separate or combined pharmaceutical compositions. Preferably, the individual compounds will be administered simultaneously in a combined pharmaceutical composition. Appropriate doses of known therapeutic agents will be readily appreciated by those skilled in the art.

Accordingly, the pharmaceutical compositions of the present invention include those that also comprise at least one additional therapeutically active agent, in addition to the compound of Formula I, Ia, Ib, Ic, Id, Ie, If or Ig.

The invention further includes a compound of Formula I in combination with one or more other drug(s).

Methods of Synthesis

Methods for preparing the compounds of this invention are illustrated in the following schemes and examples. Other synthetic protocols will be readily apparent to those skilled in the art in light of the present disclosure. The examples illustrate the preparation of the compounds of Formula I and as such are not to be considered as limiting the invention set forth in the claims appended hereto. Unless otherwise indicated, all variables are as previously defined.

All the end products of the formula I were analyzed by NMR and/or LCMS. Intermediates were analyzed by NMR and/or TLC and/or LCMS. Most compounds were purified by reverse phase HPLC, MPLC on silica gel, recrystallization and/or swish (suspension in a solvent followed by filtration of the solid). The course of the reactions was followed by thin layer chromatography (TLC) and/or LCMS and/or NMR and reaction times are given for illustration only.

Abbreviations used herein are as follows: EtOAc: Ethyl acetate; PE: Petroleum ether; EA: Ethyl acetate; DCM: Dichloromethane; AcOH: Acetic acid; DMAC: N,N-Dimethylacetamide; DMAP: 4-Dimethylaminopyridine; TEA: Triethylamine; TFA: Trifluoroacetic acid; MeOH: Methanol; bippyphos: 5-(Di-t-butylphosphino)-1',3',5'-triphenyl-1,4'-bi-1H-pyrazole; $Pd_2(dba)_3$: Tris(dibenzylideneacetone)dipalladium(0).

Scheme 1 illustrates a general method toward the preparation of compounds of formula I. Starting from halide A, N-acylation with either carboxylic acids or acid chloride in the presence of base led to the formation of compound B. Reacting halide B with appropriate primary or secondary amine in the presence of appropriate base and/or appropriate metal catalyst furnished the desired product directly. For those substrates containing an ester moiety, additional step of ester hydrolysis gave the final compound I.

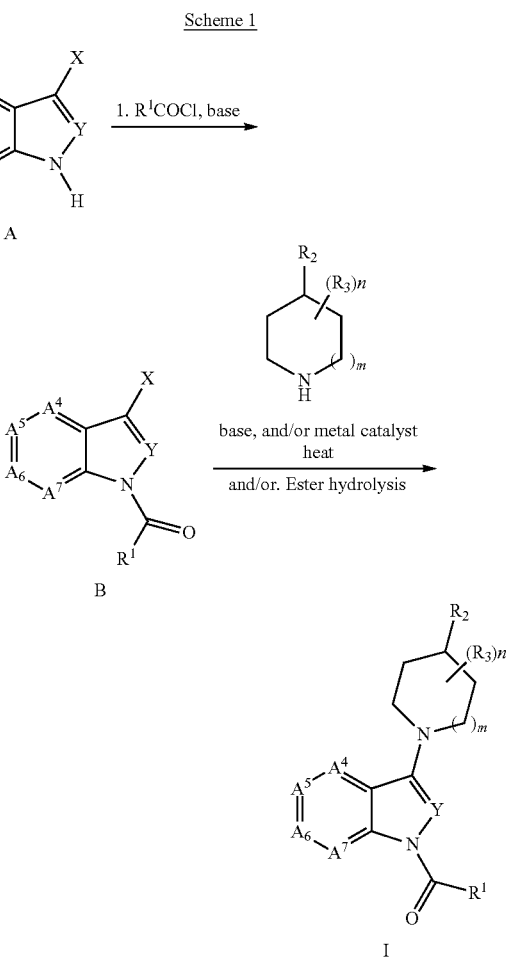

Scheme 2 illustrates an alternative route for the preparation of compounds of formula I. Starting from halide A, THP protection first followed by N-arylation led to the formation of intermediate D. Removal of THP afforded a highly useful intermediate which allowed for the rapid installation of various acylation group. Final hydrolysis gave the final product I.

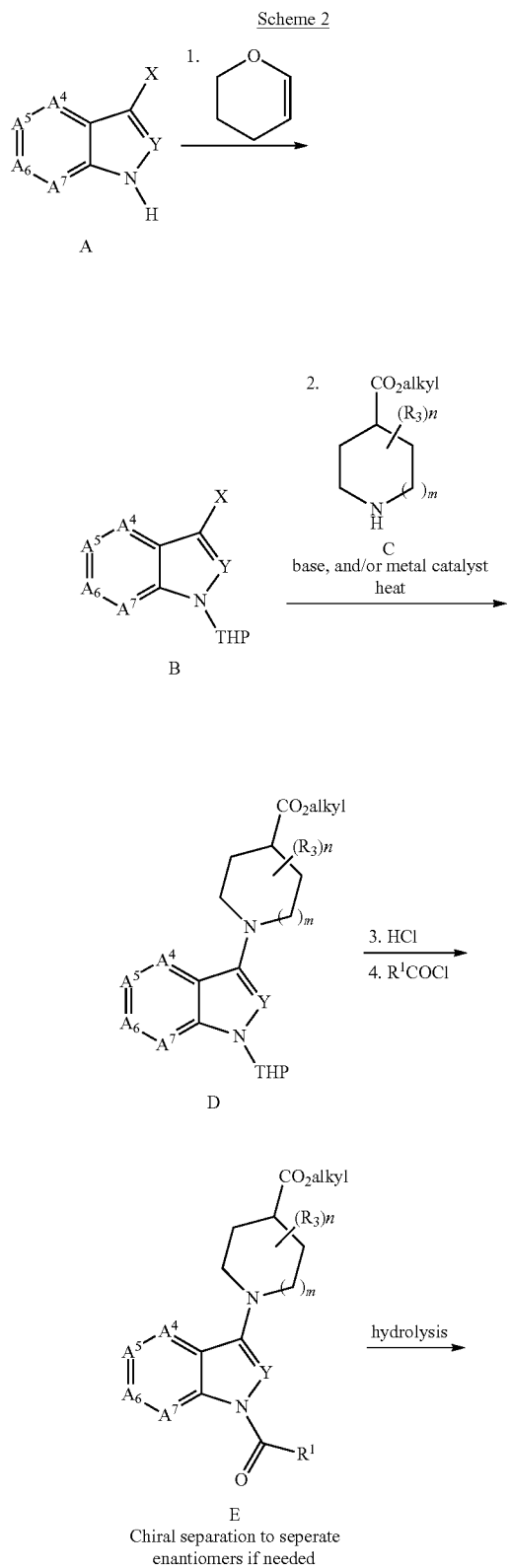

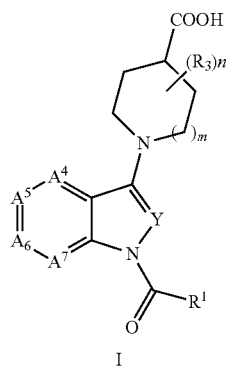

Scheme 3 illustrates a general method for the preparation of compounds of formula I that contain an amide moiety at $A^6$ position. Starting from halide A, acylation followed by N-arylation gave intermediate C. Subsequent hydrolysis, amide coupling and deprotection led to the formation of the final product I.

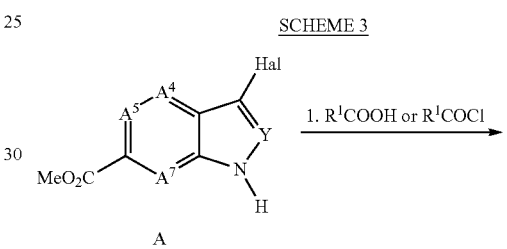

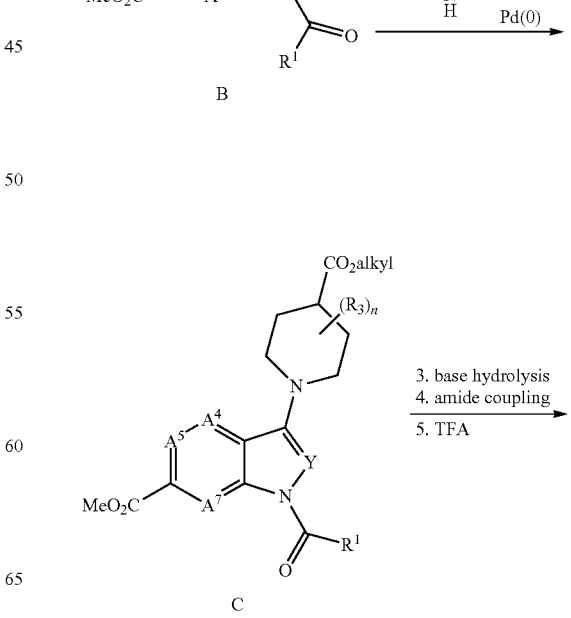

-continued

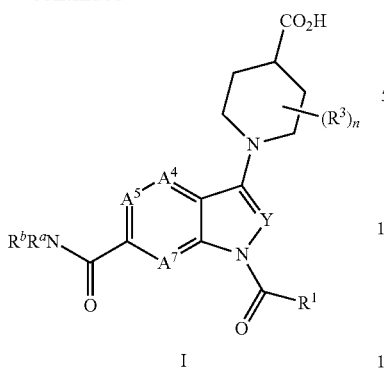

I

Commercially Available/Previously Described Materials

The following table lists commercial sources, and previously disclosed synthetic routes for chemical materials employed in the synthesis of intermediates and that can be used in the synthesis of examples of the instant invention. The list is not intended to be exhaustive, exclusive, or limiting in any way.

| Structure | Source |
|---|---|
| 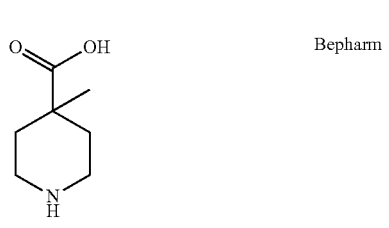 | Oakwood |
| 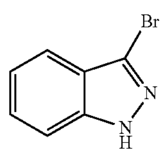 | Aldrich |
| 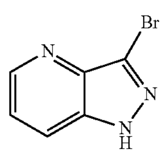 | Frontier |
|  | Alfa |
|  | Alfa |

-continued

| Structure | Source |
|---|---|
| 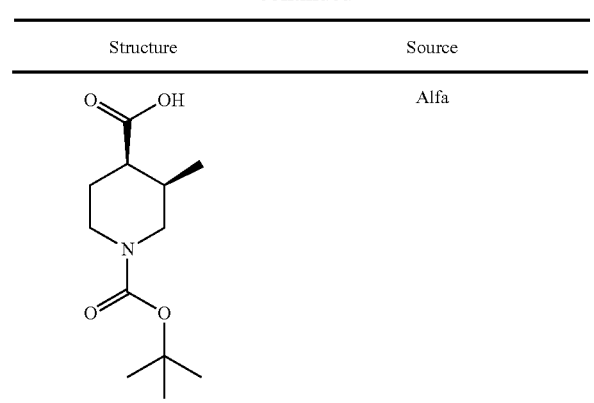 | Alfa |
|  | Bepharm |
| 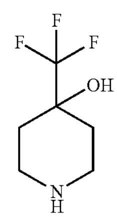 | Astatech |
| 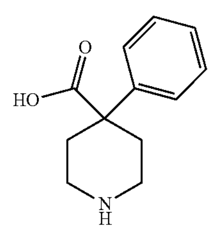 [SMILES: O=C(O)C1(c2ccccc2)CCNCC1] | BetaPharma |
|  | Alfa |
|  | Bepharm |

31
-continued

| Structure | Source |
|---|---|
| (piperidin-4-yl)acetic acid | BetaPharma |
| ethyl 1-benzyl-3-oxopiperidine-4-carboxylate | PharmaBridge |
| 1,2,3,6-tetrahydropyridine-4-carboxylic acid | LabPartner |
| methyl 8-azabicyclo[3.2.1]octane-3-carboxylate · HCl | Pharmablock |
| 4-fluoropiperidine-4-carboxylic acid | LabPartner |
| 3-fluoropiperidine-4-carboxylic acid | LabPartner |
| methyl 8-azabicyclo[3.2.1]octane-3-carboxylate (CO₂Me) | Synthonix |

32
-continued

| Structure | Source |
|---|---|
| methyl 3-azabicyclo[3.3.1]nonane-7-carboxylate | Synthonix |
| methyl 4-hydroxypiperidine-4-carboxylate | Princeton |
| methyl 2-ethylpiperidine-4-carboxylate | Journal of Medicinal Chemistry, 2010, 53, pp 7682-7698 |
| ethyl 1-benzyl-3-hydroxypiperidine-4-carboxylate | Tetrahedron Asymmetry, 2006, pp. 2015-2020 |

Intermediates

Example i-1

Preparation of (3-bromo-1H-pyrazolo[4,3-b]pyridin-1-yl)(2-chloro-6-(trifluoromethyl)phenyl)methanone Scheme i-1

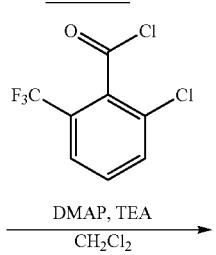

i-1a

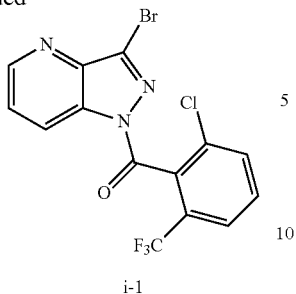

i-1

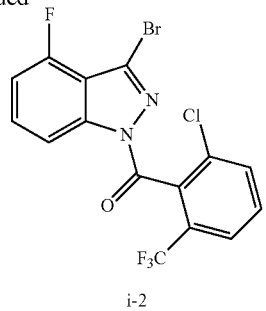

i-2

Step 1. Preparation of (3-bromo-1H-pyrazolo[4,3-b]pyridin-1-yl)(2-chloro-6-(trifluoromethyl)phenyl)methanone (i-1)

To a flask was added 3-bromo-1H-pyrazolo[4,3-b]pyridine (i-1a) (3.2 g, 16.2 mmol), 2-chloro-6-(trifluoromethyl)benzoyl chloride 2 (3.9 g, 16.2 mmol), DMAP (1.97 g, 16.2 mmol) and DCM (60 mL), followed by the addition of TEA (3.26 g, 32.4 mmol) slowly. The reaction mixture was stirred at 40° C. for 3 h. The mixture was diluted with H$_2$O, and the organic layer was separated. The aqueous layer was extracted with CH$_2$Cl$_2$. The combined organics were washed with H$_2$O, brine, dried over Na$_2$SO$_4$, and concentrated. The residue was purified by flash chromatography (Petroleum/EtOAc, 5/1) to afford 3.0 g (46%) of the title compound. LCMS (ESI) calc'd for C$_{14}$H$_6$BrClF$_3$N$_3$O [M+H]$^+$: 406. found: 406.

Example i-2

Preparation of (3-bromo-4-fluoro-1H-indazol-1-yl)(2-chloro-6-(trifluoromethyl)phenyl)methanone Scheme i-2

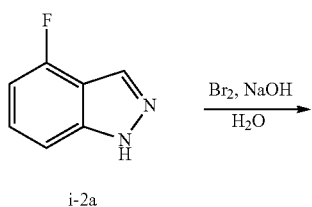

Step 1. Preparation of 3-bromo-4-fluoro-1H-indazole (i-2b)

To a suspension of 4-fluoro-1H-indazole (i-2a) (5 g, 36.8 mmol) in 2M sodium hydroxide solution (100 ml) at room temperature was added a solution of bromine (5.8 g, 36.8 mmol) in 2M sodium hydroxide solution (60 ml). The reaction mixture was stirred at room temperature for 3 hr. To the reaction mixture was added sodium bisulfite aqueous solution (10%, 100 mL). The solution was extracted with ethyl acetate (2×150 mL). The combined organic layer was washed with H$_2$O (3×100 mL) and brine (2×150 mL). The solution was dried over anhydrous Na$_2$SO$_4$ and evaporated. 5.47 g product was obtained. Yield 69%. LCMS (ESI) calc'd for C$_7$H$_4$BrFN$_2$ [M+H]$^+$: 215. found: 215.

Step 2 Preparation of (3-bromo-4-fluoro-1H-indazol-1-yl)(2-chloro-6-(trifluoromethyl)phenyl)methanone (i-2)

To a flask was added 3-bromo-4-fluoro-1H-indazole i-2b (3.2 g, 14.9 mmol), 2-chloro-6-(trifluoromethyl)benzoyl chloride (5.43 g, 22.35 mmol), DMAP (1.82 g, 14.9 mmol), TEA (3.02 g, 29.8 mmol), and the mixture was stirred at 40° C. for 3 h. The mixture was diluted with H$_2$O, and the organic layer was separated. The aqueous layer was extracted with CH$_2$Cl$_2$. The combined organics were washed with H$_2$O, brine, dried over Na$_2$SO$_4$, and concentrated. The residue was purified by flash chromatography (Petroleum/EtOAc, 5/1) to afford 2.8 g (45%) of the title compound. LCMS (ESI) calc'd for C$_{15}$H$_6$BrClF$_4$N$_2$O [M+H]$^+$: 421. found: 421.

Example i-3

Preparation of (3R,4R) and (3S,4S)-3-methylpiperidine-4-carboxylic acid

Scheme i-3

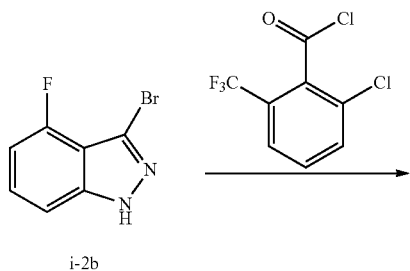

Step 1. Preparation of (3R,4R) and (3S,4S)-3-methylpiperidine-4-carboxylic acid (i-3)

To a solution of (3R,4R)-1-(tert-butoxycarbonyl)-3-methylpiperidine-4-carboxylic acid (i-3a) (350 mg, 1.44 mmol) in DCM (5 mL) was added TFA (1 ml), and the mixture was stirred at room temperature for 2 h. Then the mixture was evaporated to obtain 520 mg of the TFA salt of the compound 2. LCMS (ESI): calc'd for $C_7H_{13}NO_2$ [M+H]$^+$: 144. found: 144.

Example i-4

Preparation of methyl 3-hydroxypiperidine-4-carboxylate

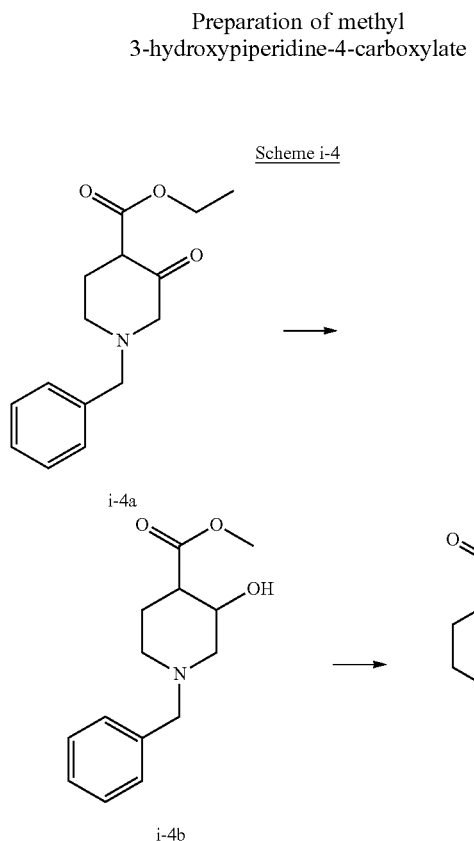

Step 1. Preparation of methyl 1-benzyl-3-hydroxypiperidine-4-carboxylate (i-4b)

A mixture of ethyl 1-benzyl-3-oxopiperidine-4-carboxylate (i-4a) (1.0 g, 3.36 mmol), $ZnCl_2$ (0.46 g, 3.36 mmol) and $NaBH_4$ (0.13 g, 3.36 mmol) in MeOH (20 mL) was stirred at 70° C. overnight. The solvent was removed under reduced pressure and the residue was diluted with $H_2O$ (50 mL). The aqueous layer was extracted with ethyl acetate (3×50 mL). The combined organic layers were washed with brine (50 mL), dried over anhydrous $Na_2SO_4$ and concentrated to obtain the desired product as pale yellow oil. LCMS (ESI) calc'd for $C_{14}H_{19}NO_3$ [M+H]$^+$: 250. found: 250.

Step 2. Preparation of methyl 3-hydroxypiperidine-4-carboxylate (i-4)

A mixture of methyl 1-benzyl-3-hydroxypiperidine-4-carboxylate (i-4b) (0.5 g, 2.01 mmol), Pd/C (10%, 50 mg) in MeOH (20 mL) was stirred at room temperature under $H_2$ balloon pressure overnight. The solvent was removed under reduced pressure to obtain the desired product as pale yellow oil. LCMS (ESI) calc'd for $C_7H_{13}NO_3$ [M+H]$^+$: 160. found: 160.

Example i-5

Preparation of ethyl 3-hydroxypiperidine-4-carboxylate

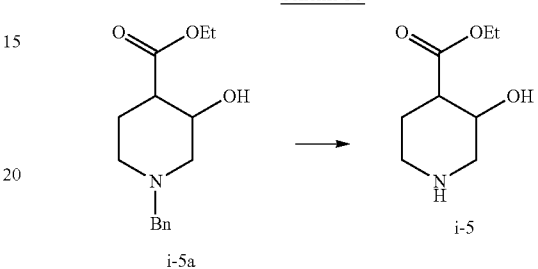

To a flask containing a solution of ethyl 1-benzyl-3-hydroxypiperidine-4-carboxylate (0.52 g, 1.98 mmol, mixture of cis and trans isomers) in ethanol (10 ml) was added palladium hydroxide on carbon (0.07 g, 0.1 mmol). The mixture was stirred at room temperature for 14 h with a hydrogen balloon, filtered through a Celite and rinsed with EtOAc. The filtrate was concentrated and NMR showed incomplete de-benzylation. This material was used for the next step without purification.

Example i-6

Preparation of ethyl 2-((3R,4R and 3S,4S)-3-hydroxy-4-methylpiperidin-4-yl)-2-oxoacetate and ethyl 2-((3S,4R and 3R,4S)-3-hydroxy-4-methylpiperidin-4-yl)-2-oxoacetate

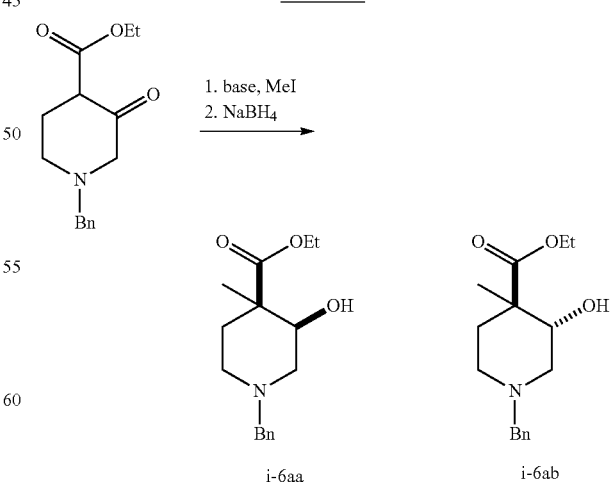

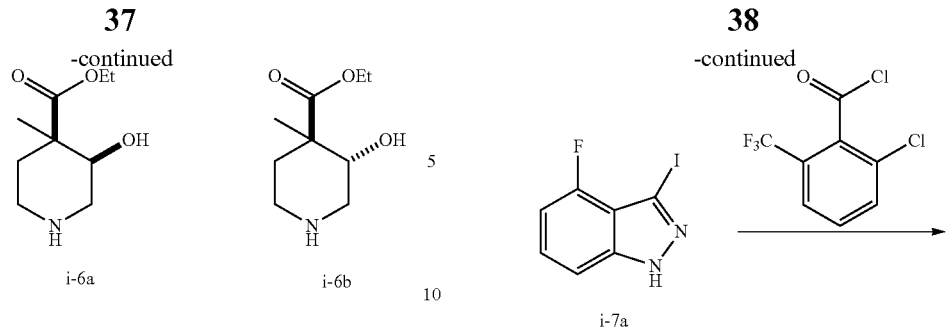

i-6a     i-6b            i-7a

Step 1. Preparation of (cis)-ethyl 1-benzyl-3-hydroxy-4-methylpiperidine-4-carboxylate (i-6aa) and (trans)-ethyl 1-benzyl-3-hydroxy-4-methylpiperidine-4-carboxylate (i-6ab)

To a suspension of KOtBu (2.49 g, 22.2 mmol) in THF (50 ml) at 0° C. was added ethyl 1-benzyl-3-oxo-4-piperidinecarboxylate hydrochloride (3.0 g, 10.1 mmol) portionwise. The mixture was stirred at room temperature for 1 h, then cooled to 0° C. MeI was added dropwise. The mixture was stirred at room temperature for 2 h. The mixture was diluted with EtOH (25 ml), cooled to 0° C., followed by adding NaBH$_4$ (0.42 g, 11.1 mmol) portionwise. After addition, the mixture was kept stirring for an additional 1 h, then was poured slowly into a beaker containing sat. NH$_4$Cl. The mixture was extracted with EtOAc. The combined organics were separated, washed with brine, dried over MgSO$_4$, and concentrated. The residue was purified by flash chromatography (10-50% EtOAc/hexanes) to afford pure cis and trans isomers: i-6aa Cis-isomer, bottom spot, 220 mg; i-6ab Trans-isomer, top spot, 540 mg; LCMS (ESI) calc'd for C$_{16}$H$_{23}$NO$_3$ [M+H]$^+$: 278. found: 278.

Step 2. Preparation of ethyl 2-((3R,4R and 3S,4S)-3-hydroxy-4-methylpiperidin-4-yl)-2-oxoacetate (i-6a) and ethyl 2-((3S,4R and 3R,4S)-3-hydroxy-4-methylpiperidin-4-yl)-2-oxoacetate (i-6b)

To a flask containing (cis)-ethyl 1-benzyl-3-hydroxy-4-methylpiperidine-4-carboxylate (i-6aa) (200 mg, 0.72 mmol,) in EtOH (2.4 ml) was added palladium hydroxide on carbon (50.6 mg, 0.072 mmol). The mixture was hydrogenated with a H$_2$ balloon at room temperature for 14 h. TLC showed no starting material left. The mixture was filtered through celite and concentrated to give crude (i-6a), which was used for the next step without purification.

The corresponding trans isomer i-6b was prepared similarly, as can be achieved by those of ordinary skill in the art of organic synthesis in light of the present disclosure, and was used directly for the next step.

Example i-7

Preparation of (2-chloro-6-(trifluoromethyl)phenyl)(4-fluoro-3-iodo-1H-indazol-1-yl)methanone Scheme i-7

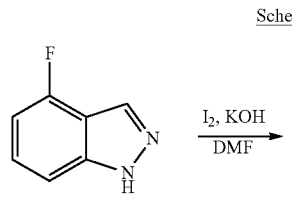

Step 1. Preparation of 4-fluoro-3-iodo-1H-indazole (i-7a)

To a solution of 4-fluoro-1H-indazole (24 g, 180 mmol) in 300 mL of DMF was added diiodine (56 g, 216 mmol) and potassium hydroxide (40 g, 720 mmol) at 0° C. The resultant mixture was allowed to warm to room temperature and stirred for 5 hours. The reaction mixture was slowly quenched with saturated sodium thiosulfate (200 mL) and extracted with EA (500 mL*3), and the combined organic layers were washed, dried and concentrated. The residue was purified by re-crystallization to afford the title compound (30 g, yield: 65%). LCMS (ESI) calc'd for C$_7$H$_4$FIN$_2$ [M+H]$^+$: 263. found: 263.

Step 2. Preparation of (2-chloro-6-(trifluoromethyl)phenyl)(4-fluoro-3-iodo-1H-indazol-1-yl)methanone (i-7)

To a suspension of NaH (106 mg, 2.64 mmol, 60% in mineral) in dry THF (30 mL) at 0° C. was added 4-fluoro-3-iodo-1H-indazole (i-7a) (460 mg, 1.76 mmol). After stirring this at 0° C. for 1 h, 2-chloro-6-(trifluoromethyl) benzoyl chloride (510 mg, 2.11 mmol) was added dropwise. The mixture was stirred at 15° C. for 2 h. The resulting mixture was quenched with water (10 mL) and concentrated in vacuum to remove THF. The residue was partitioned between ethyl acetate (100 mL) and water (100 mL). The aqueous solution was extracted with ethyl acetate (50 mL*3), and the combined organic layers were dried over anhydrous Na$_2$SO$_4$, and concentrated under reduced pressure to give crude product i-7 (800 mg, crude) as a yellow solid. LCMS (ESI) calc'd for C$_{15}$H$_6$ClF$_4$IN$_2$O [M+H]$^+$: 469. found: 469.

Example i-8

(4-chloro-3-iodo-1H-indazol-1-yl)(2-chloro-6-(trifluoromethyl)phenyl)methanone Scheme i-8

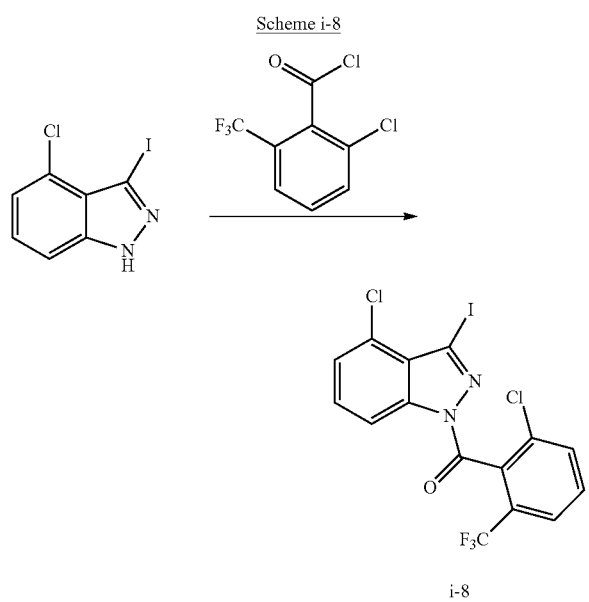

To a flask was added 4-chloro-3-iodo-1H-indazole (1 g, 3.59 mmol), 2-chloro-6-(trifluoromethyl)benzoyl chloride (1.05 g, 4.31 mmol), DMAP (0.44 g, 3.6 mmol), DCM (7.2 ml) and Et$_3$N (0.75 ml, 5.4 mmol) slowly. The reaction was allowed to stir at room temperature overnight. The mixture was diluted with ethyl acetate, washed 2× with aqueous sodium hydrogen carbonate and 1× with brine. Aqueous layers were back extracted once with ethyl acetate, combined organic layers were dried With Na$_2$SO$_4$, filtered and the solvent was evaporated under reduced pressure. The residue was purified by flash chromatography (EtOAc/Hexane 0-50%) to give the desired product as a colorless solid (1.5 g, 86%). LCMS (ESI) calc'd for C$_{15}$H$_6$Cl$_2$F$_3$IN$_2$O [M+H]$^+$: 484.8. found: 484.8.

Example i-9

Preparation of 2-chloro-6-cyclopropylbenzoic acid

Scheme i-9

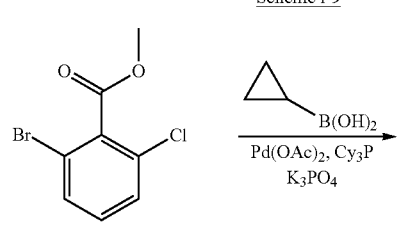

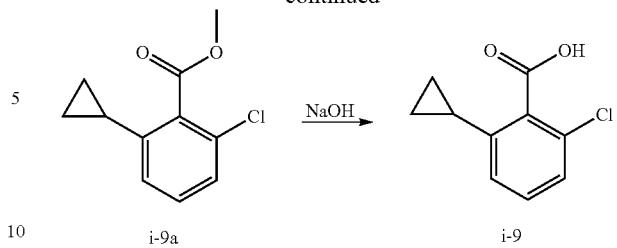

Step 1. Preparation of methyl 2-chloro-6-cyclopropylbenzoate (i-9a)

Methyl 2-bromo-6-chlorobenzoate (1.0 g, 4.0 mmol), cyclopropylboronic acid (516 mg, 6.0 mmol), Pd(OAc)$_2$ (90 mg, 0.4 mmol), Cy$_3$P (224 mg, 0.8 mmol) and K$_3$PO$_4$ (2.5 g, 12.0 mmol) were mixed in toluene (20 ml) and H$_2$O (2.5 ml). The mixture was stirred at 100° C. for 14 h under N$_2$ atmosphere. The mixture was cooled down and poured into water (50 ml). The mixture was extracted with EtOAc (50 ml). The organic layer was dried over Na$_2$SO$_4$ and concentrated. The residue was purified by flash chromatography (Petroleum/EtOAc 15/1) to give 0.6 g (71%) of the title compound. LCMS (ESI) calc'd for C$_{11}$H$_{11}$ClO$_2$ [M+H]$^+$: 211. found: 211.

Step 2. Preparation of 2-chloro-6-cyclopropylbenzoic acid (i-9)

NaOH (380 mg, 9.5 mmol) was added to a solution of methyl 2-chloro-6-cyclopropylbenzoate (i-9a) (200 mg, 0.95 mmol) in EtOH (15 ml) and H$_2$O (6 ml). The resulting solution was stirred at 80° C. overnight. The mixture was cooled down and acidified with diluted HCl to pH=2-3. Then the mixture was extracted with EtOAc (50 ml). The organic layer was dried over Na$_2$SO$_4$ and concentrated to afford 160 mg (86%) of the title compound. LCMS (ESI) calc'd for C$_{10}$H$_9$ClO$_2$ [M+H]$^+$: 197. found: 197.

Example i-10

Preparation of (2-chloro-6-cyclopropylphenyl)(4-fluoro-3-iodo-1H-indazol-1-yl)methanone Scheme i-10

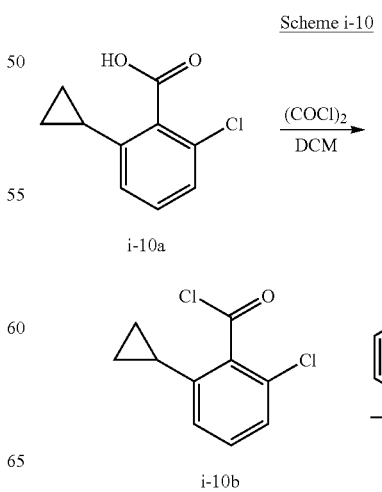

-continued

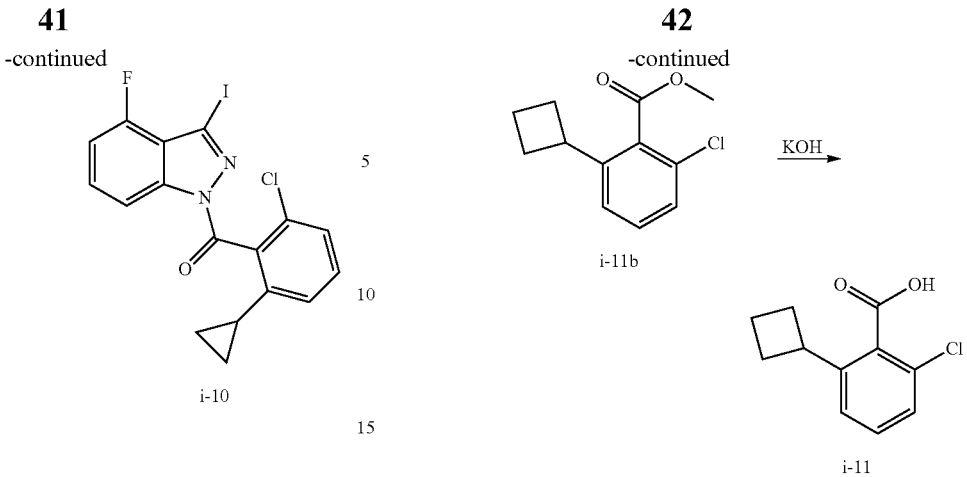

i-10

Step 1. Preparation of 2-chloro-6-cyclopropylbenzoyl chloride (i-10b)

To a solution of 2-chloro-6-cyclopropylbenzoic acid (i-10a) (1 g, 7.19 mmol) in 50 mL of DCM was added oxalyl dichloride (13 mL) at 0° C. dropwise, and then the mixture was stirred at 25° C. for 12 h. The mixture was evaporated to dryness. Then the residue was distilled under reduced pressure to afford 12 g (86%) of the title compound as yellow oil. LCMS (ESI) calc'd for $C_{10}H_8Cl_2O$ [M+H]$^+$: 215. found: 215.

Step 2. Preparation of (2-chloro-6-cyclopropylphenyl)(4-fluoro-3-iodo-1H-indazol-1-yl)methanone (i-10)

To a suspension of 4-fluoro-3-iodo-1H-indazole (1.14 g, 4.65 mmol) in 20 mL of THF was added NaH (279 mg, 6.9 mmol) dropwise at 0° C. The mixture was stirred at 0° C. for 30 mins. A solution of 2-chloro-6-cyclopropylbenzoyl chloride (i-10b) (1 g, 4.65 mmol) in anhydrous THF (20 mL) was added to the mixture dropwise. The mixture was stirred at 25° C. for another 30 mins. Then the reaction mixture was quenched by sat. NH$_4$Cl solution, diluted with water (100 mL) and extracted with EtOAc (150 mL*3). The combined organic layers were washed with brine (50 mL*2), dried over Na$_2$SO$_4$ and evaporated to dryness. The residue was purified by column chromatography on silica gel (PE:EtOAc=5:1) to give 1.7 g (86%) of the title compound as a yellow solid. LCMS (ESI) calc'd for $C_{17}H_{11}ClFIN_2O$ [M+H]$^+$: 441. found: 441.

Example i-11

Preparation of 2-chloro-6-cyclobutylbenzoic acid

Scheme i-11

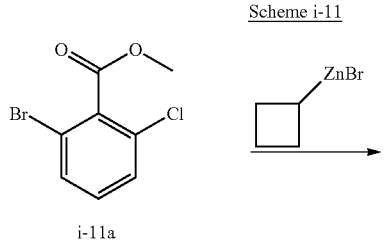

i-11a

-continued i-11b i-11

Step 1. Preparation of methyl 2-chloro-6-cyclobutylbenzoate (i-11b)

A mixture of methyl 2-bromo-6-chlorobenzoate (i-11a) (750 mg, 3 mmol), (PPh$_3$)$_4$Pd (345 mg, 0.3 mmol) and cyclobutylzinc bromide (12 ml in THF, 6 mmol) were mixed under N$_2$ protection. The mixture was stirred at 70° C. for 12 h under N$_2$. The mixture was extracted with EtOAc and water. The organic phase was washed with brine, dried over Na$_2$SO$_4$, filtered, concentrated, and purified with chromatography (PE:EtOAc=50:1) to give 350 mg (61% in LCMS, contained some PPh$_3$) of the title compound. LCMS (ESI) calc'd for $C_{12}H_{13}ClO_2$ [M+H]$^+$: 225. found: 225.

Step 2. Preparation of 2-chloro-6-cyclobutylbenzoic acid (i-11)

To a solution of methyl 2-chloro-6-cyclobutylbenzoate (i-11b) (350 mg, 1 mmol) in EtOH (2 ml), was added KOH (2M in H$_2$O, 1.5 ml, 3 mmol). The mixture was stirred at 100° C. for 12 h, acidified with 3N HCl and extracted with EtOAc. The organic phase was washed with brine, dried over Na$_2$SO$_4$, filtered and concentrated. Purification with prep-HPLC (ACN: H$_2$O) gave 125 mg of the title compound. LCMS (ESI) calc'd for $C_{11}H_{11}ClO_2$ [M+H]$^+$: 211. found: 211.

Example i-12

Preparation of (2-chloro-6-(trifluoromethyl)phenyl)(4-fluoro-3-bromo-1H-indazol-1-yl)methanone Scheme i-12

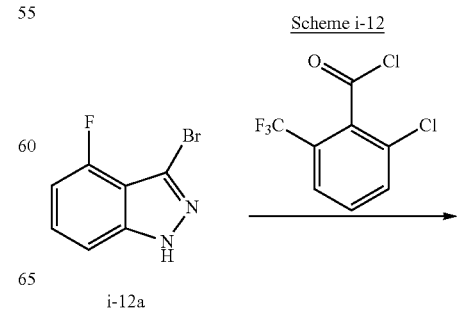

i-12a

43

-continued

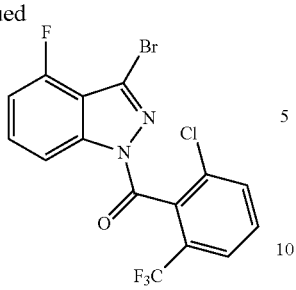

i-12

To a vial was added 3-bromo-4-fluoro-1H-indazole (i-12a) (400 mg, 1.860 mmol), TEA (389 μl, 2.79 mmol), DMAP (45.5 mg, 0.372 mmol), DCM (3.7 ml), and 2-chloro-6-(trifluoromethyl)benzoyl chloride (542 mg, 2.23 mmol) and the resulting solution was allowed to stir overnight at room temperature. The mixture was diluted with ethyl acetate, washed 2× with aqueous sodium hydrogen carbonate and 1× with brine. Aqueous layers were back extracted once with ethyl acetate, combined organic layers were dried with $Na_2SO_4$, filtered and the solvent was evaporated under reduced pressure. The residue was purified by flash chromatography (EtOAc/Hexane 10-75%) to give the desired product as a yellow solid. (326 mg, 88%) LCMS (ESI) calc'd for $C_{15}H_6BrClF_4N_2O$ [M+H]$^+$: 420.9. found: 420.9.

Example i-13

Preparation of methyl 2-methylpiperidine-4-carboxylate

Scheme i-13

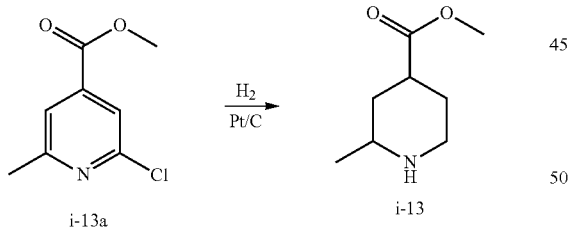

To a solution of methyl 2-chloro-6-methylisonicotinate (i-13a) (4.4 g, 23.7 mmol) in AcOH (50 mL) was added Pt/C (4 g, Pt 5% wt) under argon. The suspension was degassed under vacuum and purged with $H_2$ several times. The mixture was stirred at 70° C. overnight under $H_2$ atmosphere (50 psi). After filtration and concentrated in vacuo, 20 mL $H_2O$ was added to the mixture, and the mixture was adjusted to pH=7 with aq. $Na_2CO_3$, extracted with DCM (30 mL*3). The combined organics were concentrated in vacuo to give the crude product of the title compound (3 g, yield: 80%), which was used for the next step without further purification. LCMS (ESI) calc'd for $C_8H_{15}NO_2$ [M+H]$^+$: 158. found: 158.

44

Example i-14

3-(4-(tert-butoxycarbonyl)piperidin-1-yl)-1-(2-chloro-6-(trifluoromethyl)benzoyl)-1H-indazole-6-carboxylic acid Scheme i-14

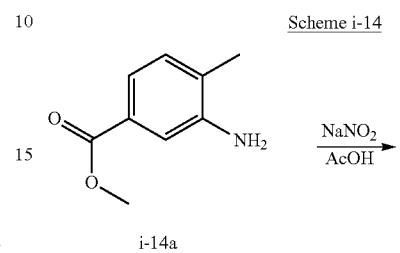

i-14a

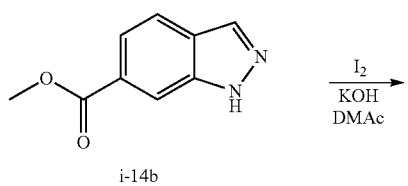

i-14b

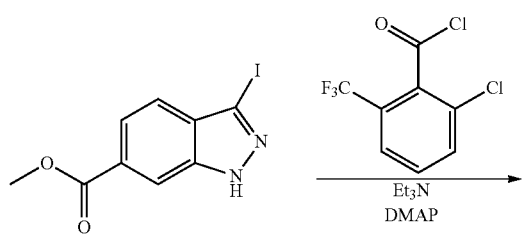

i-14c

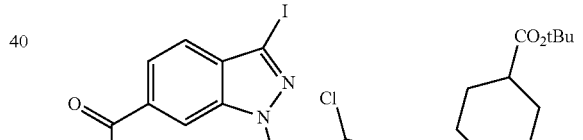

i-14d

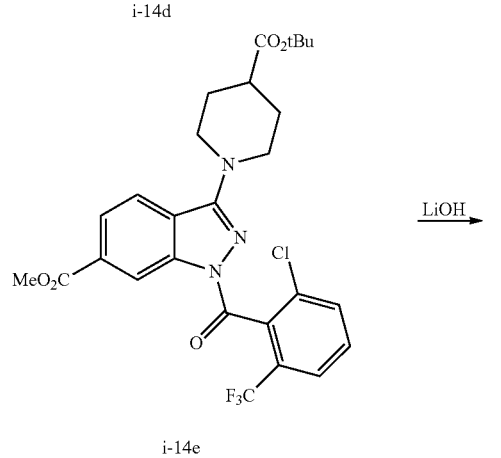

i-14e

-continued

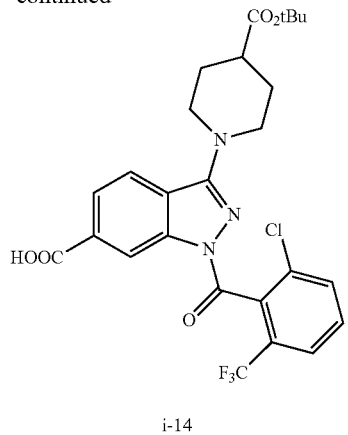

i-14

Step 1. Preparation of methyl 1H-indazole-6-carboxylate (i-14b)

Methyl 3-amino-4-methylbenzoate (i-14a) (5.0 g, 30.2 mmol) was dissolved in AcOH (140 mL). Sodium nitrite (2.1 g, 30.2 mmol) in water (3.5 mL) was added dropwise to the solution of starting material under ice-cooling at room temperature. The ice bath was removed and the mixture was stirred overnight. Half of the solvent was evaporated, the mixture was diluted with water (80 mL) and extracted with EtOAc (3×30 mL). The collected organic phase was washed with water and brine (2×200 mL), dried and evaporated to afford the title compound (4.4 g), yield 83%. LCMS (ESI): calc'd for $C_9H_8N_2O_2$, $[M+H]^+$: 177. found: 177.

Step 2. Preparation of Methyl 3-iodo-1H-indazole-6-carboxylate (i-14c)

Methyl 1H-indazole-6-carboxylate (i-14b) (5.0 g, 28.3 mmol) was dissolved in anhydrous DMAc (50 mL). Iodine (14.4 g, 56.7 mmol) and potassium hydroxide (6.3 g, 113.5 mmol) were added in portions under ice-cooling at room temperature. The ice bath was removed and the mixture was stirred at room temperature for 1 h and then was slowly quenched with $Na_2S_2O_3$ (sat. sol. in water, 100 mL), diluted with water (50 mL) and extracted with EtOAc (3×100 mL). The organic phase was evaporated and triturated with n-hexane. The precipitated material was filtered and dried to afford the title compound as a brown solid (5.3 g), yield 62%. LCMS(ESI): calc'd for $C_9H_7IN_2O_2$, $[M+H]^+$: 303. found: 303.

Step 3. Preparation of methyl 1-(2-chloro-6-(trifluoromethyl)benzoyl)-3-iodo-1H-indazole-6-carboxylate (i-14d)

To a 250 mL round-bottomed flask, was added methyl 3-iodo-1H-indazole-6-carboxylate (i-14c) (11.7 g, 38.7 mmol), 2-chloro-6-(trifluoromethyl)benzoyl chloride (9.1 g, 38.7 mmol), DMAP (4.72 g, 38.7 mmol) and $CH_2Cl_2$ (30 mL). After stirring at room temperature for 3 minutes, TEA (11.2 mL, 77 mmol) was added slowly. The reaction mixture was stirred at room temperature for 14 h. The mixture was poured into 30 mL water, and extracted with DCM. The combined organic phases were washed successively with water and brine. The reaction resulting organic phase was dried over anhydrous sodium sulfate, filtered and concentrated at reduced pressure to give a yellow solid. The residue was purified by column chromatography eluting with Petroleum ether/EtOAc from 50/1 to 10/1, to give the title compound (16.5 g, yield 84%). LCMS (ESI): calc'd for $C_{17}H_9ClF_3IN_2O_3$, $[M+H]+$: 509. found: 509.

Step 4. methyl 3-(4-(tert-butoxycarbonyl)piperidin-1-yl)-1-(2-chloro-6-(trifluoromethyl)benzoyl)-1H-indazole-6-carboxylate (i-14e)

To a flask was added methyl 1-(2-chloro-6-(trifluoromethyl)benzoyl)-3-iodo-1H-indazole-6-carboxylate (i-14d) (500 mg, 0.983 mmol), tert-butyl piperidine-4-carboxylate (273 mg, 1.475 mmol), chloro(2-dicyclohexylphosphino-2',6'-di-I-propoxy-1,1'-biphenyl)[2-(2-aminoethylphenyl)]palladium(II), methyl-t-butylether (80 mg, 0.098 mmol), cesium carbonate (641 mg, 1.966 mmol), and dioxane (4915 μl). The vial was capped and heated to 80° C. overnight. The mixture was cooled, diluted with ethyl acetate, washed 2× with aqueous sodium hydrogen carbonate and 1× with brine. Aqueous layers were back extracted once with ethyl acetate, combined organic layers were dried with $Na_2SO_4$, filtered and the solvent was evaporated under reduced pressure. The residue was purified by flash chromatography (EtOAc/Hexane 10-75%) to give the desired product as a yellow solid. (48 mg, 47%) LCMS (ESI) calc'd for $C_{27}H_{27}ClF_3N_3O_5$, $[M+H]^+$: 566. found: 566.

Step 5. 3-(4-(tert-butoxycarbonyl)piperidin-1-yl)-1-(2-chloro-6-(trifluoromethyl)benzoyl)-1H-indazole-6-carboxylic acid (i-14)

To a vial was added methyl 3-(4-(tert-butoxycarbonyl)piperidin-1-yl)-1-(2-chloro-6-(trifluoromethyl)benzoyl)-1H-indazole-6-carboxylate (i-14e) (175 mg, 0.309 mmol), lithium hydroxide (74.0 mg, 3.09 mmol), THF (1546 μl), and water (1546 μl) and the solution was allowed to stir overnight. The reaction was acidified with 2N HCl and then washed 2× with ethyl acetate. The organic layers were combined, dried with sodium sulfate, filtered and concentrated to give the desired product. (171 mg, 100%) LCMS (ESI) calc'd for $C_{26}H_{25}ClF_3N_3O_5$ $[M+H]^+$: 552. found: 552.

Example i-15

Preparation of 4-fluoro-3-iodo-1-(tetrahydro-2H-pyran-2-yl)-1H-indazole

Scheme i-15

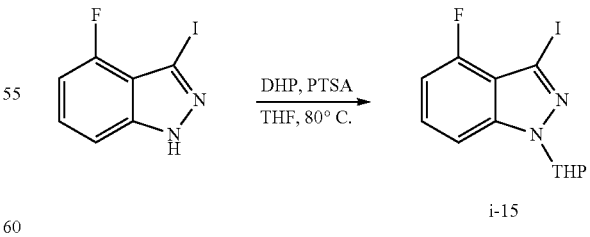

i-15

To a solution of 4-fluoro-3-iodo-1H-indazole (10 g, 38.1 mmol) in 150 mL of THF was added DHP (11.5 g, 122.4 mmol) and PTSA (776 mg, 4 mmol). The reaction mixture was heated to reflux for 6 h, cooled down, and slowly poured into water. The mixture was extracted with EtOAc (300 mL*3) and the extracts were washed with brine, dried over Na₂SO₄ and concentrated to afford the crude product. The crude product was purified by silica gel chromatography eluted with PE:EA=50:1 to 5:1 to afford the title compound (7 g, 54%) as a yellow solid. LCMS (ESI) calc'd for C₁₂H₁₂FIN₂O [M+H]⁺: 347. found: 347.

Example i-16

Preparation of ethyl trans-3-((tert-butyldiphenylsilyl)oxy)-1-(4-fluoro-1H-indazol-3-yl)piperidine-4-carboxylate Scheme i-16

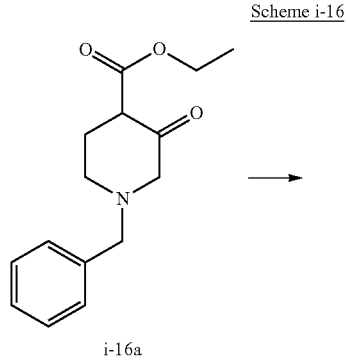

i-16a

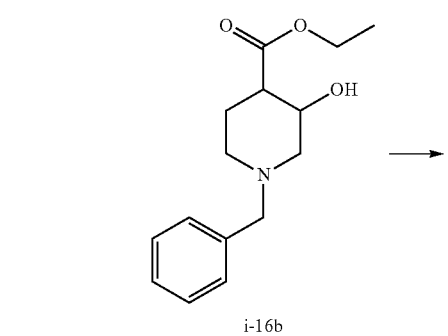

i-16b

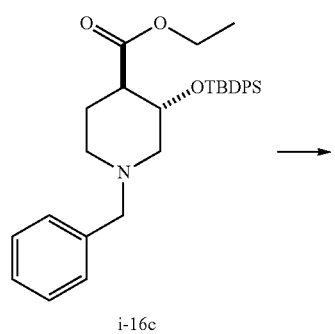

i-16c

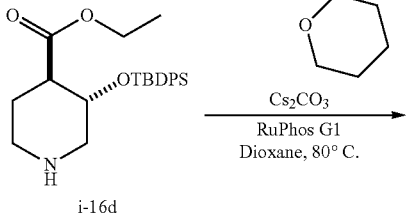

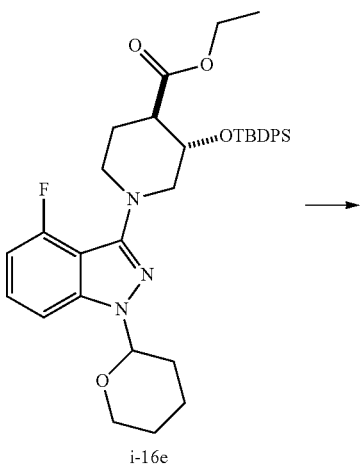

i-16d i-16e i-16

Step 1. Preparation of ethyl 1-benzyl-3-hydroxypiperidine-4-carboxylate (i-16b)

A solution of ethyl 1-benzyl-3-oxopiperidine-4-carboxylate, HCl salt (20.0 g, 67.2 mmol) in MeOH (200 ml) in a 500 ml 3-neck flask equipped with thermocouple was cooled to 0° C., followed by the addition of sodium borohydride (7.62 g, 201 mmol) portionwise over a period of 75 min, avoiding excessive gas evolution. After addition, the mixture was stirred at room temperature for 2.5 hr. The mixture was cooled to 0° C., quenched dropwise with 200 ml H₂O and extracted into EtOAc. The combined organics were washed with water followed by brine, dried over Na₂SO₄, filtered and concentrated in vacuo to give ethyl 1-benzyl-3-hydroxypiperidine-4-carboxylate. LCMS (ESI) calc'd for C₁₅H₂₁NO₃ [M+H]⁺: 264. found: 264.

Step 2. Preparation of ethyl trans-1-benzyl-3-((tert-butyldiphenylsilyl)oxy)piperidine-4-carboxylate (i-16c)

A solution of ethyl 1-benzyl-3-hydroxypiperidine-4-carboxylate (16.95 g, 63.5 mmol) and imidazole (13.15 g, 193 mmol) in DMF (85 ml) was cooled to 0° C., charged with TBDPS-Cl (15 ml, 58.4 mmol) and stirred at room temperature for 64.5 hr. The mixture was quenched with 100 ml water slowly and extracted with MTBE (2×). The combined organics were washed with brine, dried over Na$_2$SO$_4$, filtered, concentrated in vacuo onto SiO$_2$ and purified via flash chromatography (Silicycle 40 g, 0-15% EtOAc/Hexanes) to provide ethyl trans-1-benzyl-3-((tert-butyldiphenylsilyl)oxy)piperidine-4-carboxylate. LCMS (ESI) calc'd for C$_{31}$H$_{39}$NO$_3$Si [M+H]$^+$: 502. found: 502.

Step 3. Preparation of ethyl trans-3-((tert-butyldiphenylsilyl)oxy)piperidine-4-carboxylate (i-16d)

A solution of ethyl trans-1-benzyl-3-((tert-butyldiphenylsilyl)oxy)piperidine-4-carboxylate (10.257 g, 20.44 mmol) and AcOH (5.85 ml, 102 mmol) in ethanol (50 ml) was evacuated and backfilled with nitrogen (3×), charged with Pd—C (2.08 g, 1.955 mmol), evacuated and backfilled with hydrogen (3×) and stirred at room temperature for 14 hr under a balloon of hydrogen. The solution was filtered through celite, eluting with DCM. The filtrate was concentrated in vacuo, then taken up in 100 ml EtOAc. Vigorous stirring with 200 ml sat aq NaHCO$_3$ and layer separation occurred. The combined organics were washed with sat aq NaHCO$_3$, water and brine, dried over Na$_2$SO$_4$, and filtered. The filtrate was concentrated in vacuo to provide ethyl trans-3-((tert-butyldiphenylsilyl)oxy)piperidine-4-carboxylate. LCMS (ESI) calc'd for C$_{24}$H$_{33}$NO$_3$Si [M+H]$^+$: 412. found: 412.

Step 4. Preparation of ethyl trans-3-((tert-butyldiphenylsilyl)oxy)-1-(4-fluoro-1-(tetrahydro-2H-pyran-2-yl)-1H-indazol-3-yl)piperidine-4-carboxylate (i-16e)

A mixture of 4-fluoro-3-iodo-1-(tetrahydro-2H-pyran-2-yl)-1H-indazole (5.00 g, 14.45 mmol), ethyl trans-3-((tert-butyldiphenylsilyl)oxy)piperidine-4-carboxylate (7.96 g, 17.6 mmol), Cs$_2$CO$_3$ (14.1 g, 43 mmol) and Buchwald RuPhos first generation Precatalyst (953 mg, 1.17 mmol) in dioxane (35 ml) was sparged with N$_2$, sealed and heated to 80° C. for 20 hr. The mixture was filtered through celite, eluting with EtOAc. Organics were concentrated in vacuo onto SiO$_2$ and purified via flash chromatography (10-40% EtOAc/Hex) to provide ethyl trans-3-((tert-butyldiphenylsilyl)oxy)-1-(4-fluoro-1-(tetrahydro-2H-pyran-2-yl)-1H-indazol-3-yl)piperidine-4-carboxylate. LCMS (ESI) calc'd for C$_{36}$H$_{44}$FN$_3$O$_4$Si [M+H]$^+$: 630. found: 630.

Step 5. Preparation of ethyl trans-3-((tert-butyldiphenylsilyl)oxy)-1-(4-fluoro-1H-indazol-3-yl)piperidine-4-carboxylate (i-16)

A solution of ethyl trans-3-((tert-butyldiphenylsilyl)oxy)-1-(4-fluoro-1-(tetrahydro-2H-pyran-2-yl)-1H-indazol-3-yl)piperidine-4-carboxylate (8.0 g, 12.8 mmol) in DCM (56 ml) and methanol (16 ml) in a 250 ml 3-neck RBF equipped with addition funnel and thermocouple was cooled to ~5° C. internal temperature then charged dropwise with concentrated HCl (10.5 ml, 128 mmol). The solution was removed from cold bath and stirred at room temperature for 51 hr, then diluted with water (temperature rose to ~30° C.), and layer separation occurred. After extracting with DCM, the combined organics were washed with sat aq NaHCO$_3$ followed by brine, dried over Na$_2$SO$_4$, filtered, concentrated in vacuo and purified via flash chromatography (10-50% EtOAc/Hexanes) to provide ethyl trans-3-((tert-butyldiphenylsilyl)oxy)-1-(4-fluoro-1H-indazol-3-yl)piperidine-4-carboxylate. LCMS (ESI) calc'd for C$_{31}$H$_{36}$FN$_3$O$_3$Si [M+H]$^+$: 546. found: 546. $^1$H NMR (600 MHz, CDCL3) δ 7.63 (4H, dd, J=14.4, 6.8 Hz), 7.33 (6H, m), 7.07 (1H, d, J=8.5 Hz), 6.60 (1H, dd, J=10.8, 7.9 Hz), 4.27 (1H, m), 3.98 (2H, m), 3.75 (1H, dd, J=12.0, 3.8 Hz), 3.69 (1H, d, J=12.4 Hz), 2.99 (1H, m), 2.89 (1H, m), 2.63 (1H, dt, J=11.8, 4.1 Hz), 2.04 (1H, d, J=10.9 Hz), 1.91 (1H, m), 1.16 (3H, m), 0.97 (9H, s).

Method for Preparation of the Compound

Example 1A

Preparation of (3R,4R and 3S,4S)-1-(1-(2-chloro-6-(trifluoromethyl)benzoyl)-1H-pyrazolo[4,3-b]pyridin-3-yl)-3-methylpiperidine-4-carboxylic acid (1A)

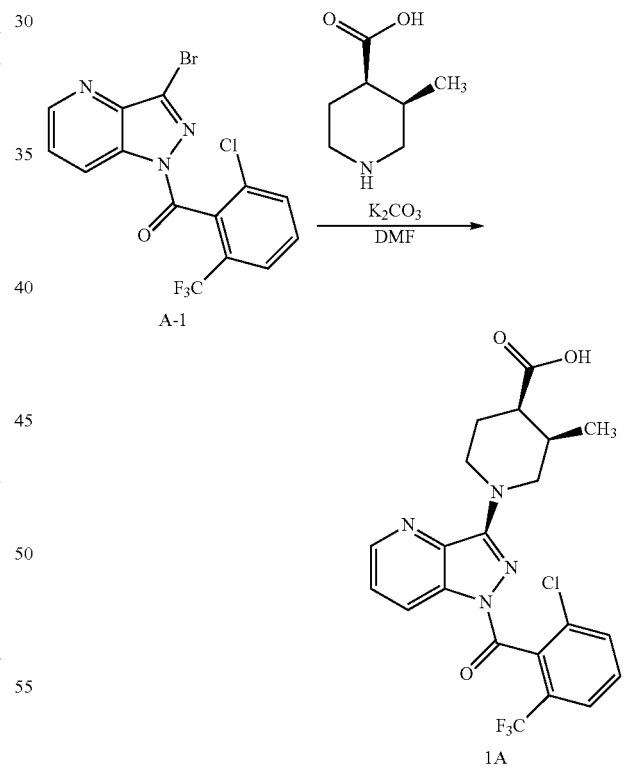

Scheme A

Step 1. Preparation of (3R,4R and 3S,4S)-1-(1-(2-chloro-6-(trifluoromethyl)benzoyl)-1H-pyrazolo[4,3-b]pyridin-3-yl)-3-methylpiperidine-4-carboxylic acid (1A)

To a solution of (3-bromo-1H-pyrazolo[4,3-b]pyridin-1-yl)(2-chloro-6-(trifluoro methyl)phenyl)methanone (A-1)

(200 mg, 0.5 mmol) and (3R,4R and 3S,4S)-3-methylpiperidine-4-carboxylic acid 2 (107 mg, 0.75 mmol) in DMF (10 mL) was added K$_2$CO$_3$ (207 mg, 1.5 mmol), and the mixture was stirred at 100° C. for 2 hr by microwave. Then the mixture was poured into water and extracted with EA (2×40 ml). The combined organic layers were dried over Na$_2$SO$_4$ and concentrated to obtain a crude product. The crude product was purified by prep-HPLC (CH$_3$CN/H$_2$O) to obtain 60 mg (26%) of the title compound. LCMS (ESI): calc'd for C$_{21}$H$_{18}$ClF$_3$N$_4$O$_3$[M+H]$^+$: 467. found: 467; $^1$H NMR (400 MHz, CDCL3) δ 8.83-8.81 (1H, d), 8.68-8.66 (1H, d), 7.70-7.67 (2H, m), 7.58-7.54 (1H, t), 7.52-7.48 (1H, m), 4.44-4.40 (2H, m), 3.37-3.33 (1H, m), 3.18-3.12 (1H, m), 2.76-2.71 (1H, m), 2.37 (1H, s), 2.04-1.97 (1H, m), 1.83-1.77 (1H, m), 1.01-0.97 (3H, m).

Example 1B

Preparation of 8-(1-(2-chloro-6-(trifluoromethyl)benzoyl)-1H-pyrazolo[4,3b]pyridin-3-yl)-8-aza-bicyclo[3.2.1]octane-3-carboxylic acid (1B)

Scheme B

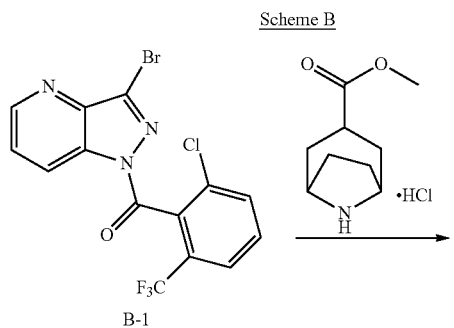

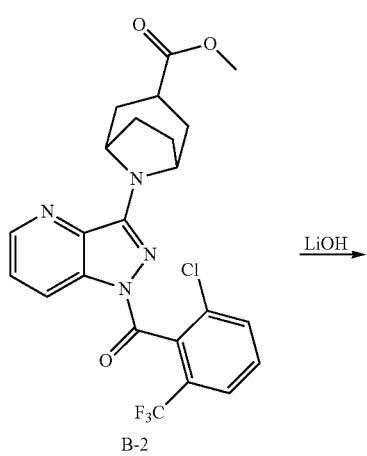

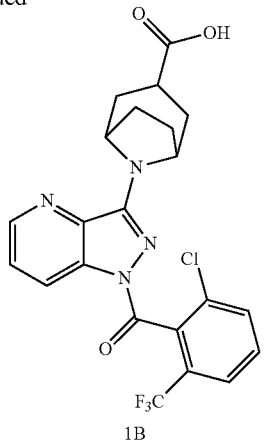

Step 1. Preparation of methyl 8-(1-(2-chloro-6-(trifluoromethyl)benzoyl)-1H-pyrazolo[4,3-b]pyridin-3-yl)-8-aza-bicyclo[3.2.1]octane-3-carboxylate (B-2)

A mixture of (3-bromo-1H-pyrazolo[4,3-b]pyridin-1-yl)(2-chloro-6-(trifluoromethyl)phenyl)methanone (B-1) (200 mg, 0.50 mmol), 3-(methoxycarbonyl)-8-azonia-bicyclo[3.2.1]octane chloride 2 (0.15 g, 0.75 mmol) and Cs$_2$CO$_3$ (0.65 g, 2.0 mmol) were suspended in DMF (5 mL). The reaction mixture was heated at 150° C. in a microwave reactor for 5 h. The resulting mixture was diluted with H$_2$O (50 mL). 2M HCl solution was added to adjust the pH to ~3 and the aqueous layer was extracted with ethyl acetate (3×20 mL). The combined organic layers were washed with brine (20 mL), dried over anhydrous Na$_2$SO$_4$ and concentrated to obtain the crude product B-2 as yellow oil. LCMS (ESI) calc'd for C$_{23}$H$_{20}$ClF$_3$N$_4$O$_3$ [M+H]$^+$: 493. found: 493.

Step 2. Preparation of 8-(1-(2-chloro-6-(trifluoromethyl)benzoyl)-1H-pyrazolo[4,3-b]pyridin-3-yl)-8-aza-bicyclo[3.2.1]octane-3-carboxylic acid (2B)

The mixture of methyl 8-(1-(2-chloro-6-(trifluoromethyl)benzoyl)-1H-pyrazolo[4,3-b]pyridin-3-yl)-8-aza-bicyclo[3.2.1]octane-3-carboxylate (B-2) (100 mg, 0.20 mmol) and LiOH.H$_2$O (42 mg, 1.0 mmol) in THF (4 mL) and H$_2$O (2 mL) was stirred at room temperature for 14 h. The reaction mixture was diluted with H$_2$O (20 mL), acidified with 2M HCl to pH~3 and extracted with ethyl acetate (3×20 mL). The combined organic layers were washed with brine (20 mL), dried over anhydrous Na$_2$SO$_4$ and concentrated. The residue was purified with Prep-HPLC (CH$_3$CN/H$_2$O) to obtain the desired product 2B as a white solid. LCMS (ESI) calc'd for C$_{22}$H$_{18}$ClF$_3$N$_4$O$_3$ [M+H]$^+$ 479. found: 479; $^1$HNMR (400 MHz, MeOD) δ 8.77 (1H, d, J=8.4 Hz), 8.72 (1H, d, J=4.4 Hz), 7.80-7.83 (2H, m), 7.69-7.73 (1H, m), 7.63-7.67 (1H, m), 4.93 (2H, s), 2.87-2.94 (1H, m), 2.05-2.08 (2H, m), 1.95-2.02 (1H, m), 1.82-1.89 (3H, m), 1.66-1.69 (2H, m).

Example 1C

Preparation of 1-(1-(2-chloro-6-(trifluoromethyl)benzoyl)-4-fluoro-1H-indazol-3-yl)pyrrolidine-3-carboxylic acid (1C)

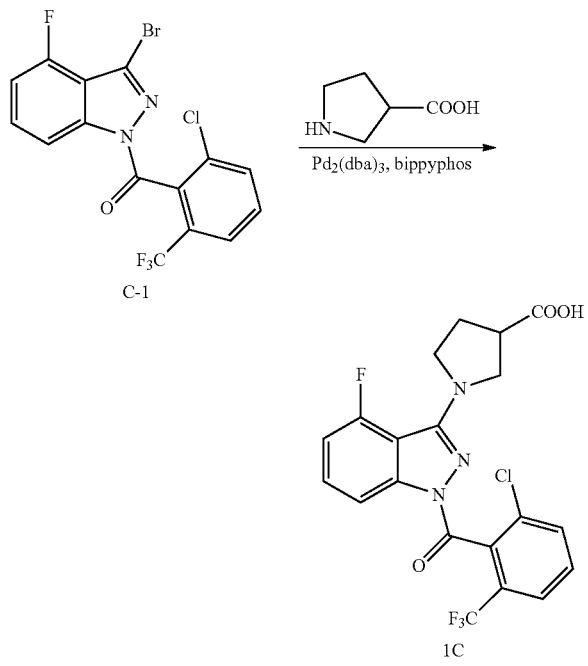

To a solution of bippyphos (10 mg, 0.019 mmol) in tert-amyl alcohol (0.8 ml) was added Pd$_2$(dba)$_3$ (10 mg, 0.0095 mmol) and a drop of water to maintain a homogeneous reaction mixture. The mixture was stirred for 15 min, followed by the addition of (3-bromo-4-fluoro-1H-indazol-1-yl)(2-chloro-6-(trifluoromethyl)phenyl)methanone (40 mg, 0.095 mmol), pyrrolidine-3-carboxylic acid (14 mg, 0.117 mmol) and Cs$_2$CO$_3$ (93 mg, 0.284 mmol). The mixture was purged with N$_2$ and then heated at 100° C. for 12 hr. The mixture was diluted with H$_2$O, and the organic layer was separated. The aqueous layer was extracted with EtOAc (3×10 mL). The combined organics were dried over anhydrous Na$_2$SO$_4$, and concentrated. The residue was purified by prep-TLC (Petroleum/EtOAc, 2/1) to afford 17 mg (40%) of the title compound. LCMS (ESI) calc'd for C$_{20}$H$_{14}$ClF$_4$N$_3$O$_3$ [M+H]$^+$ 456. found: 456. $^1$HNMR (400 MHz, CDCl$_3$) δ 8.44 (1H, d, J=8.0 Hz), 7.64-7.67 (2H, m), 7.51-7.60 (2H, m), 7.04-7.09 (1H, m), 3.56-3.75 (4H, m), 3.17-3.20 (1H, m), 2.24-2.30 (2H, m).

The following examples shown in TABLE 1 were prepared following similar procedures described for Example 1A, Example 1B and Example 1C in Scheme A, Scheme B and Scheme C which can be achieved by those of ordinary skill in the art of organic synthesis in light of the present disclosure.

TABLE 1

| Chemical Name | A ring | P | Q | LCMS [M + H]$^+$ Found |
|---|---|---|---|---|
| 1D (3R,4R and 3S, 4S)-1-(1-(2-chloro-6-(trifluoromethyl)benzoyl)-4-fluoro-1H-indazol-3-yl)-3-methylpiperidine-4-carboxylic acid | | | | 484 |

TABLE 1-continued

| Chemical Name | A ring | P | Q | LCMS [M + H]+ Found |
|---|---|---|---|---|
| 1E 1-(1-(2-chloro-6-(trifluoromethyl)benzoyl)-4-fluoro-1H-indazol-3-yl)-4-methylpiperidine-4-carboxylic acid | | | | 484 |
| 1F (2-chloro-6-(trifluoromethyl)phenyl)(4-fluoro-3-(4-hydroxy-4-(trifluoromethyl)piperidin-1-yl)-1H-indazol-1-yl)methanone | | | | 510 |
| 1G 1-(1-(2-chloro-6-(trifluoromethyl)benzoyl)-4-fluoro-1H-indazol-3-yl)-4-phenylpiperidine-4-carboxylic acid | | | | 546 |
| 1H Cis-4-(1-(2-chloro-6-(trifluoromethyl)benzoyl)-4-fluoro-1H-indazol-3-ylamino)cyclohexanecarboxylic acid | | | | 484 |
| 1I 1-(1-(2-chloro-6-(trifluoromethyl)benzoyl)-4-fluoro-1H-indazol-3-yl)piperidine-4-carboxylic acid | | | | 470 |

TABLE 1-continued

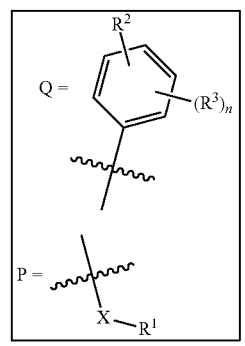

| Chemical Name | A ring | P | Q | LCMS [M + H]+ Found |
|---|---|---|---|---|
| 1J 2-(1-(1-(2-chloro-6-(trifluoromethyl)benzoyl)-4-fluoro-1H-indazol-3-yl)piperidin-4-yl)acetic acid | | | | 484 |
| 1K 1-(1-(2-chloro-6-(trifluoromethyl)benzoyl)-1H-pyrazolo[4,3-b]pyridin-3-yl)-3-hydroxypiperidine-4-carboxylic acid | | | | 469 |
| 1L 1-(1-(2-chloro-6-(trifluoromethyl)benzoyl)-1H-pyrazolo[4,3-b]pyridin-3-yl)-1,2,3,6-tetrahydropyridine-4-carboxylic acid | | | | 451 |
| 1M 1-(1-(2-chloro-6-(trifluoromethyl)benzoyl)-1H-pyrazolo[4,3-b]pyridin-3-yl)piperidine-4-carboxylic acid | | | | 453 |
| 1N 1-(1-(2-chloro-6-(trifluoromethyl)benzoyl)-1H-pyrazolo[4,3-b]pyridin-3-yl)-4-fluoropiperidine-4-carboxylic acid | | | | 471 |

TABLE 1-continued

| Chemical Name | A ring | P | Q | LCMS [M + H]+ Found |
|---|---|---|---|---|
| 1O 1-(1-(2-chloro-6-(trifluoromethyl)benzoyl)-1H-pyrazolo[4,3-b]pyridin-3-yl)-3-fluoropiperidine-4-carboxylic acid | | | | 471 |
| 1P (2-chloro-6-(trifluoromethyl)phenyl)(3-(4-hydroxy-4-(trifluoromethyl)piperidin-1-yl)-1H-pyrazolo[4,3-b]pyridin-1-yl)methanone | | | | 493 |
| 1Q 2-(1-(1-(2-chloro-6-(trifluoromethyl)benzoyl)-1H-pyrazolo[4,3-b]pyridin-3-yl)azetidin-3-yl)acetic acid | | | | 438 |
| 1R 1-(1-(2-chloro-6-(trifluoromethyl)benzoyl)-6-(dimethylcarbamoyl)-1H-indazol-3-yl)piperidine-4-carboxylic acid | | | | 523 |

TABLE 1-continued

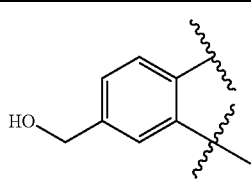

| Chemical Name | A ring | P | Q | LCMS [M + H]+ Found |
|---|---|---|---|---|
| 1S 1-(1-(2-chloro-6-(trifluoromethyl)ben-zoyl)-6-(hydroxymethyl)-1H-indazol-3-yl)piperidine-4-carboxylic acid | 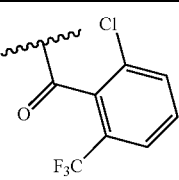 | 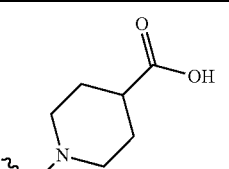 | 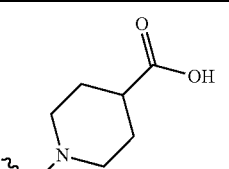 | 482 |

Example 2A

Preparation of 1-(1-(2-chloro-6-(trifluoromethyl)benzoyl)-4-fluoro-1H-indazol-3-yl)pyrrolidine-3-carboxylic acid (2A)

Scheme D

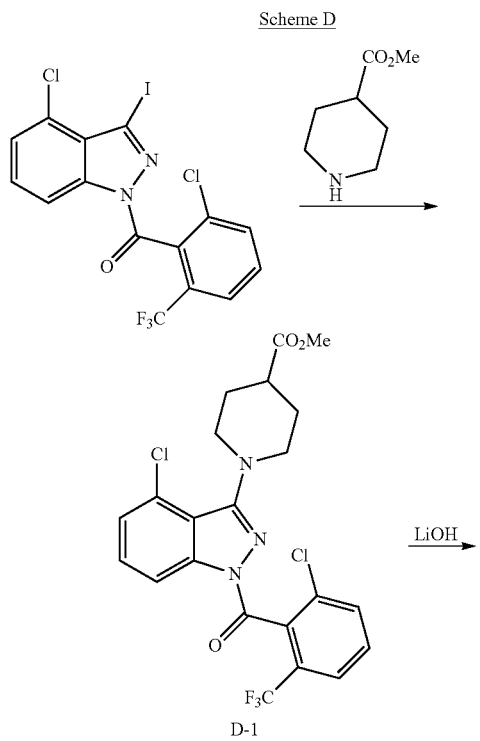

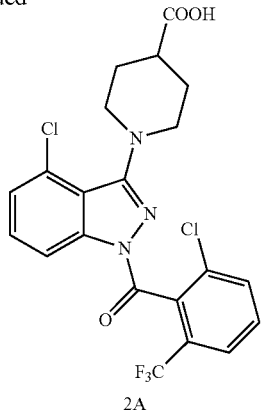
2A

Step 1. Preparation of methyl 1-(4-chloro-1-(2-chloro-6-(trifluoromethyl)benzoyl)-1H-indazol-3-yl)piperidine-4-carboxylate (D-1)

To a flask was added (4-chloro-3-iodo-1H-indazol-1-yl)(2-chloro-6-(trifluoromethyl)phenyl)methanone (100 mg, 0.206 mmol), methyl piperidine-4-carboxylate (55.7 μl, 0.412 mmol), copper(I) iodide (7.85 mg, 0.041 mmol), DL-proline (9.49 mg, 0.082 mmol), potassium carbonate (85 mg, 0.619 mmol), and N-methyl-2-pyrrolidinone (1031 μl) and the vial was capped and heated to 140° C. in the microwave for 30 min. The mixture was cooled, diluted with ethyl acetate, washed 2× with aqueous sodium hydrogen carbonate and 1× with brine. Aqueous layers were back extracted once with ethyl acetate, combined organic layers were dried with $Na_2SO_4$, filtered and the solvent was evaporated under reduced pressure. The residue was purified by flash chromatography (EtOAc/Hexane 10-75%) to give desired product as a colorless solid. (9 mg, 9%) LCMS (ESI) calc'd for $C_{22}H_{18}Cl_2F_3N_3O_3$ [M+H]+: 500. found: 500.

Step 2. Preparation of 1-(1-(2-chloro-6-(trifluoromethyl)benzoyl)-4-fluoro-1H-indazol-3-yl)pyrrolidine-3-carboxylic acid (2A)

To a flask was added methyl 1-(4-chloro-1-(2-chloro-6-(trifluoromethyl)benzoyl)-1H-indazol-3-yl)piperidine-4-carboxylate (D-1) (9 mg, 0.018 mmol), lithium hydroxide (2.154 mg, 0.090 mmol), water (180 μl), tetrahydrofuran (180 μl), and the vial was allowed to stir at room temperature for two hours. The reaction was acidified with 2N HCl and concentrated. The residue was purified by Prep-HPLC (Acetonitrile/Water+0.10% TFA 50-95%) to obtain the desired product as a colorless solid. (5 mg, 57%) LCMS (ESI) calc'd for $C_{21}H_{16}Cl_2F_3N_3O_3$ [M+H]$^+$: 486. found: 486. 1H NMR (600 MHz, DMSO) δ 12.20 (s, 1H), 8.39 (d, J=7.5 Hz, 1H), 8.00-7.86 (m, 2H), 7.77 (t, J=7.3 Hz, 1H), 7.68 (t, J=7.1 Hz, 1H), 7.56 (d, J=7.6 Hz, 1H), 3.41 (d, J=10.6 Hz, 2H), 2.68 (d, J=8.8 Hz, 2H), 2.38 (bs, 1H), 1.82 (d, J=11.1 Hz, 2H), 1.72-1.56 (m, 2H).

The following example shown in Table 2 was made using the same procedure described for Example 2A which can be achieved by those of ordinary skill in the art of organic synthesis in light of the present disclosure.

TABLE 2

| | Chemical Name | Structure | LCMS [M + H]$^+$ Found |
|---|---|---|---|
| 2B | 1-(1-(2-chloro-6-(trifluoromethyl)benzoyl)-4-methyl-1H-indazol-3-yl)piperidine-4-carboxylic acid | 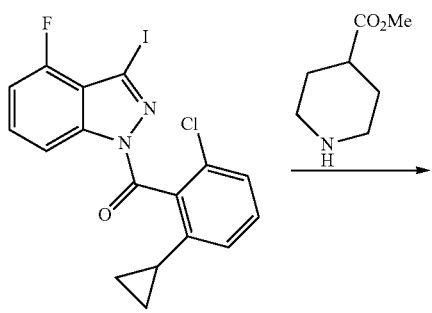 | 466 |

Example 3A

Preparation of 1-(1-(2-chloro-6-cyclopropylbenzoyl)-4-fluoro-1H-indazol-3-yl)piperidine-4-carboxylic acid (3A)

Scheme E

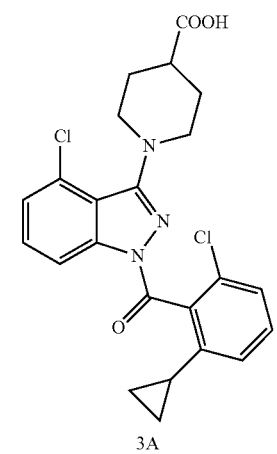

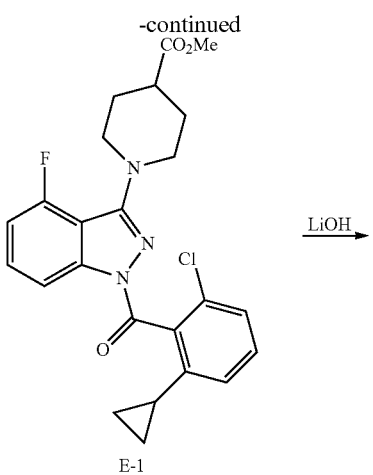

Step 1. Preparation of methyl 1-(1-(2-chloro-6-cyclopropylbenzoyl)-4-fluoro-1H-indazol-3-yl)piperidine-4-carboxylate (E-1)

To a vial was added (2-chloro-6-cyclopropylphenyl)(4-fluoro-3-iodo-1H-indazol-1-yl)methanone (98 mg, 0.222 mmol), methyl piperidine-4-carboxylate (60.1 μl, 0.445 mmol), chloro(2-dicyclohexylphosphino-2',6'-di-I-propoxy-1,1'-biphenyl)[2-(2-aminoethylphenyl)]palladium(II), methyl-t-butylether adduct (18.17 mg, 0.022 mmol), cesium carbonate (145 mg, 0.445 mmol), and dioxane (1112 μl). The vial was capped and heated to 80° C. overnight. The mixture was cooled, diluted with ethyl acetate, washed 2× with aqueous sodium hydrogen carbonate and 1× with brine. Aqueous layers were back extracted once with ethyl acetate, combined organic layers were dried with $Na_2SO_4$, filtered and the solvent was evaporated under reduced pressure. The residue was purified by flash chromatography (EtOAc/Hexane 10-75%) to give desired product as a colorless solid. (48 mg, 47%) LCMS (ESI) calc'd for $C_{24}H_{23}ClFN_3O_3$ [M+H]$^+$: 456. found: 456.

Step 2. Preparation of 1-(1-(2-chloro-6-cyclopropylbenzoyl)-4-fluoro-1H-indazol-3-yl)piperidine-4-carboxylic acid (3A)

To a vial was added methyl 1-(1-(2-chloro-6-cyclopropylbenzoyl)-4-fluoro-1H-indazol-3-yl)piperidine-4-carboxylate (E-1) (45 mg, 0.099 mmol), lithium hydroxide (11.82 mg, 0.494 mmol), THF (494 μl), and water (494 μl) and the reaction was allowed to stir at room temperature for 2 hours. The reaction was acidified with 2N HCl and concentrated. The residue was purified by Prep-HPLC (Acetonitrile/Water+0.10% TFA 50-95%) to obtain the desired product as a colorless solid. (16 mg, 37%) LCMS (ESI) calc'd for $C_{23}H_{21}ClFN_3O_3$ [M+H]$^+$: 442. found: 442. 1H NMR (600 MHz, DMSO) δ 8.31 (d, J=7.9 Hz, 1H), 7.69 (d, J=5.1 Hz, 1H), 7.46-7.31 (m, 2H), 7.31-7.23 (m, 1H), 7.00 (d, J=7.6 Hz, 1H), 3.6-3.4 (m, 2H), 2.85-2.75 (m, 2H), 2.4-2.3 (m, 1H), 1.81 (bs, 2H), 1.71-1.47 (m, 3H), 0.85-0.75 (m, 1H), 0.75-0.62 (m, 2H), 0.57 (bs, 1H).

The following example shown in Table 3 was made using the same procedure described for Example 3A which can be achieved by those of ordinary skill in the art of organic synthesis in light of the present disclosure.

TABLE 3

| Chemical Name | Structure | LCMS [M + H]$^+$ Found |
|---|---|---|
| 3B 1-(1-(2-chloro-6-cyclobutylbenzoyl)-4-fluoro-1H-indazol-3-yl)piperidine-4-carboxylic acid | | 456 |

Example 4A and 4B

Preparation of (3R,4S and 3S,4R)-1-(1-(2-chloro-6-(trifluoromethyl)benzoyl)-4-fluoro-1H-indazol-3-yl)-3-methylpiperidine-4-carboxylic acid 4A (racemic, trans) and (3R,4R and 3S,4S)-1-(1-(2-chloro-6-(trifluoromethyl)benzoyl)-4-fluoro-1H-indazol-3-yl)-3-methylpiperidine-4-carboxylic acid 4B (racemic, cis)

Scheme F

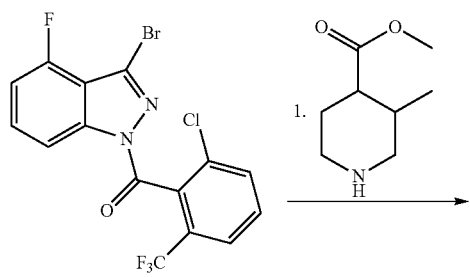

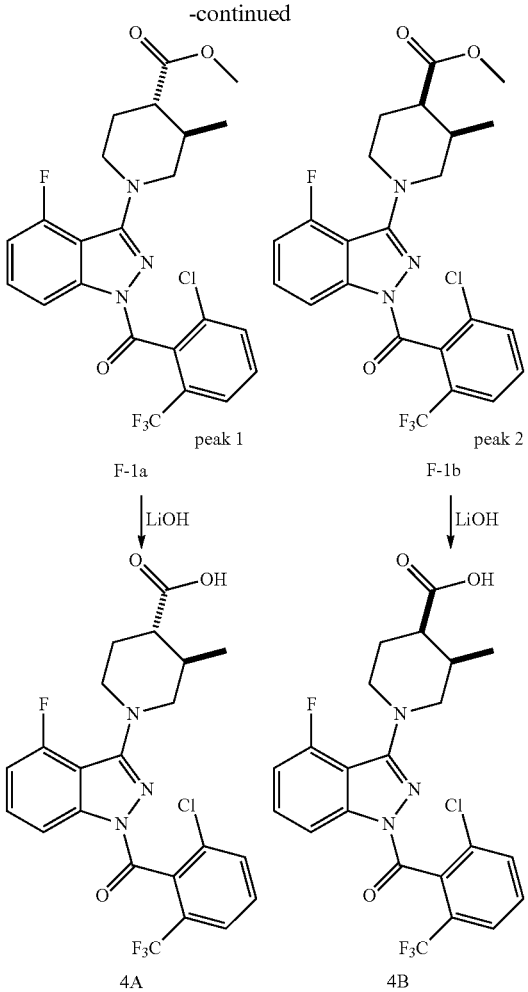

Step 1. Preparation of (3R,4S and 3S,4R)-methyl 1-(1-(2-chloro-6-(trifluoromethyl)benzoyl)-4-fluoro-1H-indazol-3-yl)-3-methylpiperidine-4-carboxylate (F-1a, racemic, trans) and (3R,4R and 3S,4S)-methyl 1-(1-(2-chloro-6-(trifluoromethyl)benzoyl)-4-fluoro-1H-indazol-3-yl)-3-methylpiperidine-4-carboxylate (F-1b, racemic, cis)

To a vial was added (3-bromo-4-fluoro-1H-indazol-1-yl)(2-chloro-6-(trifluoromethyl)phenyl)methanone (227 mg, 0.54 mmol), methyl 3-methylpiperidine-4-carboxylate (127 mg, 0.81 mmol), chloro(2-dicyclohexylphosphino-2',6'-di-I-propoxy-1,1'-biphenyl)[2-(2-aminoethylphenyl)]palladium (II), methyl-t-butylether (88 mg, 0.11 mmol), and dioxane (1.8 ml) and the solution was purged with argon for 5 minutes. Cesium carbonate (525 mg, 1.61 mmol) was then added to the reaction and the resulting solution was capped and allowed to stir at 80° C. overnight. The mixture was cooled, diluted with ethyl acetate, washed 2× with aqueous sodium hydrogen carbonate and 1× with brine. Aqueous layers were back extracted once with ethyl acetate, combined organic layers were dried with $Na_2SO_4$, filtered and the solvent was evaporated under reduced pressure. The residue was purified by flash chromatography (EtOAc/Hexane 10-75%) to give cis/trans mixture of isomers as a colorless solid. Further purification afforded two desired products. (Peak 1, trans, 21 mg) (Peak 2, cis, 34 mg) LCMS (ESI) calc'd for $C_{23}H_{20}ClF_4N_3O_3$ [M+H]$^+$: 498. found: 498.

Step 2. Preparation of (3R,4S and 3S,4R)-1-(1-(2-chloro-6-(trifluoromethyl)benzoyl)-4-fluoro-1H-indazol-3-yl)-3-methylpiperidine-4-carboxylic acid (4A, racemic, trans)

To a vial was added (3R,4S and 3S,4R)-methyl 1-(1-(2-chloro-6-(trifluoromethyl)benzoyl)-4-fluoro-1H-indazol-3-yl)-3-methylpiperidine-4-carboxylate (F-1a) (21 mg, racemic, trans, 0.042 mmol), THF (422 µl), water (422 µl), and lithium hydroxide (5.05 mg, 0.211 mmol) and the resulting mixture was allowed to stir at room temperature over 2 days. The residue was diluted with methanol and purified by Prep-HPLC (Acetonitrile/Water+0.10% TFA 60-95%) to obtain the desired product as a colorless solid. (10.5 mg, 51%) LCMS (ESI) calc'd for $C_{22}H_{18}ClF_4N_3O_3$ [M+H]$^+$: 484. found: 484. 1H NMR (600 MHz, DMSO) δ 8.25 (d, J=8.3 Hz, 1H), 7.93 (d, J=8.2 Hz, 1H), 7.88 (d, J=8.0 Hz, 1H), 7.8-7.75 (m, 2H), 7.31 (dd, J=8.2, 11.0 Hz, 1H), 3.59-3.45 (m, 2H), 2.74 (t, J=12.4 Hz, 1H), 2.45-2.4 (m, 1H), 2.09-1.95 (m, 1H), 1.87-1.72 (m, 2H), 1.63-1.51 (m, 1H), 0.8-0.7 (m, 3H).

Step 3. Preparation of (3R,4R and 3S,4S)-1-(1-(2-chloro-6-(trifluoromethyl)benzoyl)-4-fluoro-1H-indazol-3-yl)-3-methylpiperidine-4-carboxylic acid (4B, racemic, cis)

The Cis-isomer was prepared via hydrolysis from the corresponding ester (F-1b) similarly, and can be achieved by those of ordinary skill in the art of organic synthesis in light of the present disclosure. LCMS (ESI) calc'd for $C_{22}H_{18}ClF_4N_3O_3$ [M+H]$^+$: 484. found: 484. 1H NMR (600 MHz, DMSO) δ 8.25 (d, J=8.3 Hz, 1H), 7.94 (d, J=8.2 Hz, 1H), 7.88 (d, J=7.9 Hz, 1H), 7.79-7.69 (m, 2H), 7.31 (dd, J=8.1, 11.1 Hz, 1H), 3.54-3.48 (m, 1H), 3.48-3.40 (m, 1H), 2.99-2.89 (m, 1H), 2.79-2.64 (m, 1H), 2.60-2.51 (m, 1H), 2.27-2.15 (m, 1H), 1.79-1.68 (m, 1H), 1.63-1.52 (m, 1H), 0.87-0.8 (m, 3H).

Example 5A 8-(1-(2-chloro-6-(trifluoromethyl)benzoyl)-4-fluoro-1H-indazol-3-yl)-8-azabicyclo[3.2.1]octane-3-carboxylic acid (5A)

Scheme G

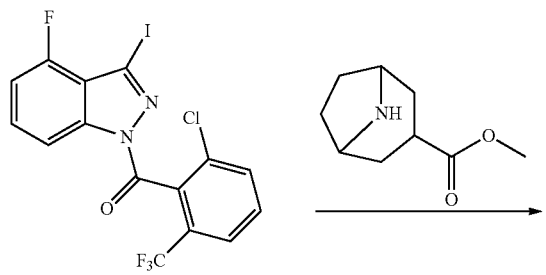

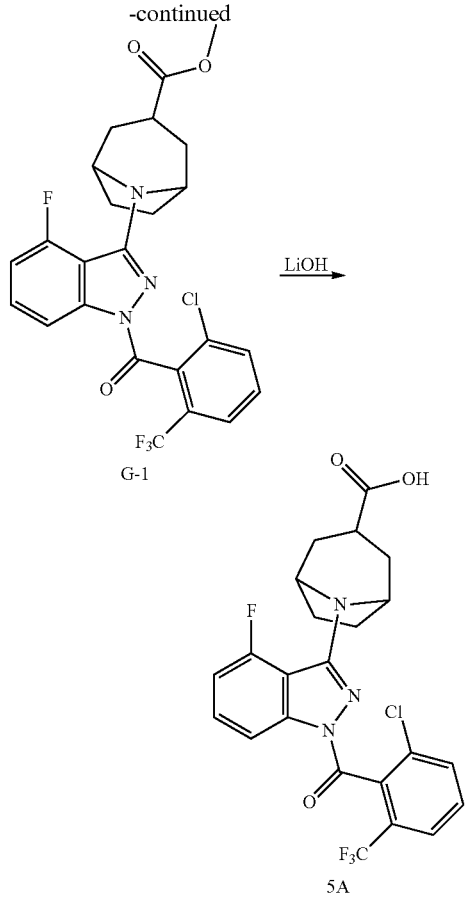

Step 1. Methyl 8-(1-(2-chloro-6-(trifluoromethyl)benzoyl)-4-fluoro-1H-indazol-3-yl)-8-azabicyclo[3.2.1]octane-3-carboxylate To a vial containing (2-chloro-6-(trifluoromethyl)phenyl)(4-fluoro-3-iodo-1H-indazol-1-yl)methanone (35 mg, 0.075 mmol) dissolved in dioxane (1.0 mL) were added (methyl 8-azabicyclo[3.2.1]octane-3-carboxylate (25.3 mg, 0.149 mmol), Buchwald RuPhos Indoline Precatalyst (5.44 mg, 0.0075 mmol) and cesium carbonate (75 mg, 0.224 mmol). The reaction mixture was stirred while heating to 90° C. overnight. The reaction was allowed to cool to room temperature, diluted with THF (1 mL) and filtered to collect yellow solution which was carried forward into step 2 without purification. LCMS (ESI) calc'd for $C_{24}H_{21}ClF_4N_3O_3$ [M+H]+: 510. found: 510.

Step 2. Preparation of 8-(1-(2-chloro-6-(trifluoromethyl)benzoyl)-4-fluoro-1H-indazol-3-yl)-8-azabicyclo[3.2.1]octane-3-carboxylic acid To a vial containing Methyl 8-(1-(2-chloro-6-(trifluoromethyl)benzoyl)-4-fluoro-1H-indazol-3-yl)-8-azabicyclo[3.2.1]octane-3-carboxylate (G-1) as the solution from Step 1 was added 1N lithium hydroxide solution. The reaction was left to stir at room temperature overnight. The solvent was evaporated under reduced pressure. DMSO (1.0 mL) was added to dissolve the crude sample and the material was purified by mass triggered prep-HPLC ($CH_3CN/H_2O$) to obtain 13.2 mg (35%) of the title compound. LCMS (ESI) calc'd for $C_{23}H_{19}ClF_4N_3O_3$ [M+H]+: 496. found: 496. 1H NMR (600 MHz, DMSO) δ 8.23 (d, J=8.3 Hz, 1H), 7.92 (d, J=8.1 Hz, 1H), 7.87 (d, J=8.0 Hz, 1H), 7.74 (m, 2H), 7.31 (m, 1H), 4.10 (s, 2H), 2.58 (m, 1H), 1.68 (m, 8H).

The following examples shown in Table 4 were made using the same procedure described for Example 5A which can be achieved by those of ordinary skill in the art of organic synthesis in light of the present disclosure.

TABLE 4

| Chemical Name | Structure | LCMS [M + H]+ Found |
|---|---|---|
| 5B (1R,5S)-9-(1-(2-chloro-6-(trifluoromethyl)benzyl)-4-fluoro-1H-indazol-3-yl)-9-azabicyclo[3.3.1]nonane-3-carboxylic acid | | 510 |
| 5C 1-(1-(2-chloro-6-(trifluoromethyl)benzoyl)-4-fluoro-1H-indazol-3-yl)-2-ethylpiperidine-4-carboxylic acid | | 498 |
| 5D 1-(1-(2-chloro-6-(trifluoromethyl)benzoyl)-4-fluoro-1H-indazol-3-yl)-4-hydroxypiperidine-4-carboxylic acid | | 486 |

Example 6A and 6B

Preparation of (3S,4R or 3R,4S)-1-(1-(2-chloro-6-cyclopropylbenzoyl)-4-fluoro-1H-indazol-3-yl)-3-hydroxypiperidine-4-carboxylic acid (6A) and (3R,4S or 3S,4R)-1-(1-(2-chloro-6-cyclopropylbenzoyl)-4-fluoro-1H-indazol-3-yl)-3-hydroxypiperidine-4-carboxylic acid (6B)

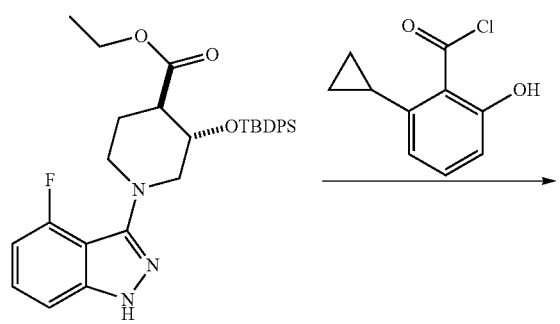

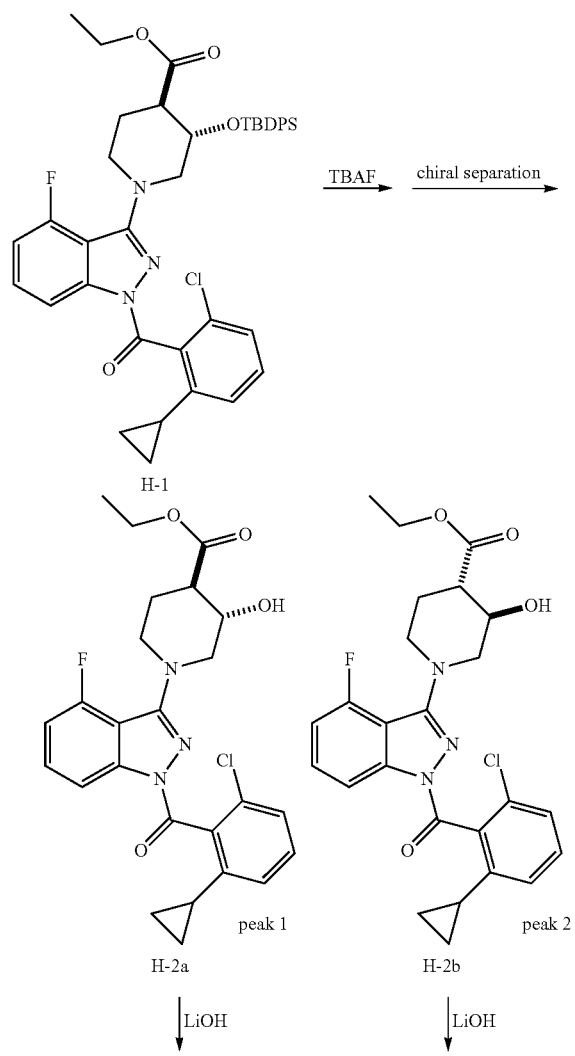

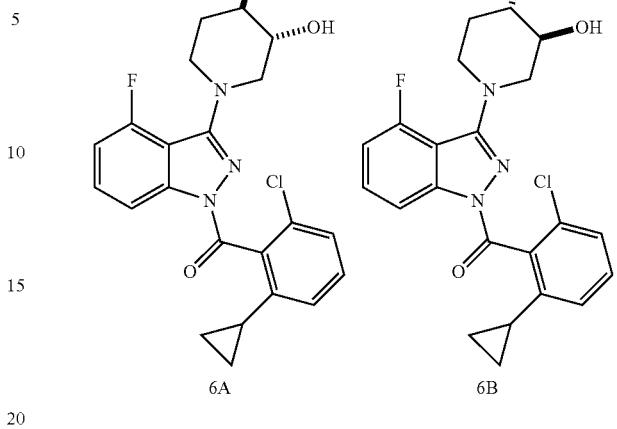

Step 1. Preparation of (3S,4R and 3R,4S)-ethyl 3-((tert-butyldiphenylsilyl)oxy)-1-(1-(2-chloro-6-cyclopropylbenzoyl)-4-fluoro-1H-indazol-3-yl)piperidine-4-carboxylate (H-1)

To a flask were added (3S,4R and 3R,4S)-ethyl 3-((tert-butyldiphenylsilyl)oxy)-1-(4-fluoro-1H-indazol-3-yl)piperidine-4-carboxylate (200 mg, 0.366 mmol), DIPEA (256 μl, 1.466 mmol), DMAP (22.39 mg, 0.183 mmol), DCM (1222 μl), and 2-chloro-6-cyclopropylbenzoyl chloride (158 mg, 0.733 mmol) and the resulting solution was allowed to stir at room temperature overnight. The reaction was then concentrated and the residue was purified by flash chromatography (EtOAc/Hexane 0-65%) to give the desired product as a colorless solid. (167 mg, 62%) LCMS (ESI) calc'd for $C_{41}H_{43}ClFN_3O_4Si$ [M+H]$^+$: 724. found: 724.

Step 2. Preparation of (3S,4R or 3R,4S)-ethyl 1-(1-(2-chloro-6-cyclopropylbenzoyl)-4-fluoro-1H-indazol-3-yl)-3-hydroxypiperidine-4-carboxylate (H-2a) and (3R,4S or 3S,4R)-ethyl 1-(1-(2-chloro-6-cyclopropylbenzoyl)-4-fluoro-1H-indazol-3-yl)-3-hydroxypiperidine-4-carboxylate (H-2b)

To a vial was added (3S,4R and 3R,4S)-ethyl 3-((tert-butyldiphenylsilyl)oxy)-1-(1-(2-chloro-6-cyclopropylbenzoyl)-4-fluoro-1H-indazol-3-yl)piperidine-4-carboxylate (H-1) (165 mg, 0.228 mmol), THF (2278 μl), and TBAF (456 μl, 0.456 mmol) and the solution was heated to 50° C. for 2 hours. The reaction was cooled and diluted with saturated ammonium chloride. The mixture was diluted with ethyl acetate, washed 1× with aqueous ammonium chloride and 1× with brine. Aqueous layers were back extracted once with ethyl acetate, combined organic layers were dried with Na2SO4, filtered and the solvent was evaporated under reduced pressure. The residue was purified by flash chromatography (EtOAc/Hexane 10-75%) to give the desired product, which was separated by chiral separation to give two separate enantiomers. Peak 1—(19.6 mg, 17%) Peak 2—(19 mg, 17%) LCMS (ESI) calc'd for $C_{25}H_{25}ClFN_3O_4$ [M+H]$^+$: 486. found: 486.

Step 3: Preparation of (3S,4R or 3R,4S)-1-(1-(2-chloro-6-cyclopropylbenzoyl)-4-fluoro-1H-indazol-3-yl)-3-hydroxypiperidine-4-carboxylic acid (6A)

To a flask was added (3S,4R or 3R,4S)-ethyl 1-(1-(2-chloro-6-cyclopropylbenzoyl)-4-fluoro-1H-indazol-3-yl)-3-hydroxypiperidine-4-carboxylate, (H-2a) (19.6 mg, 0.040 mmol), lithium hydroxide (9.7 mg, 0.40 mmol), THF (538 µl), and water (269 µl) and the solution was allowed to stir at room temperature for 2 hours. The reaction was acidified with 2N HCl and then washed 2× with ethyl acetate. Combined organic layers were dried with $Na_2SO_4$, filtered and the solvent was evaporated under reduced pressure. The residue was purified by Prep-HPLC (Acetonitrile/Water+ 0.10% TFA 50-95%) to obtain the desired product as a colorless solid. (10.7 mg, 57%) LCMS (ESI) calc'd for $C_{23}H_{21}ClFN_3O_4$ $[M+H]^+$: 458. found: 458. $^1$H NMR (600 MHz, DMSO) δ 8.31 (d, J=8.3, 1H), 7.70 (m, 1H), 7.37 (t, J=7.9 Hz, 1H), 7.33 (d, J=8.0 Hz, 1H), 7.31-7.25 (m, 1H), 7.01 (d, J=7.6 Hz, 1H), 3.7-3.6 (m, 2H), 3.58-3.45 (m, 1H), 2.67 (t, J=12.6 Hz, 1H), 2.6-2.5 (m, 1H), 2.24-2.13 (m, 1H), 1.87-1.76 (m, 1H), 1.7-1.5 (m, 2H), 0.84-0.74 (m, 1H), 0.72-0.63 (m, 2H), 0.62-0.52 (m, 1H).

Step 4: Preparation of 3R,4S or (3S,4R)-1-(1-(2-chloro-6-cyclopropylbenzoyl)-4-fluoro-1H-indazol-3-yl)-3-hydroxypiperidine-4-carboxylic acid (6B)

The other enantiomeric ester (H-2b) was hydrolyzed and purified to give the desired final product, as can be achieved by those of ordinary skill in the art of organic synthesis in light of the present disclosure. LCMS (ESI) calc'd for $C_{23}H_{21}ClFN_3O_4$ $[M+H]^+$: 458. found: 458.

The following examples shown in TABLE 5 were prepared following similar procedures described for Example 6A and 6B, in Scheme H which can be achieved by those of ordinary skill in the art of organic synthesis in light of the present disclosure.

TABLE 5

| Ex. | Chemical Name | Structure | LCMS [M + H]$^+$ Found |
|---|---|---|---|
| 6C (derived from chiral ester, peak1) | (3S,4R or 3R,4S)-1-(1-(2-chloro-6-(trifluoromethyl)benzoyl)-4-fluoro-1H-indazol-3-yl)-3-hydroxypiperidine-4-carboxylic acid | 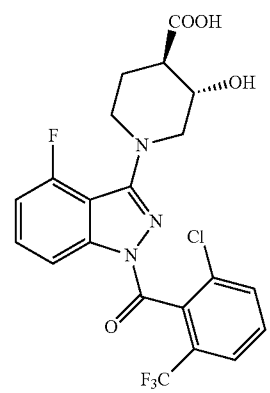 [SMILES: O=C(O)[C@@H]1CCN(c2nn(C(=O)c3c(Cl)cccc3C(F)(F)F)c3cccc(F)c23)C[C@H]1O] | 486 |
| 6D (derived from chiral ester, peak2) | (3R,4S or 3S,4R)-1-(1-(2-chloro-6-(trifluoromethyl)benzoyl)-4-fluoro-1H-indazol-3-yl)-3-hydroxypiperidine-4-carboxylic acid | 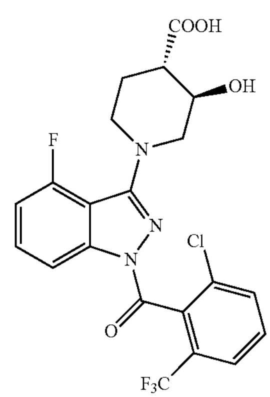 [SMILES: O=C(O)[C@H]1CCN(c2nn(C(=O)c3c(Cl)cccc3C(F)(F)F)c3cccc(F)c23)C[C@@H]1O] | 486 |

Example 7A

Preparation of (3R,4R and 3S,4S)-1-(1-(2-chloro-6-(trifluoromethyl)benzoyl)-4-fluoro-1H-indazol-3-yl)-3-hydroxypiperidine-4-carboxylic acid (7A)

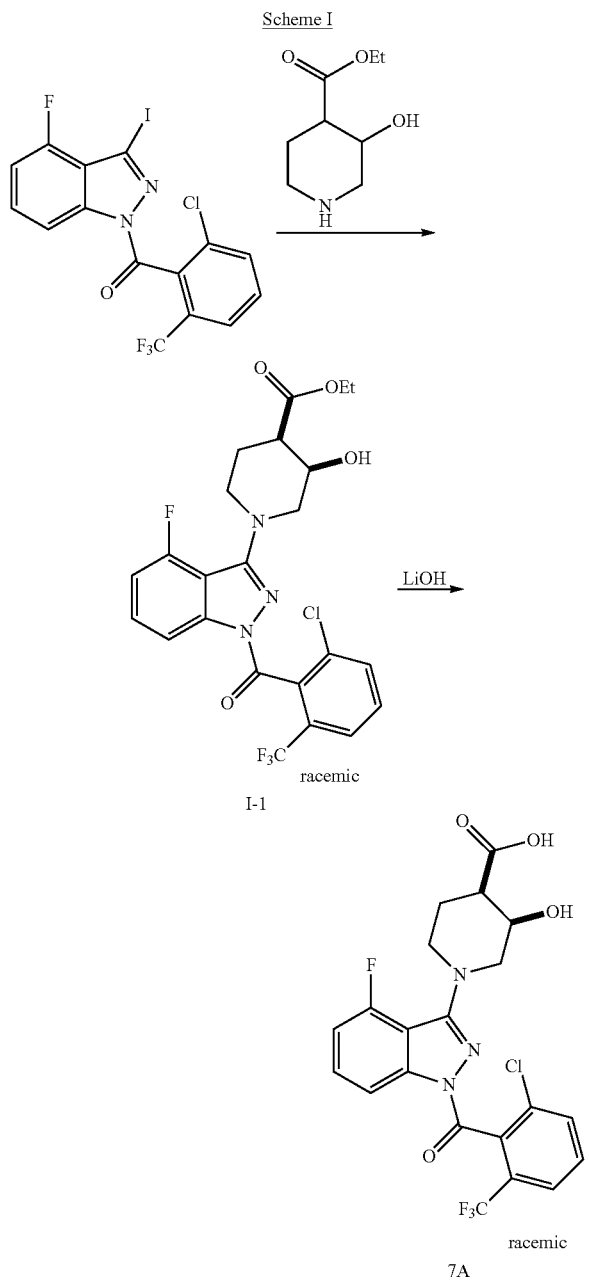

Scheme I racemic
I-1 racemic
7A

Step 1. Preparation of (3R,4R and 3S,4S)-ethyl 1-(1-(2-chloro-6-(trifluoromethyl)benzoyl)-4-fluoro-1H-indazol-3-yl)-3-hydroxypiperidine-4-carboxylate (I-1)

To a flask was added (2-chloro-6-(trifluoromethyl)phenyl)(4-fluoro-3-iodo-1h-indazol-1-yl)methanone (500 mg, 1.1 mmol), ethyl 3-hydroxypiperidine-4-carboxylate (314 mg, 1.8 mmol, mixture of cis/trans isomers, ratio ~1.5:1), DMF (5.3 ml), copper(I) iodide (31 mg, 0.16 mmol), $Cs_2CO_3$ (869 mg, 2.67 mmol) and 2-isobutyrylcyclohexanone (54 mg, 0.32 mmol). The mixture was degassed for 5 min, sealed and heated at 90° C. for 12 h. The mixture was cooled down, and diluted with EtOAc and $H_2O$. The organic layer was separated, washed with brine, dried over $MgSO_4$ and concentrated. The residue was purified by flash chromatography (10-70% EtOAc/hexanes) to give a mixture of cis and trans isomers, which was re-purified by prep-TLC (5% EtOAc/DCM) to afford the desired cis-isomer (less polar) as major, along with some minor trans-isomer (more polar) byproduct. LCMS (ESI) calc'd for $C_{23}H_{19}ClF_4N_3O_4$ [M+H]$^+$: 514. found: 514. NMR (600 MHz, CDCl3) δ 8.39 (d, J=8.4, 1H), 7.67 (t, J=7.2 Hz, 2H), 7.53-7.61 (m, 4H), 7.06-7.09 (dd, J=10.2, 8.4 Hz, 1H), 4.28 (brs, 1H), 4.18 (q, J=7.2 Hz, 2H), 3.74-3.87 (m, 2H), 2.99-3.10 (m, 2H), 2.87 (t, J=12.6 Hz, 1H), 2.53-2.57 (m, 1H), 2.17-2.23 (m, 1H), 1.83-1.86 (m, 1H), 1.28 (t, J=12.6 Hz, 3H).

Step 2. Preparation of (3R,4R and 3S,4S)-1-(1-(2-chloro-6-(trifluoromethyl)benzoyl)-4-fluoro-1H-indazol-3-yl)-3-hydroxypiperidine-4-carboxylic acid (7A)

To a solution of (3R,4R and 3S,4S)-ethyl 1-(1-(2-chloro-6-(trifluoromethyl)benzoyl)-4-fluoro-1H-indazol-3-yl)-3-hydroxypiperidine-4-carboxylate (I-1) (18 mg, 0.035 mmol, cis-isomer racemic) in THF (1 ml)/MeOH (0.5 ml) was added lithium hydroxide (0.175 ml, 0.175 mmol). The mixture was stirred at room temperature for 2 h. TLC showed completion. The mixture was acidified with 2N HCl to pH=3~4, extracted. The organic layer was dried over $MgSO_4$, concentrated, and purified by prep-HPLC to give the desired product. LCMS (ESI) calc'd for $C_{21}H_{16}ClF_4N_3O_4$ [M+H]$^+$: 486. found: 486. NMR (600 MHz, DMSO) δ 12.07 (brs, 1H), 8.25 (d, J=8.4 Hz, 1H), 7.92 (t, J=7.8 Hz, 1H), 7.87 (t, J=7.2 Hz, 1H), 7.69-7.77 (m, 2H), 7.29 (dd, J=10.8, 8.4 Hz, 1H), 4.74 (brs, 1H), 4.05 (s, 1H), 3.57-3.62 (m, 2H), 2.93 (d, J=12.6 Hz, 1H), 2.71 (t, J=12.0 Hz, 12H), 1.94-1.99 (m, 1H), 1.48-1.51 (m, 1H).

Example 8A

Preparation of (3R,4R)-1-(1-(2-chloro-6-cyclopropylbenzoyl)-4-fluoro-1H-indazol-3-yl)-3-hydroxy-4-methylpiperidine-4-carboxylic acid (8A)

Scheme J

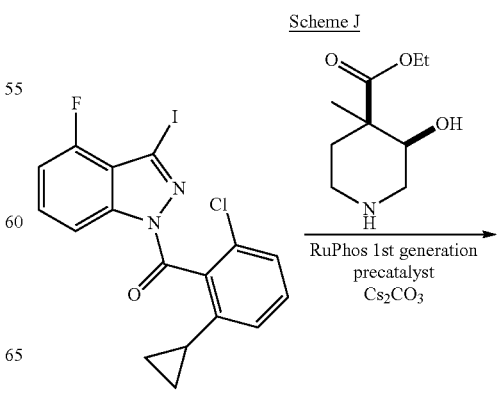

RuPhos 1st generation precatalyst
$Cs_2CO_3$

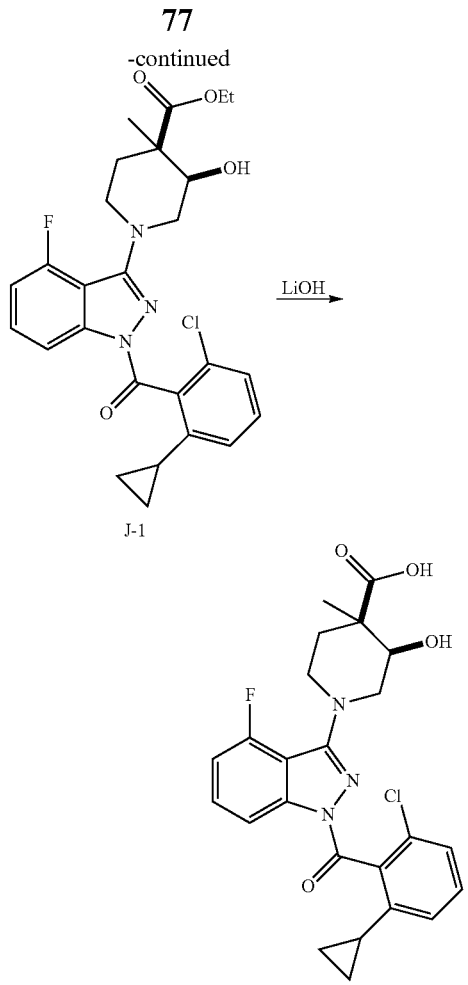

Step 1. Preparation of (3R,4R and 3S,4S)-ethyl 1-(1-(2-chloro-6-cyclopropylbenzoyl)-4-fluoro-1H-indazol-3-yl)-3-hydroxy-4-methylpiperidine-4-carboxylate (J-1)

A mixture of (2-chloro-6-cyclopropylphenyl)(4-fluoro-3-iodo-1H-indazol-1-yl)methanone (200 mg, 0.454 mmol), (3R,4R and 3S,4S)-ethyl 3-hydroxy-4-methylpiperidine-4-carboxylate (110 mg, 0.590 mmol), $Cs_2CO_3$ (444 mg, 1.362 mmol) and Buchwald RuPhos Precatalyst (55.6 mg, 0.068 mmol) in dioxane (2.2 ml) was degassed for 5 min and heated to 80° C. for 14 h. LCMS showed product formation, along with some unreacted iodide. The mixture was cooled to room temperature, and diluted with EtOAc and $H_2O$. The organic layer was separated, washed with brine, dried over MgSO4, concentrated. The residue was purified by flash chromatography (10-70% EtOAc/hexane) to give the desired product. LCMS (ESI) calc'd for $C_{26}H_{27}ClFN_3O_4$ [M+H]$^+$: 500. found: 500. NMR (600 MHz, CD3OD) δ 8.36 (d, J=8.4, 1H), 7.61-7.65 (m, 1H), 7.33 (t, J=8.4 Hz, 1H), 7.26 (dd, J=8.4. 4.2 Hz, 1H), 7.11-7.15 (m, 1H), 7.02 (dd, J=8.4, 4.2 Hz, 1H), 4.09-4.16 (m, 2H), 3.70-3.72 (m, 1H), 3.35-3.50 (m, 3H), 3.15-3.21 (m, 3H), 2.25-2.30 (m, 1H), 1.73-1.79 (m, 1H), 1.50-1.56 (m, 1H), 1.19-1.25 (m, 6H), 0.79-0.84 (m, 1H), 0.66-0.75 (m, 2H), 0.55-0.61 (m, 1H).

Step 2. Preparation of (3R,4R and 3S,4S)-1-(1-(2-chloro-6-cyclopropylbenzoyl)-4-fluoro-1H-indazol-3-yl)-3-hydroxy-4-methylpiperidine-4-carboxylic acid (8A)

To a solution of (3R,4R and 3S,4S)-ethyl 1-(1-(2-chloro-6-cyclopropylbenzoyl)-4-fluoro-1H-indazol-3-yl)-3-hydroxy-4-methylpiperidine-4-carboxylate (32 mg, 0.064 mmol) in dioxane (2 ml), was added 1M LiOH (1.28 ml, 1.280 mmol). The mixture was heated at 80° C. for 4 h, cooled down, acidified with 1N HCl to PH=3-4, extracted with EtOAc, washed with brine, dried over $MgSO_4$, and concentrated to give the final product. LCMS (ESI) calc'd for $C_{24}H_{23}ClFN_3O_4$ [M+H]$^+$: 472. found: 472. NMR (600 MHz, CD3OD) δ 8.35 (d, J=8.4 Hz, 1H), 7.61 (dd, J=12.6 Hz, 7.8 Hz, 1H), 7.31 (t, J=8.4 Hz, 1H), 7.24 (d, J=7.8 Hz, 1H), 7.11 (t, J=9.6 Hz, 1H), 7.00 (d, J=7.2 Hz, 1H), 3.56-3.60 (m, 1H), 3.38-3.41 (m, 1H), 2.90-3.16 (m, 2H), 2.19-2.24 (m, 1H), 1.74-1.77 (m, 1H), 1.39-1.47 (m, 1H), 1.25 (s, 3H), 0.78-0.87 (m, 1H), 0.65-0.72 (m, 2H), 0.54-0.57 (m, 1H).

Example 9A and 9B

Preparation of (3S,4R or 3R,4S)-1-(1-(2-chloro-6-cyclopropyl benzoyl)-4-fluoro-1H-indazol-3-yl)-3-hydroxy-4-methylpiperidine-4-carboxylic acid (9A) and (3R,4S or 3S,4R)-1-(1-(2-chloro-6-cyclopropyl-benzoyl)-4-fluoro-1H-indazol-3-yl)-3-hydroxy-4-methylpiperidine-4-carboxylic acid (9B)

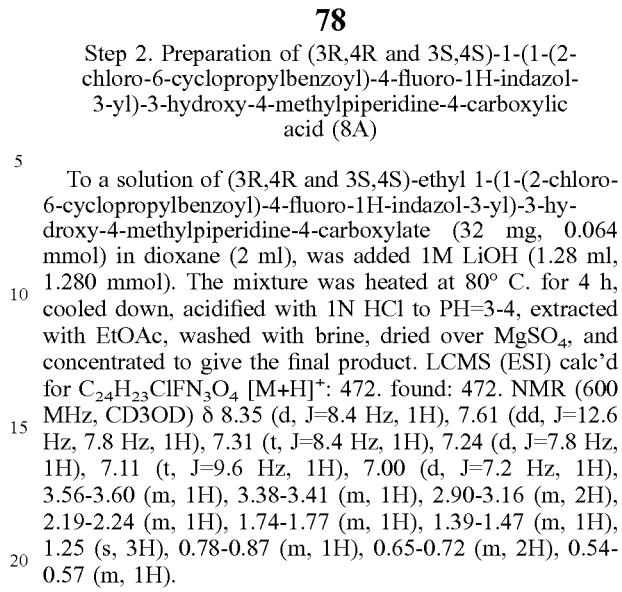

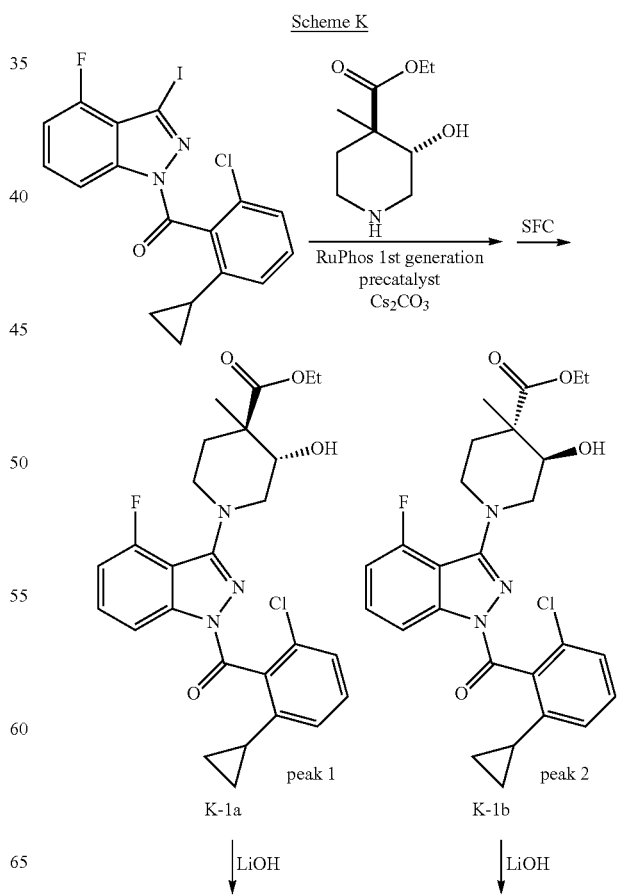

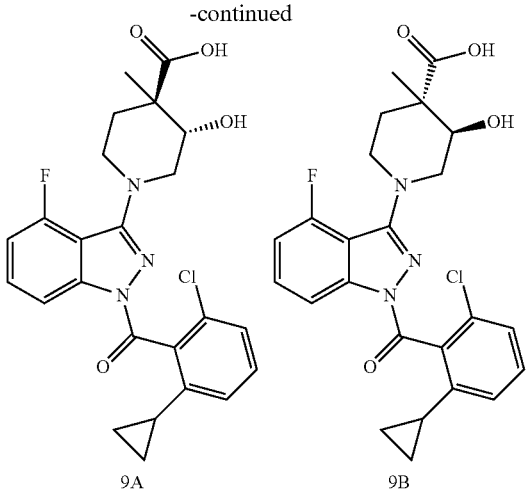

9A      9B

Step 1. Preparation of (3S,4R or 3R,4S)-ethyl 1-(1-(2-chloro-6-cyclopropylbenzoyl)-4-fluoro-1H-indazol-3-yl)-3-hydroxy-4-methylpiperidine-4-carboxylate (K-1a) and (3R,4S or 3S,4R)-ethyl 1-(1-(2-chloro-6-cyclopropylbenzoyl)-4-fluoro-1H-indazol-3-yl)-3-hydroxy-4-methylpiperidine-4-carboxylate (K-1b)

A mixture of (2-chloro-6-cyclopropylphenyl)(4-fluoro-3-iodo-1H-indazol-1-yl)methanone (400 mg, 0.908 mmol), (3S,4R and 3R,4S)-ethyl 3-hydroxy-4-methylpiperidine-4-carboxylate (221 mg, 1.180 mmol), Cs₂CO₃ (887 mg, 2.72 mmol) and Buchwald RuPhos Precatalyst (111 mg, 0.136 mmol) in Dioxane (4.5 ml) was degassed for 5 min and heated to 80° C. for 14 h. LCMS showed product formation, along with some unreacted iodide. The mixture was cooled to room temperature, diluted with EtOAc and H₂O. The organic layer was separated, washed with brine, dried over MgSO₄, concentrated. The residue was purified by flash chromatography (10-70% EtOAc/hexane) to give 26 mg of racemic product. This material was separated by chiral separation (Column: Chiralcel OJ-H, 21×250 mm, 10% MeOH in CO₂) to give two enantiomers: peak1 (K-1a, 5.24 min) 6 mg and peak2 (K-1b, 7.05 min) 7 mg. LCMS (ESI) calc'd for $C_{26}H_{27}ClFN_3O_4$ [M+H]⁺: 500. found: 500. NMR (600 MHz, CD3OD) δ 8.36 (d, J=8.4 Hz, 1H), 7.61-7.65 (m, 1H), 7.34 (t, J=8.4 Hz, 1H), 7.25-7.28 (m, 1H), 7.14 (t, J=9.6 Hz, 1H), 7.02 (dd, J=8.4, 3.6 Hz) 1H), 4.10-4.16 (m, 2H), 3.70-3.73 (m, 1H), 3.36-3.50 (m, 3H), 3.15-3.22 (m, 1H), 2.24-2.30 (m, 1H), 1.74-1.80 (m, 1H), 1.49-1.57 (m, 1H), 0.81-0.89 (m, 1H), 0.67-0.77 (m, 2H), 0.54-0.60 (m, 1H).

Step 2. Preparation of (3S,4R or 3R,4S)-1-(1-(2-chloro-6-cyclopropyl benzoyl)-4-fluoro-1H-indazol-3-yl)-3-hydroxy-4-methylpiperidine-4-carboxylic acid (9A)

To a solution of (3S,4R or 3R,4S)-ethyl 1-(1-(2-chloro-6-cyclopropylbenzoyl)-4-fluoro-1H-indazol-3-yl)-3-hydroxy-4-methylpiperidine-4-carboxylate (K-1a) (6 mg, 0.012 mmol) in THF (1 ml)/MeOH (1.000 ml) was added LiOH (0.360 ml, 0.360 mmol). The mixture was heated at 80° C. for 2 h. TLC showed completion. The mixture was cooled down, acidified with 1N HCl to pH=3-4, extracted with EtOAc, washed with brine, dried over MgSO₄, and concentrated to give final product of the title compound. LCMS (ESI) calc'd for $C_{24}H_{23}ClFN_3O_4$ [M+H]⁺: 472. found: 472.

Step 3. (3R,4S or 3S,4R)-1-(1-(2-chloro-6-cyclopropylbenzoyl)-4-fluoro-1H-indazol-3-yl)-3-hydroxy-4-methylpiperidine-4-carboxylic acid (9B)

The other enantiomer was prepared similarly from the enantiomeric ester (K-1b), as can be achieved by those of ordinary skill in the art of organic synthesis in light of the present disclosure. LCMS (ESI) calc'd for $C_{24}H_{23}ClFN_3O_4$ [M+H]⁺: 472. found: 472.

Example 10A

Preparation of 1-(1-(2-chloro-6-(trifluoromethyl)benzoyl)-4-fluoro-1H-indazol-3-yl)-2-oxopiperidine-4-carboxylic acid (10A)

Scheme L

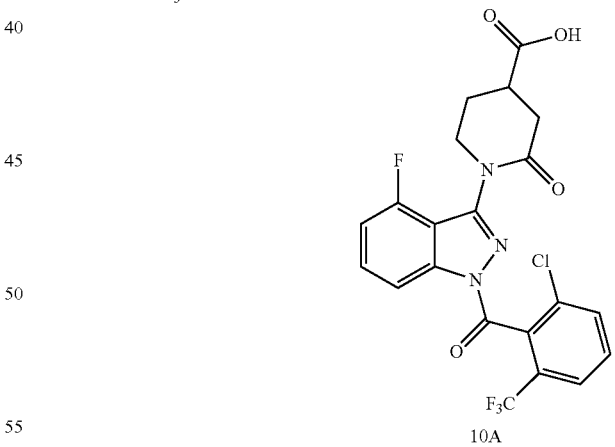

10A

To a solution of 1-(1-(2-chloro-6-(trifluoromethyl)benzoyl)-4-fluoro-1H-indazol-3-yl)piperidine-4-carboxylic acid (75 mg, 0.156 mmol) and NaIO₄ (60 mg, 0.309 mmol) in MeCN (30 mL) was added RuCl₃ (66 mg, 0.39 mmol) under N₂, and the mixture was stirred at 20° C. for 3 hrs. The suspension was filtered through a pad of celite and washed with EtOH. The combined organics were dried over Na₂SO₄ and concentrated. The crude product was purified by prep-TLC (PE:EA=5:1) to obtain the title product (15 mg, yield: 20%). LCMS (ESI) calc'd for $C_{21}H_{14}ClF_4N_3O_4$ [M+H]⁺:

484. found: 484. ¹H-NMR (400 MHz, CDCl₃) δ 8.29 (1H, d, J=8.4 Hz), 7.50-7.64 (4H, m), 7.01 (1H, t, J=9.2 Hz), 3.60-3.75 (2H, m), 2.95 (1H, d, J=5.2 Hz), 2.74-2.85 (2H, m), 2.24 (1H, d, J=13.2 Hz), 2.00-2.14 (1H, m).

Example 11A

Preparation of 1-(1-(2-chloro-6-(trifluoromethyl)benzoyl)-4-fluoro-1H-indazol-3-yl)-2-methylpiperidine-4-carboxylic acid (11A)

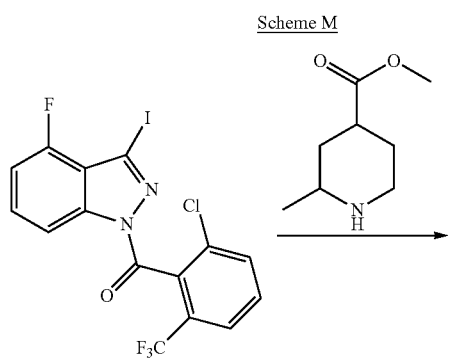

Scheme M

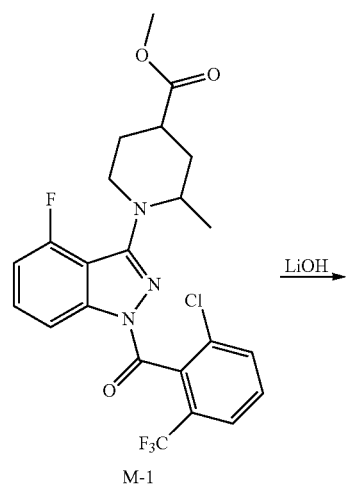

Step 1. Preparation of methyl 1-(1-(2-chloro-6-(trifluoromethyl)benzoyl)-4-fluoro-1H-indazol-3-yl)-2-methylpiperidine-4-carboxylate (M-1)

To a solution of methyl 2-methylpiperidine-4-carboxylate (67 mg, 0.4 mmol, mixture of cis/trans isomers, racemic), (2-chloro-6-(trifluoromethyl)phenyl)(4-fluoro-3-iodo-1H-indazol-1-yl)methanone (100 mg, 0.2 mmol), Cs₂CO₃ (209 mg, 0.6 mmol) in dioxane (1 mL) was added Pd-Ruphos pre-catalyst (20 mg) under N₂. The mixture was stirred at 90° C.-100° C. overnight. The residue was purified by prep-TLC (PE:EA=5:1) to give the title compound (20 mg, yield: 19%, mixture of cis/trans isomers, racemic). LCMS (ESI) calc'd for C₂₃H₂₀ClF₄N₃O₃ [M+H]⁺: 498. found: 498.

Step 2. Preparation of 1-(1-(2-chloro-6-(trifluoromethyl)benzoyl)-4-fluoro-1H-indazol-3-yl)-2-methyl-piperidine-4-carboxylic acid. (11A)

To a solution of methyl 1-(1-(2-chloro-6-(trifluoromethyl)benzoyl)-4-fluoro-1H-indazol-3-yl)-2-methylpiperidine-4-carboxylate (M-1) (40 mg, 80 umol) in dioxane (1 mL) and H₂O (0.5 mL) was added LiOH (8 mg, 0.3 mmol), and the mixture was stirred at room temperature for 2 h. After H₂O (2 mL) was added, the mixture was adjusted to pH=1-2 with HCl (aq.), and extracted with EtOAc (10 mL*3). The organic layer was removed under vacuum, and the residue was purified by prep-HPLC (acetonitrile+0.75‰ trifluoroacetic acid in water) to give the title compound (30 mg, yield: 77%, mixture of cis/trans isomers, racemic) as a white solid. LCMS (ESI) calc'd for C₂₂H₁₈ClF₄N₃O₃ [M+H]⁺: 484. found: 484. ¹H-NMR (400 MHz, MeOD) δ 8.24-8.35 (1H, m), 7.76-7.84 (2H, m), 7.65-7.73 (2H, m), 7.18 (1H, dd, J=8.8, 10.0 Hz), 3.74 (1H, d, J=12.8 Hz), 3.23 (1H, dd, J=3.52, 6.26 Hz), 2.81-2.94 (1H, m), 2.45-2.50 (1H, m), 1.89-1.90 (2H, m), 1.61-1.82 (2H, m), 1.05-1.10 (3H, m).

Example 12A

Preparation of 1-(1-(2-chloro-6-(trifluoromethyl)benzoyl)-6-(3-methoxy azetidine-1-carbonyl)-1H-indazol-3-yl)piperidine-4-carboxylic acid (12A)

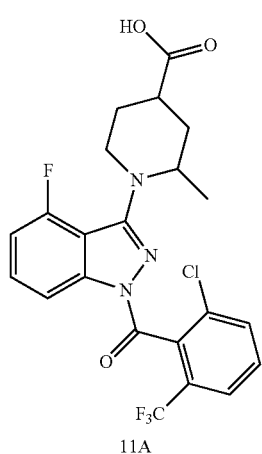

11A

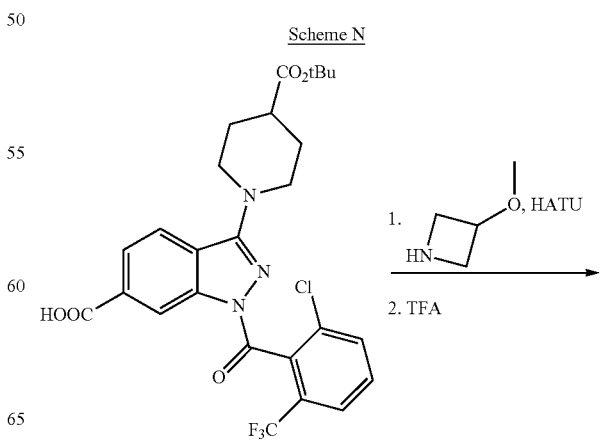

Scheme N

-continued

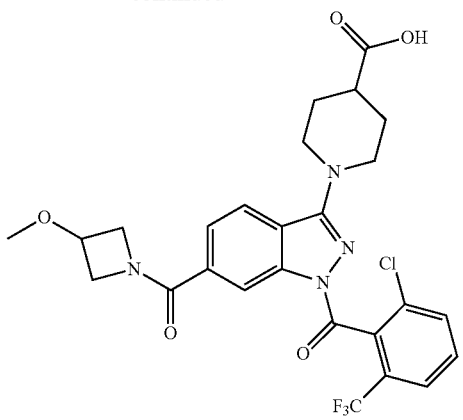

To a vial were added 3-(4-(tert-butoxycarbonyl)piperidin-1-yl)-1-(2-chloro-6-(trifluoromethyl)benzoyl)-1H-indazole-6-carboxylic acid (50 mg, 0.091 mmol), 3-methoxyazetidine hydrochloride (16.79 mg, 0.136 mmol), HATU (51.7 mg, 0.136 mmol), DMF (906 μl), and DIPEA (63.3 μl, 0.362 mmol) and the reaction was allowed to stir for 2 hours at room temperature. TFA (174 μl, 2.265 mmol) was then added to the solution dropwise and the resulting solution was allowed to stir for an additional 2 hours. The reaction was then concentrated and the residue was purified by Prep-HPLC (Acetonitrile/Water+0.10% TFA 50-100%) to give the desired product as a colorless solid. (19 mg, 37%) LCMS (ESI) calc'd for $C_{26}H_{24}ClF_3N_4O_5$ [M+H]$^+$: 565. found: 565. $^1$H NMR (600 MHz, DMSO) δ 8.61 (s, 1H), 8.09 (d, J=8.4 Hz, 1H), 7.93 (d, J=8.1 Hz, 1H), 7.87 (d, J=7.9 Hz, 1H), 7.75 (t, J=8.1 Hz, 1H), 7.64 (d, J=8.3 Hz, 1H), 4.45 (bs, 1H), 4.30-4.19 (m, 2H), 4.13 (d, J=8.1 Hz, 1H), 3.87 (d, J=8.5 Hz, 1H), 3.75 (d, J=13.3 Hz, 2H), 3.20 (s, 3H), 2.92 (t, J=12.2 Hz, 2H), 2.45-2.35 (m, 1H), 1.81 (d, J=11.0 Hz, 2H), 1.6-1.5 (m, 2H).

The following examples shown in TABLE 6 were prepared following similar procedures described for Example 12A, in Scheme N which can be achieved by those of ordinary skill in the art of organic synthesis in light of the present disclosure.

TABLE 6

| Ex. | Chemical Name | Structure | LCMS [M + H]$^+$ Found |
|---|---|---|---|
| 12B | (S)-1-(1-(2-chloro-6-(trifluoromethyl)benzoyl)-6-(2-methylpyrrolidine-1-carbonyl)-1H-indazol-3-yl)piperidine-4-carboxylic acid | 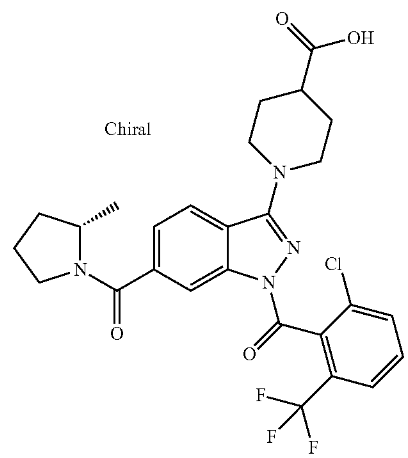 [SMILES: C[C@H]1CCCN1C(=O)c1ccc2c(N3CCC(C(=O)O)CC3)nn(C(=O)c3c(Cl)cccc3C(F)(F)F)c2c1] | 563 |
| 12C | (S)-1-(1-(2-chloro-6-(trifluoromethyl)benzoyl)-6-(3-methoxypyrrolidine-1-carbonyl)-1H-indazol-3-yl)piperidine-4-carboxylic acid | 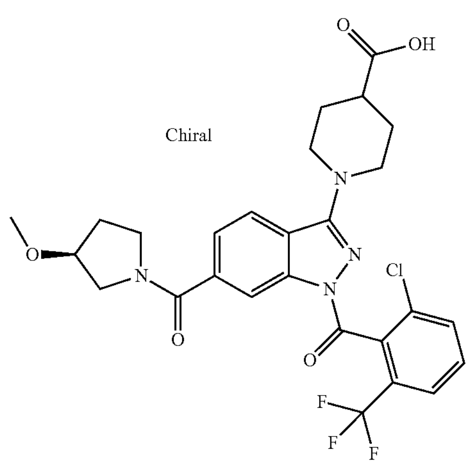 [SMILES: CO[C@H]1CCN(C(=O)c2ccc3c(N4CCC(C(=O)O)CC4)nn(C(=O)c4c(Cl)cccc4C(F)(F)F)c3c2)C1] | 579 |

TABLE 6-continued

| Ex. | Chemical Name | Structure | LCMS [M + H]+ Found |
|---|---|---|---|
| 12D | (R)-1-(1-(2-chloro-6-(trifluoromethyl)benzoyl)-6-(3-methoxypyrrolidine-1-carbonyl)-1H-indazol-3-yl)piperidine-4-carboxylic acid | 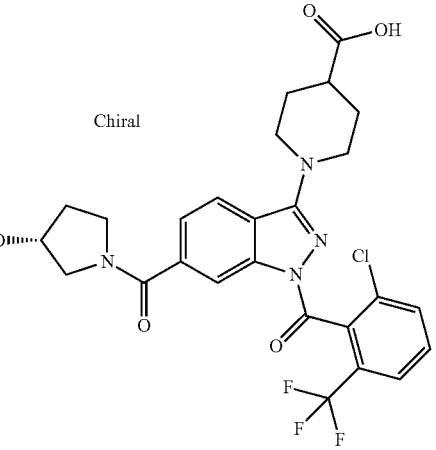 | 579 |

Biological Assays

The compounds of the invention inhibit RORgammaT activity. Activation of RORgammaT activity can be measured using, e.g., biochemical TR-FRET assay. In such an assay, interaction of cofactor-derived peptides with human RORgammaT-Ligand Binding Domain (LBD) can be measured. The TR-FRET technique is a sensitive biochemical proximity assay that will give information concerning the interaction of a ligand with the LBD, in the presence of cofactor-derived peptides (Zhou et al., Methods 25:54-61, 2001).

To identify novel antagonists of RORgammaT, an assay was developed which employs the interaction of RORgammaT with its co-activator peptide SRC1_2. This peptide mimics the recruitment of co-activators to RORgammaT through its interaction with the LXXLL (SEQ ID NO:1) (e.g., NR box) motifs (Xie et al., J. Immunol. 175: 3800-09, 2005; Kurebayashi et al., Biochem. Biophys. Res. Commun. 315: 919-27, 2004; Jin et al., Mol. Endocrinology 24:923-29, 2010). The RORγ-Ligand Binding Domain TR-FRET Assay was run according to the following protocol.

HIS-tagged RORγ-LBD protein was expressed in SF9 cells using a baculovirus expression system. The RORγ-LBD protein was purified by glutathione sepharose chromatography. Separately, SF9 cells not expressing any recombinant protein were lysed and the lysate was added to the purified RORγ-LBD at 0.25 μl lysate (from 10,000 SF9 cells)/nM purified protein. The mixture was then diluted in assay buffer (50 mM Tris pH 7.0, 50 mM KCl, 1 mM EDTA, 0.1 mM DTT) to obtain RORγ-LBD final concentration of 3 nM in 384-well assay plate.

Compounds to be tested were injected to the assay plate using Acoustic Droplet Ejection technology by Echo 550 liquid handler (Labcyte, CA).

A stock of biotinylated-LXXLL peptide from coactivator SRC1 (Biotin-CPSSHSSLTERHKILHRLLQEGSPS) (SEQ ID NO:2) was prepared in assay buffer and added to each well (100 nM final concentration). A solution of Europium tagged anti-HIS antibody (1.25 nM final concentration) and APC conjugated streptavidin (8 nM final concentration) were also added to each well.

The final assay mixture was incubated overnight at 4° C., and the fluorescence signal was measured on an Envision plate reader: (Excitation filter=340 nm; APC emission=665 nm; Europium emission=615 nm; dichroic mirror=D400/D630; delay time=100 μs, integration time=200 μs). IC50 values for test compounds were calculated from the quotient of the fluorescence signal at 665 nm divided by the fluorescence signal at 615 nm.

Biological Data

The following table tabulates the biological data disclosed for the instant invention:

| Examples | Fret IC$_{50}$ (nM) |
|---|---|
| 1A | 791 |
| 1B | 886 |
| 1C | 6699 |
| 1D | 24 |
| 1E | 269 |
| 1F | 2469 |
| 1G | 3841 |
| 1H | 6174 |
| 1I | 23 |
| 1J | 7759 |
| 1K | 164 |
| 1L | 306 |
| 1M | 461 |
| 1N | 1259 |
| 1O | 1669 |
| 1P | 5573 |
| 1Q | 7443 |
| 1R | 261 |
| 1S | 317 |
| 2A | 10 |
| 2B | 20 |
| 3A | 4 |
| 3B | 3 |
| 4A | 611 |
| 4B | 15 |
| 5A | 1713 |
| 5B | 6589 |
| 5C | 1421 |
| 5D | 411 |
| 6A | 2 |
| 6B | 29 |
| 6C | 2 |
| 6D | 51 |

-continued

| Examples | Fret IC$_{50}$ (nM) |
|---|---|
| 7A | 39 |
| 8A | 197 |
| 9A | 2 |
| 9B | 78 |
| 10A | 92 |
| 11A | 30 |
| 12A | 24 |
| 12B | 139 |
| 12C | 30 |
| 12D | 107 |

X is C(O);
Y is N;
n=0, 1, 2, 3 or 4;
$A^4$ is $CR^4$ or N,
$A^5$ is $CR^5$,
$A^6$ is $CR^6$,
$A^7$ is $CR^7$,
$R^1$ is (i) $(C_{3-12})$carbocyclyl; or (ii) a 4- to 12-membered heterocyclyl,

The invention claimed is:
1. A compound according to Formula I

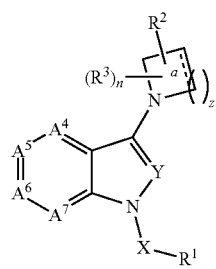

or a pharmaceutically acceptable salt or solvate thereof, wherein:
a is a bond or no bond;
z is 1, 2 or 3;

both (i) and (ii) are substituted with one, two, or three $R^8$;

$R^2$ is hydroxycarbonyl or hydroxycarbonyl$(C_{1-10})$alkyl;

$R^3$ is hydrogen, halogen, cyano, nitro, hydroxy, (C1-3) alkylC(O)O—, phenyl, $(C_{1-4})$alkyl, oxo, or $(C_{1-4})$ alkoxy, wherein $(C_{1-4})$alkyl and $(C_{1-4})$alkoxy are optionally substituted with one or more halogen;

optionally when z is 3, a represents no bond and two $R^3$ groups are attached to the two carbons flanking the N atom of the piperidinyl ring formed when z is 3, such that the two $R^3$ groups join to form a 2- or 3-carbon bridge with the piperidinyl ring to form an azabicyclo [3.2.1]octanyl or azabicyclo [3.3.1]nonanyl ring;

$R^4$, $R^5$, $R^6$ and $R^7$ independently are H, halogen, amino, cyano, hydroxy, $(C_{1-3})$alkoxy, $(C_{1-4})$alkyl, $(C_{0-10})$alkyl) aminocarbonyl, (di)$(C_{1-6})$alkylaminocarbonyl or amino ($C_{1-4}$)alkyl, wherein ($C_{1-3}$)alkoxy, ($C_{1-4}$)alkyl, ($C_0$-$C_{10}$)alkyl)aminocarbonyl, (di)($C_{1-6}$)alkylaminocarbonyl and amino($C_{1-4}$)alkyl are optionally substituted with one or more halogen, hydroxyl or ($C_{1-3}$)alkoxy; or a group having the formula

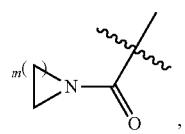

optionally substituted with one or more of the following: ($C_{1-10}$)alkyl, halogen, amino, cyano, hydroxy, ($C_{1-3}$)alkoxy, and wherein m is 1, 2, 3, or 4;

$R^8$ is halogen, cyano, amino, ($C_{1-3}$)alkoxycarbonyl, (di)($C_{1-6}$)alkylaminocarbonyl, ($C_{1-4}$)alkyl, ($C_{3-7}$)cycloalkyl, ($C_{3-5}$)heterocycloalkyl, or ($C_{1-3}$)alkoxy, wherein ($C_{1-3}$)alkoxycarbonyl, (di)($C_{1-6}$)alkylaminocarbonyl, ($C_{1-4}$)alkyl and ($C_{1-3}$)alkoxy are optionally substituted with one, two or three halogens.

2. The compound of claim 1 having Formula Ia

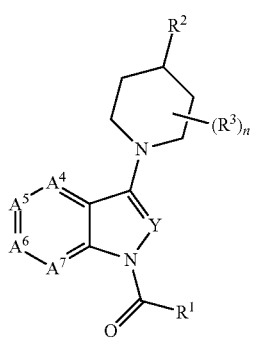

or a pharmaceutically acceptable salt or solvate thereof.

3. The compound of claim 1 having Formula Ib

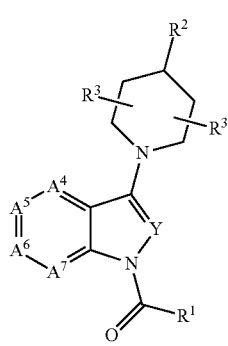

or a pharmaceutically acceptable salt or solvate thereof.

4. The compound of claim 3, wherein the compound is a compound of Formula Ib or a pharmaceutically acceptable salt thereof.

5. The compound of claim 3 having Formula Ic

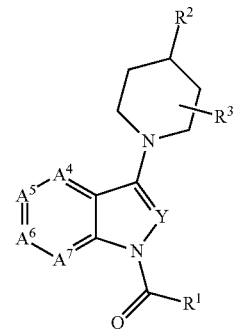

or a pharmaceutically acceptable salt or solvate thereof.

6. The compound of claim 2 having Formula Id

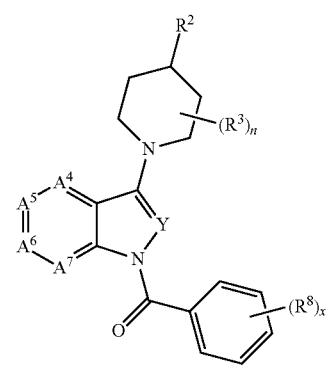

wherein x is 1, 2, 3, 4 or 5, or a pharmaceutically acceptable salt or solvate thereof.

7. The compound of claim 6 having Formula Ie

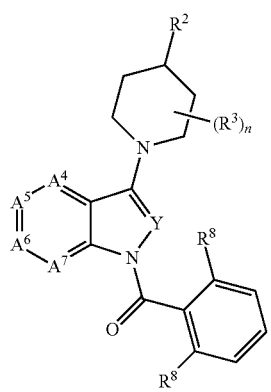

or a pharmaceutically acceptable salt or solvate thereof.

8. The compound of claim 7 having Formula If

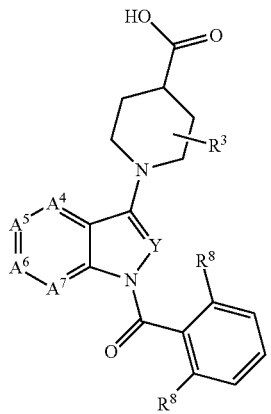

or a pharmaceutically acceptable salt or solvate thereof.

9. The compound of claim 1, wherein $A^4$ is $CR^4$.

10. The compound of claim 9, wherein $R^1$ is $(C_{6-14})$aryl, optionally substituted with one, two, or three $R^8$.

11. The compound of claim 10, wherein $R^1$ is phenyl substituted with one, two or three $R^8$.

12. The compound of claim 11, wherein $R^2$ is C(O)OH.

13. A compound selected from:
(3R,4R and 3S, 4S)-1-(1-{[2-chloro-6-(trifluoromethyl)phenyl]carbonyl}-1H-pyrazolo[4,3-b]pyridin-3-yl)-3-methylpiperidine-4-carboxylic acid;
8-(1-{[2-chloro-6-(trifluoromethyl)phenyl]carbonyl}-1H-pyrazolo[4,3-b]pyridin-3-yl)-8-azabicyclo[3.2.1]octane-3-carboxylic acid;
1-(1-{[2-chloro-6-(trifluoromethyl)phenyl]carbonyl}-4-fluoro-1H-indazol-3-yl)pyrrolidine-3-carboxylic acid;
(3R,4R and 3S,4S)-1-(1-{[2-chloro-6-(trifluoromethyl)phenyl]carbonyl}-4-fluoro-1H-indazol-3-yl)-3-methylpiperidine-4-carboxylic acid;
1-(1-{[2-chloro-6-(trifluoromethyl)phenyl]carbonyl}-4-fluoro-1H-indazol-3-yl)-4-methylpiperidine-4-carboxylic acid;
1-(1-{[2-chloro-6-(trifluoromethyl)phenyl]carbonyl}-4-fluoro-1H-indazol-3-yl)-4-(trifluoromethyl)piperidin-4-ol;
1-(1-{[2-chloro-6-(trifluoromethyl)phenyl]carbonyl}-4-fluoro-1H-indazol-3-yl)-4-phenylpiperidine-4-carboxylic acid;
cis-4-[(1-{[2-chloro-6-(trifluoromethyl)phenyl]carbonyl}-4-fluoro-1H-indazol-3-yl)amino]cyclohexanecarboxylic acid;
1-(1-{[2-chloro-6-(trifluoromethyl)phenyl]carbonyl}-4-fluoro-1H-indazol-3-yl)piperidine-4-carboxylic acid;
[1-(1-{[2-chloro-6-(trifluoromethyl)phenyl]carbonyl}-4-fluoro-1H-indazol-3-yl)piperidin-4-yl]acetic acid;
1-(1-{[2-chloro-6-(trifluoromethyl)phenyl]carbonyl}-1H-pyrazolo[4,3-b]pyridin-3-yl)-3-hydroxypiperidine-4-carboxylic acid;
1-(1-{[2-chloro-6-(trifluoromethyl)phenyl]carbonyl}-1H-pyrazolo[4,3-b]pyridin-3-yl)-1,2,3,6-tetrahydropyridine-4-carboxylic acid;
1-(1-{[2-chloro-6-(trifluoromethyl)phenyl]carbonyl}-1H-pyrazolo[4,3-b]pyridin-3-yl)piperidine-4-carboxylic acid;
1-(1-{[2-chloro-6-(trifluoromethyl)phenyl]carbonyl}-1H-pyrazolo[4,3-b]pyridin-3-yl)-4-fluoropiperidine-4-carboxylic acid;
1-(1-{[2-chloro-6-(trifluoromethyl)phenyl]carbonyl}-1H-pyrazolo[4,3-b]pyridin-3-yl)-3-fluoropiperidine-4-carboxylic acid;
1-(1-{[2-chloro-6-(trifluoromethyl)phenyl]carbonyl}-1H-pyrazolo[4,3-b]pyridin-3-yl)-4-(trifluoromethyl)piperidin-4-ol;
[1-(1-{[2-chloro-6-(trifluoromethyl)phenyl]carbonyl}-1H-pyrazolo[4,3-b]pyridin-3-yl)azetidin-3-yl]acetic acid;
1-[1-{[2-chloro-6-(trifluoromethyl)phenyl]carbonyl}-6-(dimethylcarbamoyl)-1H-indazol-3-yl]piperidine-4-carboxylic acid;
1-[1-{[2-chloro-6-(trifluoromethyl)phenyl]carbonyl}-6-(hydroxymethyl)-1H-indazol-3-yl]piperidine-4-carboxylic acid;
1-(1-(2-chloro-6-(trifluoromethyl)benzoyl)-4-fluoro-1H-indazol-3-yl)pyrrolidine-3-carboxylic acid;
1-(1-(2-chloro-6-(trifluoromethyl)benzoyl)-4-methyl-1H-indazol-3-yl)piperidine-4-carboxylic acid;
1-(1-(2-chloro-6-cyclopropylbenzoyl)-4-fluoro-1H-indazol-3-yl)piperidine-4-carboxylic acid;
1-(1-(2-chloro-6-cyclobutylbenzoyl)-4-fluoro-1H-indazol-3-yl)piperidine-4-carboxylic acid;
(3R,4S and 3S,4R)-1-(1-(2-chloro-6-(trifluoromethyl)benzoyl)-4-fluoro-1H-indazol-3-yl)-3-methylpiperidine-4-carboxylic acid;
(3R,4R and 3S,4S)-1-(1-(2-chloro-6-(trifluoromethyl)benzoyl)-4-fluoro-1H-indazol-3-yl)-3-methylpiperidine-4-carboxylic acid;
8-(1-(2-chloro-6-(trifluoromethyl)benzoyl)-4-fluoro-1H-indazol-3-yl)-8-azabicyclo[3.2.1]octane-3-carboxylic acid;
1R,5S)-9-(1-(2-chloro-6-(trifluoromethyl)benzoyl)-4-fluoro-1H-indazol-3-yl)-9-azabicyclo[3.3.1]nonane-3-carboxylic acid;
1-(1-(2-chloro-6-(trifluoromethyl)benzoyl)-4-fluoro-1H-indazol-3-yl)-2-ethylpiperidine-4-carboxylic acid;
1-(1-(2-chloro-6-(trifluoromethyl)benzoyl)-4-fluoro-1H-indazol-3-yl)-4-hydroxypiperidine-4-carboxylic acid;
(3S,4R or 3R,4S)-1-(1-(2-chloro-6-cyclopropylbenzoyl)-4-fluoro-1H-indazol-3-yl)-3-hydroxypiperidine-4-carboxylic acid;
(3R,4S or 3S,4R)-1-(1-(2-chloro-6-cyclopropylbenzoyl)-4-fluoro-1H-indazol-3-yl)-3-hydroxypiperidine-4-carboxylic acid;
(3S,4R or 3R, 4S)-1-(1-(2-chloro-6-(trifluoromethyl)benzoyl)-4-fluoro-1H-indazol-3-yl)-3-hydroxypiperidine-4-carboxylic acid;
(3R,4S or 3S, 4R)-1-(1-(2-chloro-6-(trifluoromethyl)benzoyl)-4-fluoro-1H-indazol-3-yl)-3-hydroxypiperidine-4-carboxylic acid;
(3R,4R and 3S,4S)-1-(1-(2-chloro-6-(trifluoromethyl)benzoyl)-4-fluoro-1H-indazol-3-yl)-3-hydroxypiperidine-4-carboxylic acid;
(3R,4R)-1-(1-(2-chloro-6-cyclopropylbenzoyl)-4-fluoro-1H-indazol-3-yl)-3-hydroxy-4-methylpiperidine-4-carboxylic acid;
(3S,4R or 3R,4S)-1-(1-(2-chloro-6-cyclopropyl benzoyl)-4-fluoro-1H-indazol-3-yl)-3-hydroxy-4-methylpiperidine-4-carboxylic acid;
(3R,4S or 3S,4R)-1-(1-(2-chloro-6-cyclopropylbenzoyl)-4-fluoro-1H-indazol-3-yl)-3-hydroxy-4-methylpiperidine-4-carboxylic acid;
1-(1-(2-chloro-6-(trifluoromethyl)benzoyl)-4-fluoro-1H-indazol-3-yl)-2-oxopiperidine-4-carboxylic acid;
1-(1-(2-chloro-6-(trifluoromethyl)benzoyl)-4-fluoro-1H-indazol-3-yl)-2-methylpiperidine-4-carboxylic acid;

1-(1-(2-chloro-6-(trifluoromethyl)benzoyl)-6-(3-methoxy azetidine-1-carbonyl)-1H-indazol-3-yl)piperidine-4-carboxylic acid;

(S)-1-(1-(2-chloro-6-(trifluoromethyl)benzoyl)-6-(2-methylpyrrolidine-1-carbonyl)-1H-indazol-3-yl)piperidine-4-carboxylic acid;

(S)-1-(1-(2-chloro-6-(trifluoromethyl)benzoyl)-6-(3-methoxypyrrolidine-1-carbonyl)-1H-indazol-3-yl)piperidine-4-carboxylic acid; and (R)-1-(1-(2-chloro-6-(trifluoromethyl)benzoyl)-6-(3-methoxypyrrolidine-1-carbonyl)-1H-indazol-3-yl)piperidine-4-carboxylic acid.

14. A pharmaceutical composition comprising a compound of claim 1 or a pharmaceutically acceptable salt or solvate thereof, and one or more pharmaceutically acceptable excipients.

15. The pharmaceutical composition of claim 14, further comprising at least one additional therapeutically active agent.

16. A method for treating a disease or condition mediated by RORgammaT in a subject comprising administering to the subject an amount of a compound of claim or a pharmaceutically acceptable salt or solvate thereof, that is effective for treating the disease or condition mediated by RORgammaT in the subject, wherein the disease or condition is an autoimmune disease or inflammatory disease.

17. The method of claim 16, wherein the disease or condition is multiple sclerosis, inflammatory bowel disease, Crohn's disease, ankylosing spondylitis, psoriasis, rheumatoid arthritis, asthma, osteoarthritis, Kawasaki disease, Hashimoto's thyroiditis or mucosal leishmaniasis.

18. The compound of claim 2, wherein the compound is a compound of Formula Ia or a pharmaceutically acceptable salt thereof, where $R^2$ is —$CO_2H$, $R^1$ is phenyl substituted with two $R^8$, and each $R^8$ is independently halogen, $(C_{1-4})$alkyl, or $(C_{3-7})$cycloalkyl, wherein $(C_{1-4})$alkyl is optionally substituted with one, two, or three halogens.

19. The compound of claim 8, wherein the compound is a compound of Formula If or a pharmaceutically acceptable salt thereof, wherein each $R^8$ is independently (i) halogen or (ii) $(C_{1-4})$alkyl substituted with one, two, or three halogens.

20. The compound of claim 18, wherein $A^4$ is N.

21. The compound of claim 18, wherein $A^4$ is $CR^4$, where $R^4$ is halogen.

22. A pharmaceutical composition comprising a compound of claim 18 and one or more pharmaceutically acceptable excipients.

* * * * *

SEQUENCE LISTING

<160> NUMBER OF SEQ ID NOS: 2

<210> SEQ ID NO 1
<211> LENGTH: 5
<212> TYPE: PRT
<213> ORGANISM: Artificial Sequence
<220> FEATURE:
<223> OTHER INFORMATION: SRC1_2 peptide
<220> FEATURE:
<221> NAME/KEY: misc_feature
<222> LOCATION: (2)..(3)
<223> OTHER INFORMATION: Xaa can be any naturally occurring amino acid

<400> SEQUENCE: 1

Leu Xaa Xaa Leu Leu
1               5

<210> SEQ ID NO 2
<211> LENGTH: 25
<212> TYPE: PRT
<213> ORGANISM: Artificial Sequence
<220> FEATURE:
<223> OTHER INFORMATION: SRC1_2 peptide

<400> SEQUENCE: 2

Cys Pro Ser Ser His Ser Ser Leu Thr Glu Arg His Lys Ile Leu His
1               5                   10                  15

Arg Leu Leu Gln Glu Gly Ser Pro Ser
            20                  25